(12) United States Patent
McGall et al.

(10) Patent No.: US 7,282,327 B2
(45) Date of Patent: *Oct. 16, 2007

(54) NUCLEIC ACID LABELING COMPOUNDS

(75) Inventors: Glenn H. McGall, San Jose, CA (US); Anthony D. Barone, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 348 days.

This patent is subject to a terminal disclaimer.

(21) Appl. No.: 10/641,677

(22) Filed: Aug. 15, 2003

(65) Prior Publication Data

US 2004/0101892 A1 May 27, 2004

Related U.S. Application Data

(63) Continuation-in-part of application No. 10/314,012, filed on Dec. 5, 2002, now Pat. No. 6,864,059, which is a continuation-in-part of application No. 10/097,113, filed on Mar. 12, 2002, which is a continuation-in-part of application No. 09/952,387, filed on Sep. 11, 2001, now Pat. No. 6,965,020, which is a continuation-in-part of application No. 09/780,574, filed on Feb. 9, 2001, now Pat. No. 6,596,856, which is a continuation-in-part of application No. 09/126,645, filed on Jul. 31, 1998, now abandoned, which is a continuation-in-part of application No. 08/882,649, filed on Jun. 25, 1997, now Pat. No. 6,344,316, which is a continuation of application No. PCT/US97/01603, filed on Jan. 22, 1997.

(60) Provisional application No. 60/035,170, filed on Jan. 9, 1997, provisional application No. 60/010,471, filed on Jan. 23, 1996.

(51) Int. Cl.
C07H 21/02 (2006.01)
C07H 21/04 (2006.01)
C12Q 1/68 (2006.01)

(52) U.S. Cl. ............ 435/6; 536/23.1; 536/25.1
(58) Field of Classification Search ............ 435/6; 536/23.1, 25.1
See application file for complete search history.

(56) References Cited

U.S. PATENT DOCUMENTS 3,352,849 A 11/1967 Shan et al.
(Continued)

FOREIGN PATENT DOCUMENTS

DE 19509038 9/1996
(Continued)

OTHER PUBLICATIONS

Natalya Ramzaeva et al., "Oligonucleotides Functionalized By Fluorescein and Rhodamine Dyes: Michael Addition of Methyl Acrylate to 2'-Deoxypseudouridine," Helvetica Chemica Acta, vol. 83, 2000, pp. 1108-1126.
(Continued)

*Primary Examiner*—Shaojia Jiang
(74) *Attorney, Agent, or Firm*—Cooley Godward LLP; Thomas E. Malone

(57) ABSTRACT

Compounds of the following structure:

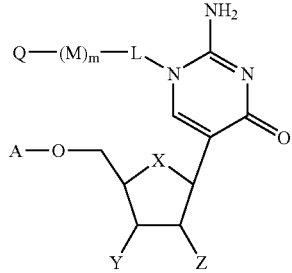

are useful as nucleic labeling compounds.

32 Claims, 23 Drawing Sheets

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,891,623 A | 6/1975 | Vorbruggen et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio et al. | |
| 4,366,241 A | 12/1982 | Tom et al. | |
| 4,594,339 A | 6/1986 | Lopez et al. | |
| 4,981,783 A | 1/1991 | Augenlicht | |
| 4,997,928 A | 3/1991 | Hobbs, Jr. | |
| 5,002,867 A | 3/1991 | Macevicz | |
| 5,143,854 A | 9/1992 | Pirrung et al. | |
| 5,151,507 A | 9/1992 | Hobbs, Jr. et al. | |
| 5,202,231 A | 4/1993 | Drmanac et al. | |
| 5,242,796 A | 9/1993 | Prober et al. | |
| 5,262,536 A | 11/1993 | Hobbs, Jr. | |
| 5,324,633 A | 6/1994 | Fodor et al. | |
| 5,332,666 A | 7/1994 | Prober et al. | |
| 5,422,241 A | 6/1995 | Goldrick et al. | |
| 5,424,186 A | 6/1995 | Fodor et al. | |
| 5,445,934 A | 8/1995 | Fodor et al. | |
| 5,543,292 A | 8/1996 | Imai et al. | |
| 5,571,639 A | 11/1996 | Hubbell et al. | |
| 5,608,063 A | 3/1997 | Hobbs, Jr. et al. | |
| 5,744,305 A | 4/1998 | Fodor et al. | |
| 6,174,998 B1 | 1/2001 | Muhlegger et al. | |
| 6,211,158 B1 | 4/2001 | Seela et al. | |
| 6,864,059 B2 * | 3/2005 | McGall et al. | 435/6 |

FOREIGN PATENT DOCUMENTS

| | | |
|---|---|---|
| EP | 0132621 | 2/1985 |
| EP | 0159719 | 10/1985 |
| EP | 0252683 | 1/1988 |
| EP | 0266787 | 5/1988 |
| EP | 0320308 | 6/1989 |
| EP | 0322311 | 6/1989 |
| EP | 0336731 | 10/1989 |
| EP | 0535242 | 4/1993 |
| EP | 0717113 | 6/1996 |
| EP | 0721016 | 7/1996 |
| JP | 61109797 | 5/1986 |
| WO | WO 89/10977 | 11/1989 |
| WO | WO 90/00626 | 1/1990 |
| WO | WO 90/03370 | 4/1990 |
| WO | WO 90/04652 | 5/1990 |
| WO | WO 90/15070 | 12/1990 |
| WO | WO 92/02258 | 2/1992 |
| WO | WO 95/00530 | 5/1992 |
| WO | WO 92/10092 | 6/1992 |
| WO | WO 92/10588 | 6/1992 |
| WO | WO 93/16094 | 8/1993 |
| WO | WO 93/17126 | 9/1993 |
| WO | WO 95/04594 | 2/1995 |
| WO | WO 95/04833 | 2/1995 |
| WO | WO 95/04834 | 2/1995 |
| WO | WO 95/11995 | 5/1995 |
| WO | WO 9520681 | 8/1995 |
| WO | WO 95/30774 | 11/1995 |
| WO | WO 95/355505 | 12/1995 |
| WO | WO 96/28460 | 9/1996 |
| WO | WO 97/10365 | 3/1997 |
| WO | WO 97/27317 | 7/1997 |
| WO | WO 97/28176 | 8/1997 |
| WO | WO 97/29212 | 8/1997 |
| WO | WO 98/11104 | 3/1998 |
| WO | WO 00/06771 | 2/2000 |
| WO | WO 92/072779 A2 | 9/2002 |

OTHER PUBLICATIONS

Akita, Y., et al., "Cross-Coupling Reaction of Chloropyrazines with Acetylenes", Chemical & Pharmaceutical Bulletin, 34 (4), (Apr. 1986), pp. 1447-1458.

Aoyagi, M., et al., "Nucleosides and Nucleotides. 115. Synthesis of 3-Alkyl-3- Deazainosines via Palladium-Catalyzed Intramolecular Cyclization: A New Confomational Lock with the Alkyl Group at the 3-Position of the 3-Deazainosine in Anti-Conformation", Tetrahedron Letters, 34 (1), (1993), pp. 103-106.

Avila, J.L., et al., "Biological Action of Pyrazolopyrimidine Derivatives Against Trypanosoma Cruzi. Studies In Vitro and In Vivo", Comp. Biochem. Physiol.., 86C (1), (1987), pp. 49-54.

Barringer, et al., "Blunt-end and single-strand litigations by *Escherichia coli* ligase: influence on an in vitro amplification scheme", Gene, 89, (1990), pp. 117-122.

Basnak, I., et al., "Some 6-Aza-5-Substituted-2'-Deoxyuridines Show Potent and Selective Inhibition of Herpes Simplex Virus Type 1 Thymidine Kinase", Nucleosides & Nucleotides, 17 (1-3), (1998), pp. 187-206.

Beabealashvilli, R.S., et al., "Nucleoside 5'-triphosphates modified at sugar residues as substrates for calf thymus terminal deoxynucleotidyl transferase and for AMV reverse transcriptase", Biochimica et Biphysica Acta, 868, (1986), pp. 136-144.

Bergeron, et al., "Reagents for the stepwise functionalization of spermine", J. Org. Chem., 53, (1998), pp. 3108-3111.

Bergstrom, D.E., et al., "Design and Synthesis of Heterocyclic Carboxamides as Natural Nucleic Acid Base Mimics", Nucleosides & Nucleotides, 15 (1-3), (1996), pp. 59-68.

Bobek, M., et al., "Nucleic Acids Components and their Analogues. XCVII. Synthesis of 5-Hydroxymethyl-6-Aza-2'-Deoxyuridine and 5-Hydroxymethyl-6-Aza-2'-Deoxycytidine", Collection Czechoslov. Chem. Commun., 32, (1967), pp. 3581-3586.

Brody, R.S., et al., "The Purification of Orotidine-5'-phosphate Decarboxylase from Yeast by Affinity Chromatography", The Journal of Biological Chemistry 254 (10), (1979), pp. 4238-4244.

Broude, N.E., et al., "Enhanced DNA sequencing by hybridization", PNAS, 91 (1994), 3072-3076.

Canard, B., et al., "Catalytic editing properties of DNA polymerases", PNAS, 92, (Nov. 1995), pp. 10859-10863.

Cech, D., et al., "New Approaches Toward the Synthesis of Non-Radioactively Labeled Nucleoside Triphosphates as Terminators for DNA Sequencing", Collect. Czech. Chem. Commun., 61, Special Issue, (1996), pp. S297-S300.

Chee, M., et al., "Accessing Genetic Information with High-Density DNA Arrays", Science, 274, (Oct. 25, 1996), pp. 610-614.

Chernetskii, V.P., et al., "Anamalous nucleosides and related compounds. XIV. Derivatives of 6-azacytidine.", Chemical Abstracts, 74 (21), Abstract No. 112367]. (1971).

Chidgeavadez, Z.G., et al., "2', 3'-Dideox-3' aminonucleosides 5'-triphosphates are the terminators of DNA synthesis catalyzed by DNA polymerases", Nucleic Acids Research, 12 (3), (1984), pp. 1671-1686.

Chu, et al., "General Synthesis of 2', 3'-dideoxynucleosides and 2', 3'-didehydro-2', 3'-dideoxynucleosides", J. Org. Chem., 54, (1989), pp. 2217-2225.

Cottam, Howard, B., et al., "New Adenosine Kinase Inhibitors with Oral Antiinflammatory Activity: Synthesis and Biological Evaluation", Journal of Medicinal Chemistry, 36 (22), Oct. 29, 1993), pp. 3424-3430.

Curriden, M., "A New Evidence Tool—First Use of Mitochondrial DNA Test in a U.S. criminal trial", ABA Journal, (Nov. 1996), 1 p.

Danshcer, et al., "Automettallographic silver amplification of colloidal gold", J. Histotech., 16, (1993), pp. 201-207.

Depelley, J., et al., "New Non-Aromatic Triazinic Nucleosides" Synthesis and Antiretroviral Evaluation of Beta-Ribosylamine Nucleoside Analogs, Nucleosides & Nucleotides 15(5), (1996), pp. 995-1008.

Dueholm, et al., "2-3-dideoxy-furanoses in covergent synthesis of 2', 3'-dideoxy nucleosides", Synthesis, (1992), pp. 1-22.

Edo, K., et al., "Studies on Pyrimidine Derivatives. IX. Coupling Reaction of Mono-substituted Acetylenes with Iodopyrimidines", Chemical & Pharmaceutical Bulletin, 26(12), (Dec. 1978), pp. 3843-3850.

Eggers, M., et al., "A Microchip for Quantitative Detection of Molecules Utilizing Luminescent and Radioisotope Reporter Groups", Bio Techniques, 17(3), (1994), 516-525.

Feldman, W., et al., "Gray Code Masks for Sequencing by Hybridization", Genomics, 23 (1994), 233-235.

Fodor, et al., "Light-directed, spatially addressable parallel chemical synthesis" Science, 251, (1991), 767-773.

Freskos, J.M., "Synthesis of 2'-Deoxypyrimidine Nucleosides Via Copper (1) Iodine Catalysis", Nucleosides & Nucleotides, 8 (4), (1989), pp. 549-555.

Galushko, S.V., et al., "Relationship between retention parameters in reversed-phase high performance liquid chromatography and antitumour activity of some pyrimidine bases and nucleosides", Journal of Chromatography, 547 (1991), pp. 161-166.

Galushko, S.V., et al., "Reversed-phase HPLC of N4-and O'derivatives of 6 azacytidine", Chemical Abstracts, 111 (26), Abstract No. 243960u, (1990).

Grzybowski, et al., "Synthesis and antibody-mediated detection of oligonucleotides containing multiple 2,4-dinitrophenyl reporter groups", Nucleic Acids Research, 21 (8), 1(1993), pp. 1705-1712.

Guatelli, et al., "Isothermal, in vitro amplification of nucleic acids by a multienzyme reaction modeled after retroviral replication", PNAS, 87m, (1990), pp. 1874-1878.

Hamilton, H., et al., "C4-Substituted 1-beta-D-Ribofuranosyllpyrazolo [3, 4- d]pyrimidens as Adenosine Agonist Analogues", J. Med. Chem., 26 (11), (1993, pp. 1601-1606).

Herrlein, et al., "57.3'-amino-modified nucleotides useful as potent chain terminators for current DNA sequencing method", Helv. Chim. Acta. 77, (1994), pp. 588-596.

Hobbs, Jr., F.W., et al., "Palladium-catalyzed synthesis of alkynylamino nucleosides. A universal linker for nucleic acids", J. Org. Chem., 54, (1980), pp. 3420-3422.

Hoheisel, J.D., "Application of Hybridization Techniques to Genome Mapping and . . . ", Trend in Genetics, 10 (3), (1994), 79-83.

Holy, A., et al., "Oligonucleotidic Compounds, XVII. Synthesis of Oligonucletides Containing 6-Azauriding and 6-Azacytidine", Collectino Czechoslov. Chem. Commun., 32 (1967), pp. 2980-2997.

Izuta, S., et al., "Chain Termination with Sugar-Modified Nucleotide Analogs in the DNA Synthesis by DNA Polymerase Y", Nucleosides & Nucleotides, 15 (1-3), (1996), pp. 683-692.

Johnson, W.T., et al., "The Synthesis and stability of oligodeoxyribonucleotides containing the deoxyadenosine mimic 1-(2'-deoxy-beta-D-ribofuranosyl)imidazole-4-carboxamide", Nucleic Acids Research, 25 (3), (1997), pp. 559-567.

Kallioniemi, A., et al., "Comparative Genomic Hybridization for Molecular Cytogenetic", Science, 258, (1992), 818-821.

Khrapko, K.R., et al., "An Oligonucleotide Hybridization Approach to DNA Sequencing, Hybridization Approach to DNA Sequencing", FEBS Letters, 6, (1989), 118-122.

Kohler, P. et al., "264. Nucleoside und Nucleotide. Tiel 15. Synthese von Desoxyribonucleosid-monophosphaten und-triphosphaten mit 2 (1 H)-Pyrimidinon, 2 (1 H)-Pyridinon und 4-Amino-2 (1 H)-pyridinon als Basen", Helvetica Chimica Acta, 63, (1980), pp. 2488-2494.

Kutateladze, T., et al., "3'-Deoxy-3'-aminonucleoside 5'-triphosphates—Terminators of RNA synthesis, catalyzed by DNA-dependent RNA polymerase from Escherichia coli", FEBS Letters, 153 (2), Mar. 1983), pp. 420-426.

Kwoh, et al., "Transcription-based amplification system and detection of amplified human immunodeficiency virus type 1 with a bead-based sandwich hybridization format", PNAS, 86, (1989), LPP. 1173-1177.

Landegren, et al., "A ligase-mediated gene detection technique", Science, 241, (1988), pp. 1077-1080.

Langer, et al., "Enzymatic synthesis of biotin-labeled polynucleotides: Novel nucleic acid affinity probes", PNAS, 78 (1981), pp. 6633-6637.

Lazurkevich, Z.V. et al., "Growth activity of 6-substituted azauracits", Chemical Abstracts, 102 (25), Abstract No. 216761w, (1985).

Le Bec, C., et al., " Derivatives of Imidazole-4-Carboxamide as Substrates for Various DNA Polymerases", Nucleosides & Nucleotides, 167 (7-9), (1997), pp. 1301-1302.

Lennon, G.G., et al., "Hybridization analyses of arrayed cDna libraries", Trends in genetics, 7 (10), (1991), 314-317.

Lipshutz, R.J. et al., "Using Oligonucleotide Prode Arrays to access Genetic Diversity", Biotechniques, 19 (3), (1995), 442-447.

Lockhart, D.J., et al., "Expression monitoring by hybridization to high-density", Nature Biotechnology, 14(13), (1996), 1675-1680.

Ludwig, et al., "Rapid and efficient synthesis of nucleoside 5'-O-(1-thiotriphosphates), 5'-triphosphates and 2', 3'-cyclophosphorthioates using 2-chloro-4H-1,3,2-benzodioxaphosphorin-4-one", J. Org. Chem., 54, (1989), pp. 631-635.

Mikkelsen, et al., "Genetics of the malignant progression of astrocytoma", J. Cell, Biochem., 46, (1991), pp. 3-8.

Mirkin, et al., "A DNA-based method for rationally assembling nanoparticles into macroscopic materials", Nature, 382, (1996), pp. 607-609.

Misura, K., et al., "Biotinyl and phosphotyrosinyl phosphoramidite derivatives useful in the incorporation of multiple reporter groups on synthetic oligonucleotides", Nucleic Acids Research, 18 (15), (1990), pp. 4345-4354.

Mitchell, et al., "Synthesis and antiviral properties of 5-(2-substituted vinyl)-6-aza-2'-deoxyuridines", J. Chem. Med., 29, (1986), pp. 809-816.

Nelson, P.S. et al., "Oligonucleotide labeling methods 3. Direct labeling of oligonucleotides employing a novel, non-nucleosidic, 2-aminobutyl-1, 3-propanediol backbone", Nucleic Acids Research, 20 (23), (1992), pp. 6253-6259.

Niedballa, et al., "A general synthesis of N-glycosides. I. Synthesis of pyrimidine nucleosides", J. Org. Chem., 39 (1974), pp. 3654-3660.

Nishida, M., et al., "Facile Perfluoralkylation of Uraciles and Uridines at the C-5 Position", Journal of Fluorine Chemistry, 63, (1993, pp. 43-52.

Ohsawa, A., et al., "Alkynylation of Halopyridazines and Their N-Oxides", Chemical & Pharmaceutical Bulletin, 28 (12), (Dec. 1980), pp. 3488-3493.

Petrie, et al., "A novel biotinylated adenylate analogue derived from pyrazolo [3,4-d]pyrimidine for labeling DNA probes", Bioconjugage Chem., 2, (1991), pp. 441-446.

Pevzner, P.A. et al., "Improved Chips for Sequencing by Hybridization", Journal of Biomolecular Structure, (1991), 339-410.

Pirrung, et al., "A convenient procedure for the deprotection of silylated nucleosides and nucleotides using triethlamine trihydrofluoride", Biorg. Med. Chem. Lett., 4, (1994), pp. 1345-1346.

Pochet, S., et al., "Ambiguous Base Pairing of 1-(2-Deoxy-beta-D-Ribofuranosyl) Imidazole-4-Carboxamide During PCR", Nucleosides & Nucleotides, 16(7-9), (1997), pp. 1749-1752.

Pochet, et al., "Enzymatic synthesis of 1-(2-deoxy-beta-D-ribofuranosyl) imidazole-4-carboxamide, a simplified DNA building block", Bioorg. Med. Chem. Lett., 5, (1995, pp. 1679-1684.

Pochet, S. et al., "Synthesis and enzymatic polmerisation of 5-amino-1-(2'-depxy-beta-D-ribofuranosyl) imidazole-4-carboxamide-5'triphosphate", Nucleic Acids Research, Nucleic Acids Research, 18 (23), (Dec. 11, 1990), pp. 7127-7131.

Prober, James, M., et al., "A System for Rapid DNA Sequencing with Fluorescent Chain-Terminating Dideoxynucleotides", Science, 238, (Oct. 16, 1987), pp. 336-341.

Prystas, M., et al., "Nucleic Acids Components and their Analogues. CXXI. Glycosylation of 6-Azathymine by the Silylation Process", Collection Czechoslov. Chem. Commun., 34 (1969), pp. 1104-1107.

Rideout, J.L., et al., "Pyrazolo[3,4-d]pyrimidine Ribonucleosides as Anticoccidials. 2. Synthesis and Activity of Some Nucleosides of 4-(Alkylamino)-1H-Pyrazolo[3,4-d]pyrimidines", J. Med. Chem,. 25 (9), (1982) pp. 1040-1044.

Robins, et al., "Nucleic acid related compounds. 42. A general procedure for the efficient deoxygenation of secondary alcohols.

Reglospecific steroselective conversion of ribonucleosides to 2'-deoxynucleosides", *J. Amer. Chem. Soc.*, 105 (1983), pp. 4059-4065.

Robins, et al., "Potential purine antagonists. I. Synthesis of some 4, 6-substituted pyrazolo [3,4-d]pyrimidines", *J. Amer. Chem. Soc.*, 78 (1995), pp. 784-790.

Rosemeyer, H., et al., "Stereoelectronic Effects of Modified Purines on the Sugar Conformation of Nucleosides and Fluorescence properties", *Nucleosides & Nucleotides*, 16 (5&6), (1997), pp. 831-828.

Sala, M., et al., "Ambiguous base pairing of the purine analogue 1-(2-deoxy-beta-D-ribofuranosyl)-imidazole-4-carboxamide during PCR", *Nucleic Acids Research*, 24 (17), (1996), pp. 3302-3306.

Rambrook, et al., "Bacteriophage T4 RNA ligase (Bacteriophage T4-infected *E. coli*)", *In: Molecular Cloning: A Laboratory Manual 2nd Edition*, Cold Spring Harbor Laboratory Press, (1989), pp. 5.66-5.69.

Schena, M., et al., "Parallel human gemone analysis: Microarray-based expression", *PNAS*, 93, (1996), 10614-10619.

Seela, F., et al., "131.8-Aza-7-deaza-2'-deoxyguanosine: Phosphoramidite Synthesis and Properties of Octanucleotides", *Helvetica Chimica ACta*, 71, (1988), pp. 1191-1198.

Seela, F., et al., "193. 8-Aza-7 deazaadenine N8- and N9- (Beta-D-2'-Deoxyribofuranosides): Building Blocks for Automated DNA Synthesis and Properties of Oligodeoxyribonucleotides", *Helvetica Chemica Acta*, 71, (1988), pp. 1813-1823.

Seela, F., et al., "Alternating d(G-C)3 and d(C-G)3 hexanucleotides containing 7-deaza-2'deoxyguanosine of 8-aza-7-deaza-2'-deoxyguanosine in place of dG" *Nucleic Acids Research*, 17 (3), (1989), pp. 901-910.

Seela, F., et al., "Synthesis of 7-alkynlated 8-aza-7-deaza-2'-deoxyadenosines via the Pd-catalysed cross-coupling reaction", *J. Chem. Soc., Perkin Trans.*, 1 (1998), pp. 3233-3239.

Seela, F., et al., "Sythesis of oligonucleotides containing pyrazolo[3,4-d]pyrimidines: The influence of 7-substituted 8-aza-7-deazaadenines on the duplex structure and stability", *J. Chem. Soc., Perkin Trans.*, 1, (1999), pp. 479-488.

Southern, et al., "Analyzing and comparing nucleic acid sequences by hybridization", *Genomics 1*, (1992), 1008-1017.

Southern, E.M., et al., "Arrays of complementary oligonucleotides for analyzing the . . . ", *Nucleic Acids Research*, 22 (8), (1994), 1368-1373.

Stille, J.K., et al., "Stereospecific Palladium-Catalyzed Coupling Reactions of Vinyl iodides with Acetylenic Tin Reagents", *Journal of the American Chemical Society*, 109 (7), (Apr. 1, 1987), pp. 2138-2152.

Stimpson, D.I., et al., "Real-Time Detection of DNA Hybridization and Melting on oligonucleotide arrays by using optical wave guides", *PNAS*, 92, (1995), 6379-6383.

Tanji, K., et al., "Studies on Pyrimidine Derivatives. XXVII. Synthesis of 2- and 4- Pyrimidinyl Ketones by Means of the Hydration of Alkynylprimidines", *Chemical & Pharmaceutical Bulletin*, 30 (5), (May 1982), pp. 1865-1867.

Theisen, P., et al., "Fluorescent Dye Phosphoramidite Labeling of Oligonucleotides", *Nucleic Acids Symposium Series*, 27 (1992), pp. 99-102.

Uhlenbeck, et al., "T4 RNA ligase", *In: The Enzymes, XV, Nucleic Acids, Part B*, Boyer, P.D., (Ed.), Academic Press, (1982), pp. 31-58.

Wages, J.M., et al., "High-Performance Liquid Chromatography Analysis of PCR Products", *In: PCR Strategies, Chapter 11*, Academic Press, Inc., (1995), pp. 140-153.

Wang, et al., "Large-scale identification, mapping, and genotyping of single-nucleotide polymorphisms in the human genome", *Science*, 280, (1998), pp. 1077-1082.

Wojczewski, C., et al., "Synthesis and Application of 3'- Amino-Dye-Terminators for DNA Sequencing", *Nucleosides & Nucleotides*, 16 (5-6), (1997), pp. 751-754.

Wu, et al., "The Ligation amplification reaction (LAR)—Amplification of specific DNA sequences using sequential rounds of template-dependent ligation", *Genomics*, 4, (1989), pp. 560-569.

Yu, et al., "Cyanine dye dUTP analogs for enzymatic labeling of DNA probes", *Nucleic Acids Research*, 22, (1994), pp. 3226-3232.

Zhu, Z., et al., "Directly labeled DNA probes using Fluorescent nucleotides with different length linkers", *Nucleic Acids Research*, 22 (16), (1994), pp. 3418-3422.

\* cited by examiner

N1-labeled 3-(β-D-ribofuranosyl)-1H-pyrazalo-[4,3-d]pyrimidine 5'-triphosphate

N1-labeled 5-(β-D-ribofuranosyl)-2,4[1H,3H]-pyrimidinedione 5'-triphosphate

42a M-Q = CO(CH₂)₅NH-(6)-fluorescein
42b M-Q = CO(CH₂)₅NH-biotin

N-labeled
2,5-anhydro-3-deoxy-D-ribo-hexamide
6-triphosphate

45a Q= 5-carboxyfluorescein
45b Q= biotin

Imidazole

*as*-triazine-3,5[2H,4H]-dione
("5-aza-pyrimidine") nucleotides.

U/T analogs

C/dC analogs nitro-indole/indazole nitro-pyrrole/pyrazole (X = N or CH₂)

pyrazolo[3,4-d]pyrimidine
("9-aza-7-deazapurine") nucleotides

A/dA analogs

G/dG analogs

X = O, NH, or $CH_2$

X = O, S base = heterocyclic moiety (e.g., analogs thereof);

∿∿∿ = linker

LABEL = detectable signal-gene

X = O, S, CH$_2$

Y = O, S

X = O, S, CH$_2$
Y = O, S

L = label
TP = triphosphate
B = base
∿∿∿ = linker

HIV array data for analog 42a (*T7* labeling of RNA target)

accuracy of correct calls for analog is equivalent to the control

HPLC incorporation efficiency of C-nucleotide 42a (T7 RNA pol, 1 kb transcript)

NUCLEIC ACID LABELING COMPOUNDS

RELATED APPLICATIONS

This application is a continuation-in-part of U.S. application Ser. No. 10/314,012, filed Dec. 5, 2002, now U.S. Pat. No. 6,864,059 which is a continuation-in-part of U.S. application Ser. No. 10/097,113, filed Mar. 12, 2002, which is a continuation-in-part of U.S. application Ser. No. 09/952, 387, filed Sep. 11, 2001, now U.S. Pat. No. 6,965,020, which is a continuation-in-part of U.S. application Ser. No. 09/780, 574, filed Feb. 9, 2001, now U.S. Pat. No. 6,596,856, which is a continuation-in-part of U.S. application Ser. No. 09/126, 645, filed Jul. 31, 1998, abandoned, which is a continuation-in-part of U.S. Ser. No. 08/882,649, filed Jun. 25, 1997, now U.S. Pat. No. 6,344,316 which is a continuation of PCT/US97/01603, filed on Jan. 22, 1997 designating the United States of America, which claims priority to U.S. Provisional Application No. 60/010,471 filed on Jan. 23, 1996 and U.S. Provisional Application No. 60/035,170, filed on Jan. 9, 1997, all of which are herein incorporated by reference.

STATEMENT OF RIGHTS TO INVENTIONS MADE UNDER FEDERALLY SPONSORED RESEARCH

This invention was made with Government support under contract 70NANB5H1031 awarded by the Advanced Technology Program of the National Institute of Standards and Technology. The Government has certain rights in this invention.

BACKGROUND OF THE INVENTION

Gene expression in diseased and healthy individuals is oftentimes different and characterizable. The ability to monitor gene expression in such cases provides medical professionals with a powerful diagnostic tool. This form of diagnosis is especially important in the area of oncology, where it is thought that the overexpression of an oncogene, or the underexpression of a tumor suppressor gene, results in tumorogenesis. See Mikkelson et al. *J. Cell. Biochem.* 1991, 46, 3-8.

One can indirectly monitor gene expression, for example, by measuring nucleic acid (e.g., mRNA) that is the transcription product of a targeted gene. The nucleic acid is chemically or biochemically labeled with a detectable moiety and allowed to hybridize with a localized nucleic acid of known sequence sometimes, know here as a probe. The detection of a labeled nucleic acid at the probe position indicates that the targeted gene has been expressed. See International Application Publication Nos.WO 97/27317, WO 92/10588 and WO 97/10365.

The labeling of a nucleic acid is typically performed by covalently attaching a detectable group (label) to either an internal or terminal position. Scientists have reported a number of detectable nucleotide analogues that have been enzymatically incorporated into an oligo- or polynucleotide. Langer et al., for example, disclosed analogues of dUTP and UTP that contain a covalently bound biotin moiety. *Proc. Natl. Acad. Sci. USA* 1981, 78, 6633-6637. The analogues, shown below, possess an allylamine linker arm that is attached to the C-5 position of the pyrimidine ring at one end and a biotin moiety at the other. The dUTP and UTP analogues, wherein R is H or OH, were incorporated into a polynucleotide.

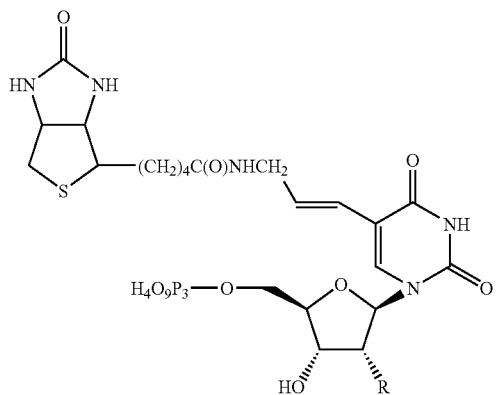

Petrie et al. disclosed a dATP analogue, 3-[5-[(N-biotinyl-6-aminocaproyl)-amino]pentyl]-1-(2-deoxy-β-D-erythro-pentofuranosyl)-1H-pyrazolo[3,4-d]pyrimidin-4-amine-5'-triphosphate. *Bioconjugate Chem.* 1991, 2, 441-446. The analogue, shown below, is modified at the 3-position with a linker arm that is attached to a biotin moiety. Petrie et al. reported that the compound wherein R is biotin is incorporated into DNA by nick translation.

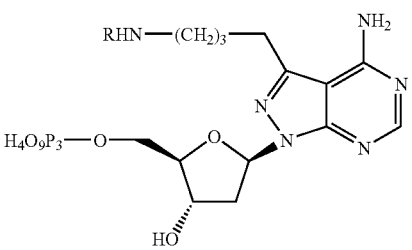

Prober et al. disclosed a set of four dideoxynucleotides, each containing a succinylfluorescein dye. *Science* 1987, 238, 336-341. The dideoxynucleotides, one of which is shown below, were enzymatically incorporated into an oligonucleotide through a template directed extension of a primer. The compounds provided for a DNA sequencing method based on gel migration.

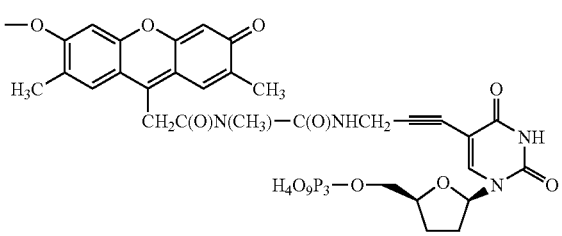

Herrlein et al. disclosed modified nucleoside trisphosphates of the four DNA bases. *Helv. Chim. Acta* 1994, 77, 586-596. The compounds, one of which is shown below, contain a 3'-amino group containing radioactive or fluorescent moieties. Herrlein et al. further described the use of the nucleoside analogues as DNA chain terminators.

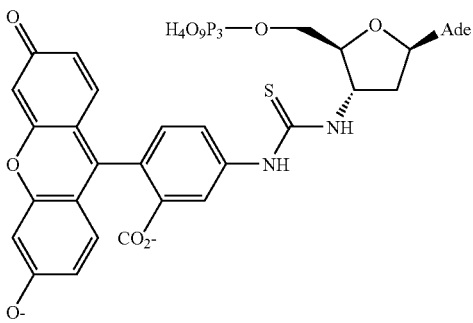

Cech et al. disclosed 3'-amino-functionalized nucleoside triphosphates. *Collect. Czech. Chem. Commun.* 1996, 61, S297-S300. The compounds, one of which is shown below, contain a fluorescein attached to the 3'-position through an amino linker. Cech et al. proposed that the described functionalized nucleosides would be useful as terminators for DNA sequencing.

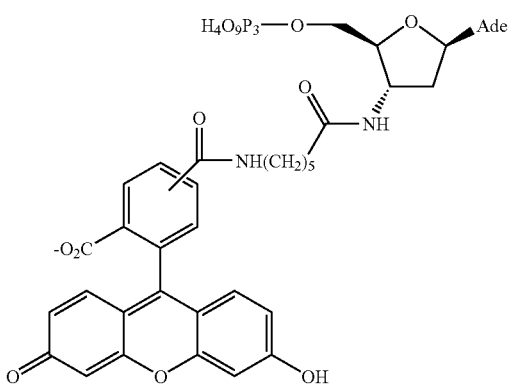

SUMMARY OF THE INVENTION

The present invention relates to nucleic acid labeling compounds. More specifically, the invention provides heterocyclic derivatives containing a detectable moiety. It further provides methods of attaching the heterocyclic derivatives to a nucleic acid.

The present invention provides nucleic acid labeling compounds that are capable of being enzymatically incorporated into a nucleic acid. The nucleic acids to which the compounds are attached substantially maintain their ability to bind to a complementary nucleic acid sequence.

DISCLOSURE OF THE INVENTION

The present invention relates to nucleic acid labeling compounds. More specifically, the invention provides heterocyclic derivatives containing a detectable moiety. The invention also provides methods of making such heterocyclic derivatives. It further provides methods of attaching the heterocyclic derivatives to a nucleic acid.

The development of a novel nucleic acid labeling compound that is effectively incorporated into a nucleic acid to provide a readily detectable composition would benefit genetic analysis technologies. It would aid, for example, in the monitoring of gene expression and the detection and screening of mutations and polymorphisms. Such a compound should be suitable for incorporation into a nucleic acid either by enzymatic or other means. Furthermore, the nucleic acid to which the labeling compound is attached should maintain its ability to bind to a probe, such as a complementary nucleic acid.

The present invention provides nucleic acid labeling compounds that are capable of being enzymatically incorporated into a nucleic acid. The nucleic acids to which the compounds are attached substantially maintain their ability to bind to a complementary nucleic acid sequence.

One aspect of the instantly disclosed invention are nucleic acid labeling compounds of the following structure:

wherein A is hydrogen or a functional group that permits the attachment of the nucleic acid labeling compound to a nucleic acid; T is a template moiety; $H_c$ is a heterocyclic group, includuding without limitation a base such as A, T, G, C, and U; L is a linker moiety; Q is a detectable moiety; and M is a connecting group, wherein m is an integer ranging from 0 to about 5. Thus, the connecting group may optionally not be present, depending on, inter alia the nature of L and Q.

In one embodiment, the nucleic acid labeling compounds have the following structures:

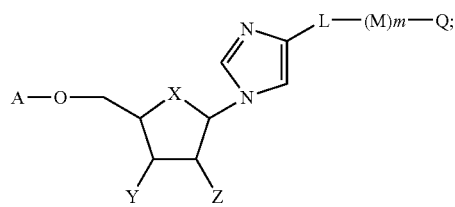

The invention also contemplates steroisomers two of which are shown below by way of example:

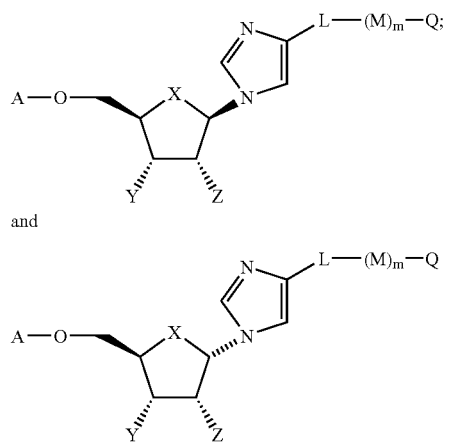

In the above molecules, A is H or a functional group that permits the attachment of the nucleic acid labeling compound to a nucleic acid by either enzymatic or, e.g., by chemical means;

X is O, S, $NR_1$ or $CHR_2$, wherein $R_1$ and $R_2$ are, independently, H, alkyl or aryl; Y is H, $N_3$, F, $OR_9$, $SR_9$ or $NHR_9$, wherein $R_9$ is H, alkyl or aryl; Z is H, $N_3$, F or $OR_{10}$, wherein $R_{10}$ is H, alkyl or aryl; L is a linker group, preferably an amido alkyl; Q is a detectable moiety; and, M is a connecting group, wherein m is an integer ranging from 0 to about 3.

In another embodiment, A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —C(O)NH(CH$_2$)$_n$NH—, wherein n is an integer ranging from about 2 to about 10; Q is biotin or a carboxyfluorescein; and, M is —CO(CH$_2$)$_5$NH—, wherein m is 1 or 0.

In another embodiment, Y is H or OH; Z is H or OH; L is —C(O)NH(CH$_2$)$_4$NH—; Q is biotin; and, M is —CO(CH$_2$)$_5$NH, wherein m is 1.

In another embodiment, Y is H or OH; Z is H or OH; L is —C(O)NH(CH$_2$)$_4$NH—; Q is 5-carboxyfluorescein; and, m is 0.

In one embodiment, the nucleic acid labeling compounds have the following structures:

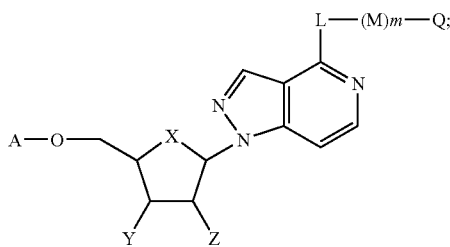

The present invention includes stereoisomers of the above compound, two of which are shown below by example.

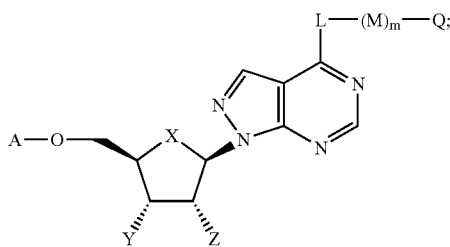

and

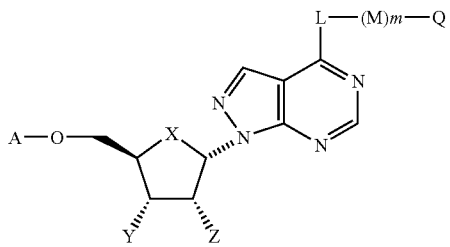

With respect to these disclosed compounds, A is H or a functional group that permits the attachment of the nucleic acid labeling compound to a nucleic acid; X is O, S, NR$_1$ or CHR$_2$, wherein R$_1$ and R$_2$ are, independently, H, alkyl or aryl; Y is H, N$_3$, F, OR$_9$, SR$_9$ or NHR$_9$, wherein R$_9$ is H, alkyl or aryl; Z is H, N$_3$, F or OR$_{10}$, wherein R$_{10}$ is H, alkyl or aryl; L is a linking group, preferably amino alkyl; Q is a detectable moiety; and, M is a connecting group, wherein m is an integer ranging from 0 about 3.

In another embodiment, A is H or $H_4O_9P_3$—; X is O; Y is H or OR$_9$, wherein R$_9$ is H, alkyl or aryl; Z is H, N$_3$, F or OR$_{10}$, wherein R$_{10}$ is H, alkyl or aryl; L is —NH(CH$_2$)$_n$NH—, wherein n is an integer ranging from about 2 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

In another embodiment, Y is H or OH; Z is H or OH; L is —NH(CH$_2$)$_4$NH—; Q is biotin; and, m is 0.

In another embodiment, Y is H or OH; Z is H or OH; L is —NH(CH$_2$)$_4$NH—; Q is 5carboxyfluorescein; and, m is 0.

In one embodiment, the nucleic acid labeling compounds have the following structure:

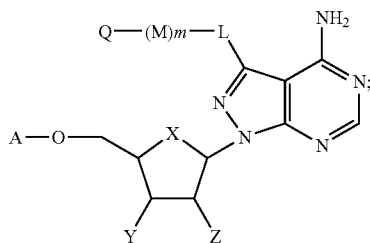

The present invention includes stereoisomers, two examples of which are shown below:

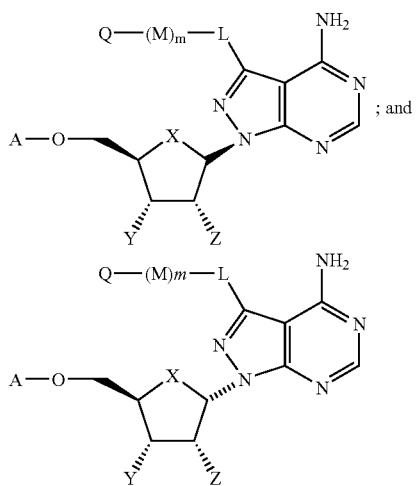

In these compounds, A is H or a functional group that permits the attachment of the nucleic acid labeling compound to a nucleic acid; X is O, S, NR$_1$ or CHR$_2$, wherein R$_1$ and R$_2$ are, independently, H, alkyl or aryl; Y is H, N$_3$, F, OR$_9$, SR$_9$ or NHR$_9$, wherein R$_9$ is H, alkyl or aryl; Z is H, N$_3$, F or OR$_{10}$, wherein R$_{10}$ is H, alkyl or aryl; L is a linker moiety, preferably alkynyl alkyl; Q is a detectable moiety; and, M is a connecting group, wherein m is an integer ranging from 0 to about 3.

In another embodiment, A is H or $H_4O_9P_3$—; X is O; Y is H or OR$_9$, wherein R$_9$ is H, alkyl or aryl; Z is H, N$_3$, F or OR$_{10}$, wherein R$_{10}$ is H, alkyl or aryl; L is —C≡C(CH$_2$)$_n$NH—, wherein n is an integer ranging from about 1 to about 10; Q is biotin or carboxyfluorescein; and, M is —CO(CH$_2$)$_5$NH—, wherein m is 1 or 0.

In another embodiment, Y is H or OH; Z is H or OH; L is —C≡CCH$_2$NH—; Q is biotin; and, m is 1.

In another embodiment, Y is H or OH; Z is H or OH; L is —C≡CCH$_2$NH—; Q is 5carboxyfluorescein; and, m is 1.

In another embodiment L is selected from the group consisting of —CH═CH—C(O)— and —CH═CH—(CH₂)ₙNH— where n is an interger from 1 to about 5

In one embodiment, the nucleic acid labeling compounds have the following structures:

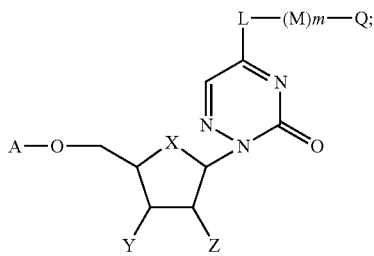

Stereoisomers are also included within the scope of the invention, examples of two of which are shown below:

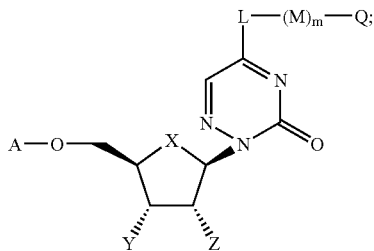

and

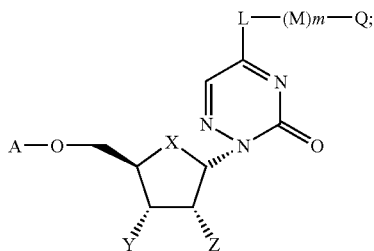

wherein A is H or a functional group that permits the attachment of the nucleic acid labeling compound to a nucleic acid; X is O, S, NR₁ or CHR₂, wherein R₁ and R₂ are, independently, H, alkyl or aryl; Y is H, N₃, F, OR₉, SR₉ or NHR₉, wherein R₉ is H, alkyl or aryl; Z is H, N₃, F or OR₁₀, wherein R₁₀ is H, alkyl or aryl; L is linker group, preferably an amino alkyl; Q is a detectable moiety; and, M is a connecting group, wherein m is an integer ranging from 0 to about 3.

In another embodiment, A is H or H₄O₉P₃—; X is O; Y is H or OR₉, wherein R₉ is H, alkyl or aryl; Z is H, N₃, F or OR₁₀, wherein R₁₀ is H, alkyl or aryl; L is —NH(CH₂)ₙNH—, wherein n is an integer ranging from about 2 to about 10; Q is biotin or carboxyfluorescein; and, M is —CO(CH₂)₅NH— or —CO(CH₂)₅NHCO(CH₂)₅NH—, wherein m is 1 or 0.

In another embodiment, Y is H or OH; Z is H or OH; L is —NH(CH₂)₄NH—; Q is biotin; and, M is —CO(CH₂)₅NH—, wherein m is 1.

In another embodiment, Y is H or OH; Z is H or OH; L is —NH(CH₂)₄NH—; Q is 5-carboxyfluorescein; and, M is —CO(CH₂)₅NH—, wherein m is 1.

In one embodiment, the nucleic acid labeling compounds have the following structures:

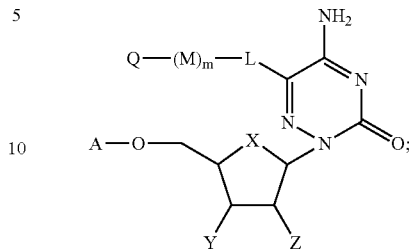

Stereoisomers are also included within the scope of the invention, examples of two of which are shown below:

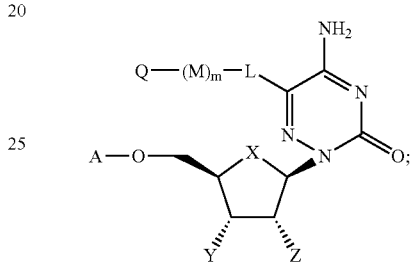

and

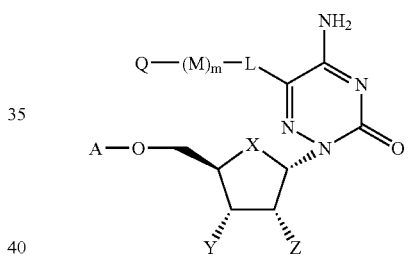

wherein A is H or a functional group that permits the attachment of the nucleic acid labeling compound to a nucleic acid; X is O, S, NR₁ or CHR₂, wherein R₁ and R₂ are, independently, H, alkyl or aryl; Y is H, N₃, F, OR₉, SR₉ or NHR₉, wherein R₉ is H, alkyl or aryl; Z is H, N₃, F or OR₁₀, wherein R₁₀ is H, alkyl or aryl; L is a linker group, preferably a functionalized alkyl, alkenyl alkyl or alkynyl alkyl; Q is a detectable moiety; and, M is a connecting group, wherein m is an integer ranging from 0 to about 3.

In another embodiment, A is H or H₄O₉P₃—; X is O; Y is H or OR₉, wherein R₉ is H, alkyl or aryl; Z is H, N₃, F or OR₁₀, wherein R₁₀ is H, alkyl or aryl; L is —CH═CH (CH₂)ₙ NH—, wherein n is an integer ranging from about 1 to about 10; Q is biotin or carboxyfluorescein; and, M is —CO(CH₂)₅NH— or —CO(CH₂)₅NHCO(CH₂)₅NH—, wherein m is 1 or 2.

In another embodiment, Y is H or OH; Z is H or OH; L is —CH═CHCH₂NH—; Q is biotin; and, m is 0.

In another embodiment, Y is H or OH; Z is H or OH; L is —CH═CHCH₂NH—; Q is 5-carboxyfluorescein; and, m is 0.

In one embodiment, the nucleic acid labeling compounds have the following structures:

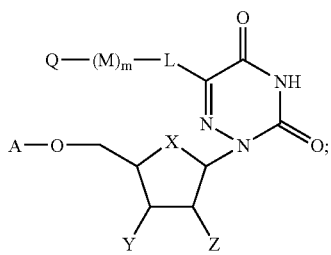

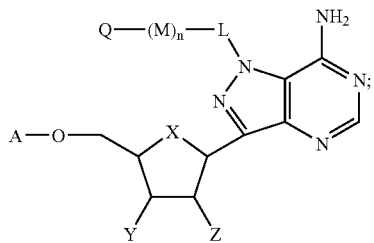

Stereoisomers are also included within the scope of the invention, examples of two of which are shown below:

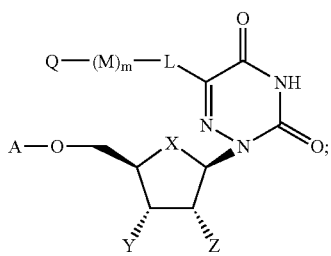

and

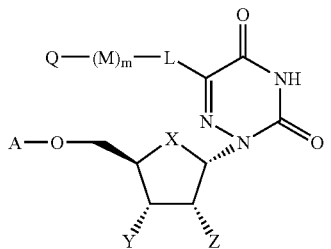

wherein A is H or a functional group that permits the attachment of the nucleic acid labeling compound to a nucleic acid; X is O, S, NR$_1$ or CHR$_2$, wherein R$_1$ and R$_2$ are, independently, H, alkyl or aryl; Y is H, N$_3$, F, OR$_9$, SR$_9$ or NHR$_9$, wherein R$_9$ is H, alkyl or aryl; Z is H, N$_3$, F or OR$_{10}$, wherein R$_{10}$ is H, alkyl or aryl; L is a linker group, preferably a functionalized alkyl, alkenyl alkyl or alkynyl alkyl; Q is a detectable moiety; and, M is a connecting group, wherein m is an integer ranging from 0 to about 3.

In another embodiment, A is H or H$_4$O$_9$P$_3$—; X is O; Y is H or OR$_9$, wherein R$_9$ is H, alkyl or aryl; Z is H, N$_3$, F or OR$_{10}$, wherein R$_{10}$ is H, alkyl or aryl; L is a linker group, preferably —CH=CH(CH$_2$)$_n$NH—, wherein n is an integer ranging from about 1 to about 10; Q is biotin or carboxyfluorescein; and, M is —CO(CH$_2$)$_5$NH— or —CO(CH$_2$)$_5$NHCO(CH$_2$)$_5$NH—, wherein m is 1.

In another embodiment, Y is H or OH; Z is H or OH; L is —CH=CHCH$_2$NH—; Q is biotin; and, m is 0.

In another embodiment, Y is H or OH; Z is H or OH; L is —CH=CHCH$_2$NH—; Q is 5-carboxyfluorescein; and, m is 0.

In one embodiment, the nucleic acid labeling compounds have the following structures:

Stereoisomers are also included within the scope of the invention, examples of two of which are shown below:

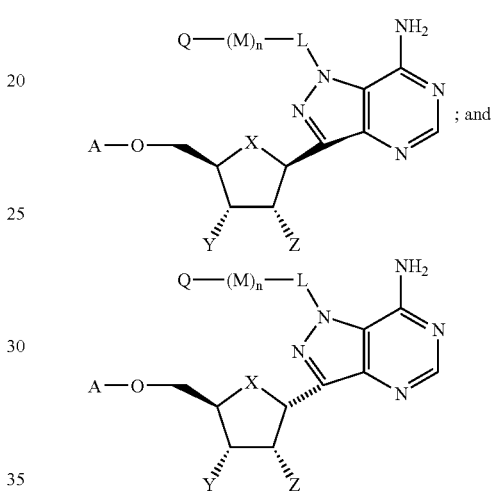

wherein A is H or a functional group that permits the attachment of the nucleic acid labeling compound to a nucleic acid; X is O, S, NR$_1$ or CHR$_2$, wherein R$_1$ and R$_2$ are, independently, H, alkyl or aryl; Y is H, N$_3$, F, OR$_9$, SR$_9$ or NHR$_9$, wherein R$_9$ is H, alkyl or aryl; Z is H, N$_3$, F or OR$_{10}$, wherein R$_{10}$ is H, alkyl or aryl; L is linker group, preferably functionalized alkyl; Q is a detectable moiety; and, M is a connecting group, wherein m is an integer ranging from 0 to about 3.

In another embodiment, A is H or H$_4$O$_9$P$_3$—; X is O; Y is H or OR$_9$, wherein R$_9$ is H, alkyl or aryl; Z is H, N$_3$, F or OR$_{10}$, wherein R$_{10}$ is H, alkyl or aryl; L is —(CH$_2$)$_n$C(O)—, wherein n is an integer ranging from about 1 to about 10; Q is biotin or fluorescein; and, M is —NH(CH$_2$CH$_2$O)$_k$NH— or, more preferably, —NH(CH$_2$CH$_2$O)$_k$CH$_2$CH$_2$NH—, wherein, k is an integer from 1 to about 5, wherein m is 1 and k is preferably 1.

In another embodiment, Y is H or OH; Z is H or OH; L is —CH$_2$—C(O)—; Q is a carboxyfluorescein or biotin; and M is —NH(CH$_2$CH$_2$O)$_k$NH— or, more preferably —NH(CH$_2$CH$_2$O)$_k$CH$_2$CH$_2$NH—, wherein, k is 2 and m is 1.

In another embodiment, Y is OH; Z is OH; L is —CH$_2$—C(O)—; Q is biotin; and M is —NH(CH$_2$CH$_2$O)$_k$NH— or more preferably —NH(CH$_2$CH$_2$O)$_k$CH$_2$CH$_2$NH—, wherein, k is 2 and m is 1.

In another embodiment,; L is —CH=CHCH$_2$NH—; Q is a carboxyfluorescein; and M is —NH(CH$_2$CH$_2$O)$_k$NH— or more preferably —NH(CH$_2$CH$_2$O)$_k$CH$_2$CH$_2$NH—, wherein, k is 2 and m is 1.

In one embodiment, the nucleic acid labeling compounds have the following structures:

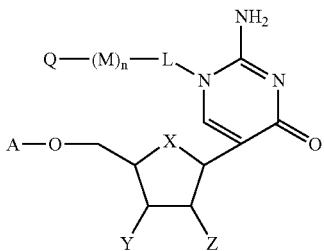

Stereoisomers are also included within the scope of the invention, examples of two of which are shown below:

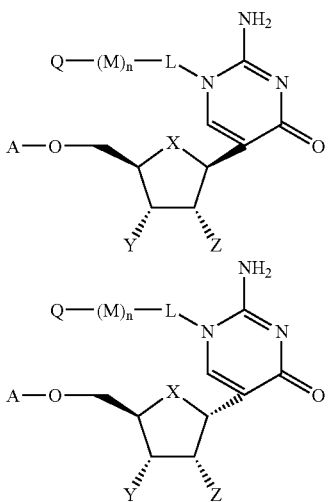

wherein A is H or a functional group that permits the attachment of the nucleic acid labeling compound to a nucleic acid; X is O, S, $NR_1$ or $CHR_2$, wherein $R_1$ and $R_2$ are, independently, H, alkyl or aryl; Y is H, $N_3$, F, $OR_9$, $SR_9$ or $NHR_9$, wherein $R_9$ is H, alkyl or aryl; Z is H, $N_3$, F or $OR_{10}$, wherein $R_{10}$ is H, alkyl or aryl; L is linker group; Q is a detectable moiety; and, M is a connecting group, wherein m is an integer ranging from 0 to about 3.

In another embodiment, A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —$(CH_2)_nC(O)$—, wherein n is an integer ranging from about 1 to about 10; Q is biotin or a fluorescein; and, a first M is —$NH(CH_2)_nNH$—, wherein n is an integer from about 2 to about 10, and a second M is —$CO(CH_2)_5NH$—, wherein m is 2.

In another embodiment, Y is H or OH; Z is H or OH; L is —$(CH_2)_2C(O)$—, Q is biotin or a carboxyfluorescein; and a first M is —$NH(CH_2)_2NH$—, and a second M is —$CO(CH_2)_5NH$—, wherein m is 2.

In another embodiment, Y is OH; Z is OH; L is —$(CH_2)_2C(O)$—, Q is a carboxyfluorescein; and, a first M is —$NH(CH_2)_2NH$—, and a second M is —$CO(CH_2)_5NH$—, wherein m is 2.

In another embodiment, Y is OH; Z is OH; L is —$(CH_2)_2C(O)$—, Q is biotin; and, a first M is —$NH(CH_2)_2NH$—, and a second M is —$CO(CH_2)_5NH$—, wherein m is 2.

In another embodiment, wherein A is a functional group the permits the attachment of the nucleic acid labeling compound to a nucleic acid, preferably A is a triphosphate group with appropriate counterions. The counterions are selected from the group consisting of H+, Na+, Li+, K+, and $NH_4$+; X is O; Y is OH; Z is OH; L is selected from the group consisting of —CH=CH—C(O)—NH—$CH_2$—$CH_2$—NH—C(O)— and —$CH_2$—$CH_2$—C(O)—NH—$CH_2$—$CH_2$—NH—C(O); M is —$(CH_2)_5$—NH— and Q is biotin having the structure:

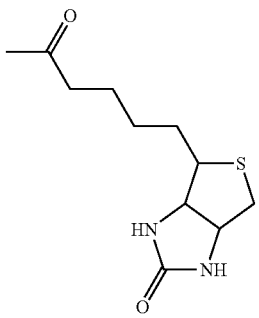

In another embodiment, A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is selected from the group consisting of —CH=CH—C(O)— and —CH=CH—CH($NH_2$)—; Q is biotin or a fluorescein; and, a first M is —$NH(CH_2)_nNH$—, wherein n is an integer from about 2 to about 10, and a second M is —$CO(CH_2)_pNH$—, wherein p is an interger from about two to about 10 and m is 2.

In another embodiment, Y is H or OH; Z is H or OH; L is —CH=CH—C(O)—, Q is biotin or a carboxyfluorescein; and a first M is —$NH(CH_2)_2NH$—, and a second M is —$CO(CH_2)_5NH$—, wherein m is 2.

In another embodiment, Y is OH; Z is OH; L is —CH=CH—C(O)—, Q is a biotin or a carboxyfluorescein; and, a first M is —$NH(CH_2)_2NH$—, and a second M is —$CO(CH_2)_5NH$—, wherein m is 2.

In another embodiment, Y is OH; Z is OH; L is —CH=CH—C(O)—, Q is or biotin; and, a first M is —$NH(CH_2)_2NH$—, and a second M is —$CO(CH_2)_5NH$—, wherein m is 2.

In yet another embodiment L comprises a vinyl group (—CH=CH—) attached at its 1 position directly to the N of the base. In accordance with this aspect of the present invention, where L is vinyl, further substituents may be attached to the 2 position of the vinyl groups such as for example $R_{11}$(—CH=CH—$R_{11}$). Preferably $R_{11}$ is alkyl, aryl, functionalized alkyl, amido alkyl, alkenyl alkyl, alkoxy, thio and amino alkyl. Most preferablbly $R_{11}$ is $C(O)R_{12}$ where $R_{12}$ is a bond, aryl, functionalized alkyl, amido alkyl, alkenyl alkyl alkoxy, thio and amino alkyl.

Importantly, as disclosed in accordance with one aspect of the present invention, the linker group L is selected to provide a linking function, which either alone or in conjunction with appropriate connecting group (M), provide appropriate spacing of the Q group from the Hc or base group at such a length and in such a configuration as to allow an appropriate assay to be performed on the Q group, but at the same time substantially preserving the ability of the nucleic acid labeling compound to act as a substrate for the appropriate enzyme, e.g., terminal transferase and/or RNA polymerase. Those of skill in the art will also appreciate that the Hc-L-(M)m-Q groups must be chosen, in accordance with the present invention, to avoid subtantially inhibiting the ability of a nucleic acid strand incorporating such group to undergo Watson-Crick type base pairing with complementary sequences. Thus, -L-(M)m-Q may be any arrangements or grouping of molecules or atoms which functions to allow nucleic acids to be labeled and detected.

In accordance with one aspect of the present invention, $R_p$ is preferably a bond, Y is OH; Z is OH; L is —(CH$_2$)$_2$C(O)—, and Q is selected from the group consisting of a fluorescein and a biotin; and a first M is —NH(CH$_2$)$_2$NH—, and a second M is —CO(CH$_2$)$_5$NH—, wherein m is 2.

In one embodiment, the nucleic acid labeling compounds have the following structures:

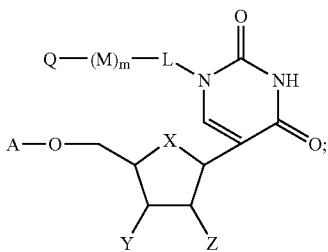

Stereoisomers are also included within the scope of the invention, examples of two of which are shown below:

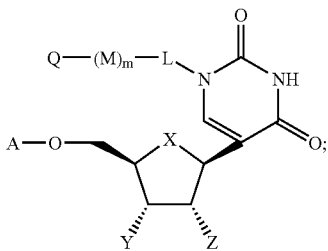

and

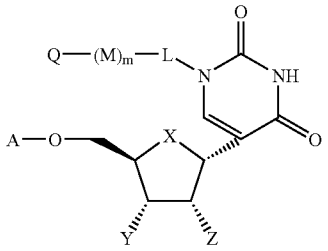

wherein A is H or a functional group that permits the attachment of the nucleic acid labeling compound to a nucleic acid; X is O, S, NR$_1$ or CHR$_2$, wherein R$_1$ and R$_2$ are, independently, H, alkyl or aryl; Y is H, N$_3$, F, OR$_9$, SR$_9$ or NHR$_9$, wherein R$_9$ is H, alkyl or aryl; Z is H, N$_3$, F or OR$_{10}$, wherein R$_{10}$ is H, alkyl or aryl; L is functionalized alkyl; Q is a detectable moiety; and, M is a connecting group, wherein m is an integer ranging from 0 to about 3.

In another embodiment, A is H or H$_4$O$_9$P$_3$—; X is O; Y is H or OR$_9$, wherein R$_9$ is H, alkyl or aryl; Z is H, N$_3$, F or OR$_{10}$, wherein R$_{10}$ is H, alkyl or aryl; ; L is —(CH$_2$)$_n$C(O)—, wherein n is an integer ranging from about 1 to about 10; Q is biotin or a fluorescein; and, a first M is —NH(CH$_2$)$_n$NH—, wherein n is an integer from about 2 to about 10, and a second M is —CO(CH$_2$)$_5$NH—, wherein m is 2.

In another embodiment, Y is H or OH; Z is H or OH; L is —(CH$_2$)$_2$C(O)—, Q is biotin or a carboxyfluorescein; and a first M is —NH(CH$_2$)$_2$NH—, and a second M is —CO(CH$_2$)$_5$NH—, wherein m is 2.

In another embodiment, Y is OH; Z is OH; L is —(CH$_2$)$_2$C(O)—, Q is a carboxyfluorescein; and, a first M is —NH(CH$_2$)$_2$NH—, and a second M is —CO(CH$_2$)$_5$NH—, wherein m is 2.

In another embodiment, Y is OH; Z is OH; L is —(CH$_2$)$_2$C(O)—, Q is biotin; and, a first M is —NH(CH$_2$)$_2$NH—, and a second M is —CO(CH$_2$)$_5$NH—, wherein m is 2.

In another embodiment, wherein A is a functional group the permits the attachment of the nucleic acid labeling compound to a nucleic acid; preferably, A is a triphosphate group with apporpriate counterions, said counterions selected from the group consisting of H+, Na+, Li+, K+, and NH$_4$+; X is O; Y is OH; Z is OH; L is selected from the group consisting of —CH=CH—C(O)—NH—CH$_2$—CH$_2$—NH—C(O)— and —CH$_2$—CH$_2$—C(O)—NH—CH$_2$—CH$_2$—NH—C(O); M is —(CH$_2$)$_5$—NH— and Q is biotin having the structure:

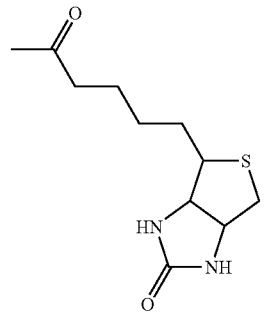

In another embodiment, A is H or H$_4$O$_9$P$_3$—; X is O; Y is H or OR$_9$, wherein R$_9$ is H, alkyl or aryl; Z is H, N$_3$, F or OR$_{10}$, wherein R$_{10}$ is H, alkyl or aryl; L is —CH=CH—C(O)—; Q is biotin or a fluorescein; and, a first M is —NH(CH$_2$)$_n$NH—, wherein n is an integer from about 2 to about 10, and a second M is —CO(CH$_2$)$_p$NH—, wherein p is an interger from about 2 to about 10 and m is 2.

In another embodiment, Y is H or OH; Z is H or OH; L is —CH=CH—C(O)—, Q is biotin or a carboxyfluorescein; and a first M is —NH(CH$_2$)$_2$NH—, and a second M is —CO(CH$_2$)$_5$NH—, wherein m is 2.

In another embodiment, Y is OH; Z is OH; L is —CH=CH—C(O)—, Q is a biotin or a carboxyfluorescein; and, a first M is —NH(CH$_2$)$_2$NH—, and a second M is —CO(CH$_2$)$_5$NH—, wherein m is 2.

In another embodiment, Y is OH; Z is OH; L is —CH=CH—C(O)—, Q is biotin; and, a first M is —NH(CH$_2$)$_2$NH—, and a second M is —CO(CH$_2$)$_5$NH—, wherein m is 2.

In another embodiment L comprises a vinyl group (—CH=CH—) attached at its 1 position directly to the N of the base. In accordance with this aspect of the present invention, where L is vinyl, further substituents are attached to the 2 position of the vinyl groups such as such as for example R$_{11}$(—CH=CH—R$_{11}$). Preferably R$_{11}$ is alkyl, aryl, functionalized alkyl, amido alkyl, alkenyl alkyl, alkoxy, thio and amino alkyl. Most preferablbly R$_{11}$ is C(O)R$_{12}$, where R$_{12}$ is a bond, aryl, functionalized alkyl, amido alkyl, alkenyl alkyl alkoxy, thio and amino alkyl.

Importantly, as disclosed in accordance with one aspect of the present invention, the linker group L is selected to provide a linker function, which either alone or in conjunction with appropriate connecting groups (M), appropriately spaces the Q group from the Hc or base group at such a length and in such a configuration as to allow an appropriate assay to be performed on the Q group, but at the same time substantially preservers the ability of the nucleic acid labeling compound to act as a substrate for the appropriate enzyme, e.g., terminal transferase and/or RNA polymerase. Those of skill in the art will also appreciate that the chosen Hc-L-(M)m-Q groups must be chosen in accordance with the present invention, to avoid subtantially inhibiting the ability of a nucleic acid strand incorporating such group to undergo Watson-Crick type base pairing with complementary sequences. Thus, -L-(M)m-Q may be any arrangements or gourping of molecules or atoms which functions to allow nucleic acids to be labeled and detected.

In accordance with one aspect of the present invention, R$_b$ is preferably a bond, Y is OH; Z is OH; L is —(CH$_2$)$_2$C(O)—, and Q is selected from the group consisting of a fluorescein and a biotin; and a first M is —NH(CH$_2$)$_2$NH—, and a second M is —CO(CH$_2$)$_5$NH—, wherein m is 2.

In one embodiment, the nucleic acid labeling compounds have the following structures:

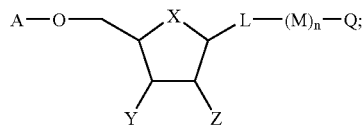

Stereoisomers are also included within the scope of the invention, examples of two of which are shown below:

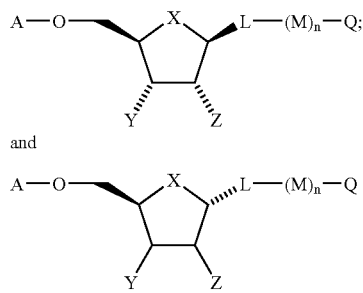

wherein A is H or a functional group that permits the attachment of the nucleic acid labeling compound to a nucleic acid; X is O, S, NR$_1$ or CHR$_2$, wherein R$_1$ and R$_2$ are, independently, H, alkyl or aryl; Y is H, N$_3$, F, OR$_9$, SR$_9$ or NHR$_9$, wherein R$_9$ is H, alkyl or aryl; Z is H, N$_3$, F or OR$_{10}$, wherein R$_{10}$ is H, alkyl or aryl; L is a linking group, preferably amido alkyl; Q is a detectable moiety; and, M is a connecting group, wherein m is an integer ranging from 0 to about 3.

In another embodiment, A is H or H$_4$O$_9$P$_3$—; X is O; Y is H or OR$_9$, wherein R$_9$ is H, alkyl or aryl; Z is H, N$_3$, F or OR$_{10}$, wherein R$_{10}$ is H, alkyl or aryl; ; L is —C(O)NH(CH$_2$)$_n$NH—, wherein n is an integer ranging from about 2 to about 10; Q is biotin or a fluorescein; wherein m is 0, 1, or 2.

In another embodiment, Y is H or OH; Z is H or OH; L is —C(O)NH(CH$_2$)$_4$NH— or, more preferably, —C(O)NH(CH$_2$)$_2$NH—; M is preferably —C(O)(CH$_2$)$_5$NH and Q is biotin or a carboxyfluorescein.

In another embodiment, Y is OH; Z is H; L is —C(O)NH(CH$_2$)$_4$NH— or, more preferably, —C(O)NH(CH$_2$)$_2$NH—; M is preferably —C(O)(CH$_2$)$_5$NH; Q is biotin.

In another embodiment, Y is OH; Z is H; L is —C(O)NH(CH$_2$)$_4$NH— or, more preferably, —C(O)NH(CH$_2$)$_2$NH—; M is preferably —C(O)(CH$_2$)$_5$NH; and Q is a carboxyfluorescein.

In another embodiment, wherein A is a functional group the permits the attachment of the nucleic acid labeling compound to a nucleic acid; preferably, A is a triphosphate group with apporpriate counterions, said counterions selected from the group consisting of H+, Na+, Li+, K+, and NH$_4$+, Y is OH, X is OH, Z is H or OH, L is —C(O)NH(CH$_2$)$_2$NH—, M is —C(O)(CH2)$_5$NH—, n is 1 and Q is biotin, having the structure:

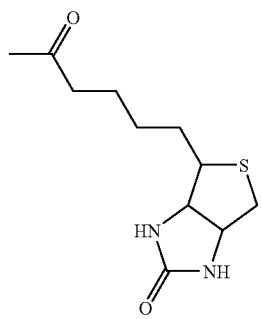

In another embodiment, wherein A is a functional group the permits the attachment of the nucleic acid labeling compound to a nucleic acid; preferably, A is a triphosphate group with apporpriate counterions, said counterions selected from the group consisting of H+, Na+, Li+, K+, and NH$_4$+, Y is OH, X is O, Z is H or OH, L is —C(O)NH(CH$_2$)$_2$NH—, M is —C(O)((CH$_2$)$_2$O)$_4$(CH$_2$)$_2$NH—, n is 1 and Q is biotin, having the structure:

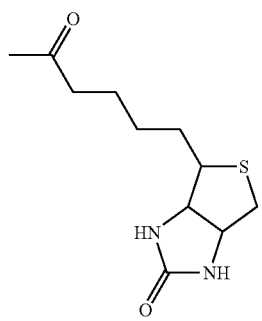

In another aspect of the present invention, a method for preparing a labeled nucleic acid sample is provided having the steps of: providing a nucleic acid sample, the nucleic acid sample comprising DNA; reacting the nucleic acid sample in the presence of the enzyme terminal transferase with the preceding nucleic acid labeling compound. Preferably, according to the instant invention that nucleic acid sample is cDNA.

The present invention also provides nucleic acid derivatives produced by coupling a nucleic acid labeling compound with a nucleic acid and hybridization products comprising the nucleic acid derivatives bound to a complementary probe.

In one embodiment, the nucleic acid labeling compounds used in the coupling have the following structures for example:

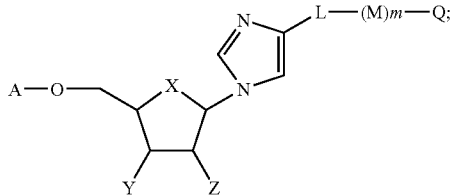

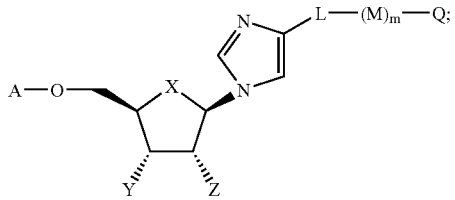

and

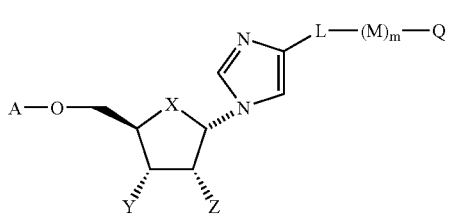

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —C(O)NH(CH$_2$)$_n$NH—, wherein n is an integer ranging from about 2 to about 10; Q is biotin or a carboxyfluorescein; and, M is —CO(CH$_2$)$_5$NH—, wherein m is 1 or 0.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures for example:

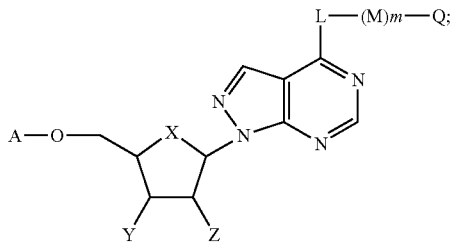

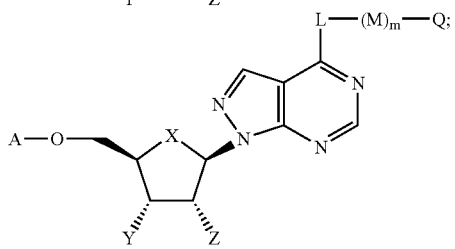

and

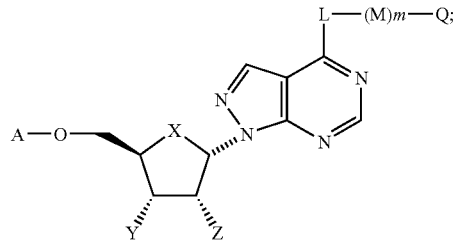

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —NH(CH$_2$)$_n$NH—, wherein n is an integer ranging from about 2 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures for example:

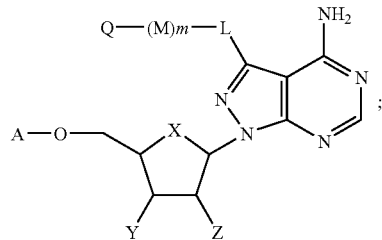

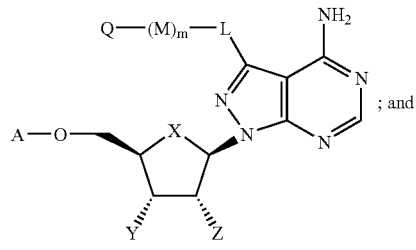

; and

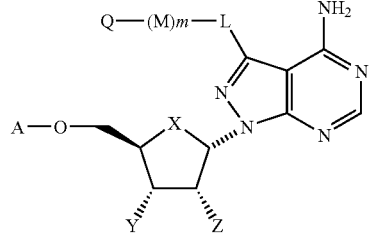

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —C≡C(CH$_2$)$_n$NH—, wherein n is an integer ranging from about 1 to about 10; Q is biotin or carboxyfluorescein; and, M is —CO(CH$_2$)$_5$NH—, wherein m is 1 or 0.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures for example:

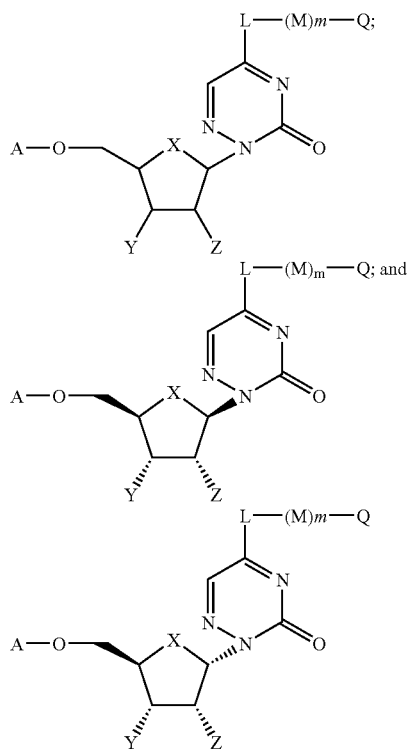

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —NH$(CH_2)_n$NH—, wherein n is an integer ranging from about 2 to about 10; Q is biotin or carboxyfluorescein; and, M is —CO$(CH_2)_5$NH— or —CO$(CH_2)_5$NHCO$(CH_2)_5$NH—, wherein m is 1 or 0.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures for example:

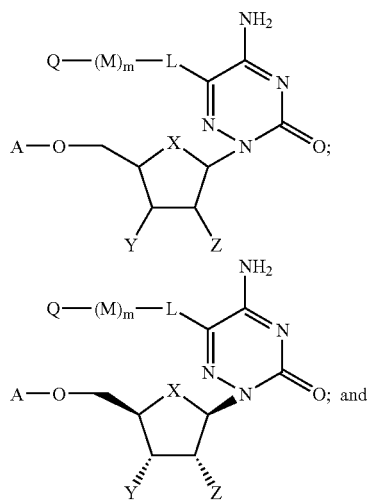

-continued

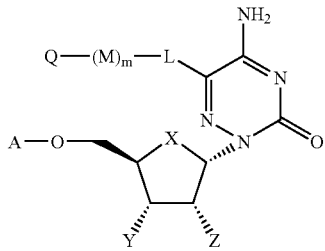

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —CH═CH$(CH_2)_n$NH—, wherein n is an integer ranging from about 1 to about 10; Q is biotin or carboxyfluorescein; and, M is —CO$(CH_2)_5$NH— or —CO$(CH_2)_5$NHCO$(CH_2)_5$NH—, wherein m is 1 or 0.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures for example:

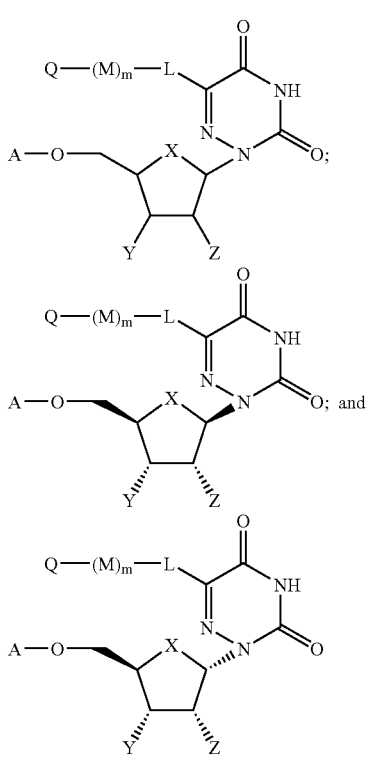

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —CH═CH$(CH_2)_n$NH—, wherein n is an integer ranging from about 1 to about 10; Q is biotin or carboxyfluorescein; and, M is —CO$(CH_2)_5$NH— or —CO$(CH_2)_5$NHCO$(CH_2)_5$NH—, wherein m is 1 or 0.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures for example:

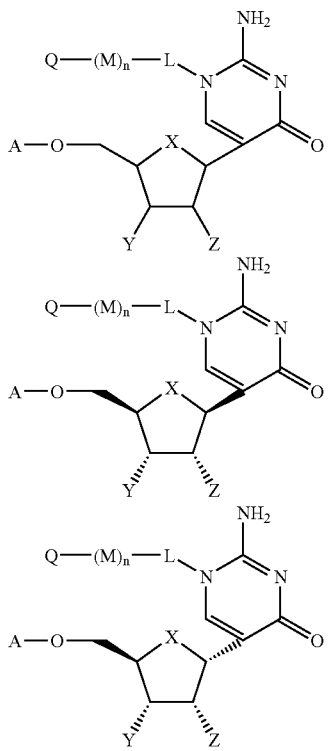

wherein A is H or a functional group that permits the attachment of the nucleic acid labeling compound to a nucleic acid; X is O, S, $NR_1$ or $CHR_2$, wherein $R_1$ and $R_2$ are, independently, H, alkyl or aryl; Y is H, $N_3$, F, $OR_9$, $SR_9$ or $NHR_9$, wherein $R_9$ is H, alkyl or aryl; Z is H, $N_3$, F or $OR_{10}$, wherein $R_{10}$ is H, alkyl or aryl; L is linker group; Q is a detectable moiety; and, M is a connecting group, wherein m is an integer ranging from 0 to about 3.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures for example:

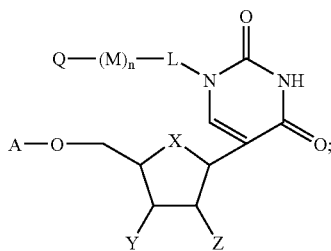

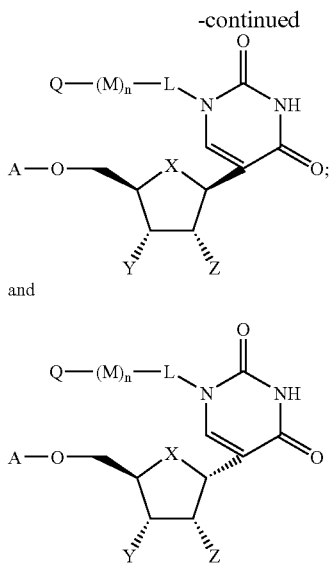

wherein A is H or a functional group that permits the attachment of the nucleic acid labeling compound to a nucleic acid; X is O, S, $NR_1$ or $CHR_2$, wherein $R_1$ and $R_2$ are, independently, H, alkyl or aryl; Y is H, $N_3$, F, $OR_9$, $SR_9$ or $NHR9$, wherein $R_9$ is H, alkyl or aryl; Z is H, $N_3$, F or $OR_{10}$, wherein $R_{10}$ is H, alkyl or aryl; L is functionalized alkyl; Q is a detectable moiety; and, M is a connecting group, wherein m is an integer ranging from 0 to about 3.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures for example:

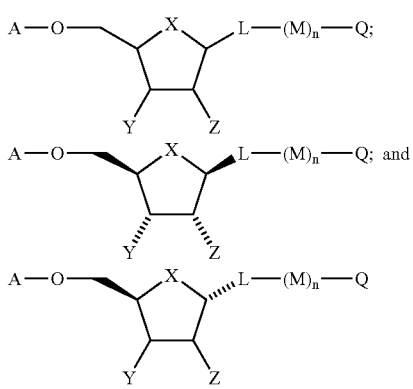

wherein A is H or a functional group that permits the attachment of the nucleic acid labeling compound to a nucleic acid; X is O, S, $NR_1$ or $CHR_2$, wherein $R_1$ and $R_2$ are, independently, H, alkyl or aryl; Y is H, $N_3$, F, $OR_9$, $SR_9$ or $NHR_9$, wherein $R_9$ is H, alkyl or aryl; Z is H, $N_3$, F or $OR_{10}$, wherein $R_{10}$ is H, alkyl or aryl; L is linker group; Q is a detectable moiety; and, M is a connecting group, wherein m is an integer ranging from 0 to about 3.

The hybridization product formed from this nucleic acid derivative comprises the nucleic acid derivative bound to a complementary probe. In one embodiment, the probe is attached to a glass chip.

The present invention also provides methods of synthesizing nucleic acid derivatives by attaching a nucleic acid labeling compound to a nucleic acid. It further provides methods of detecting nucleic acids involving incubating the nucleic acid derivatives with a probe.

In one embodiment, the nucleic acid labeling compounds attached to the nucleic acid have the following structures for example:

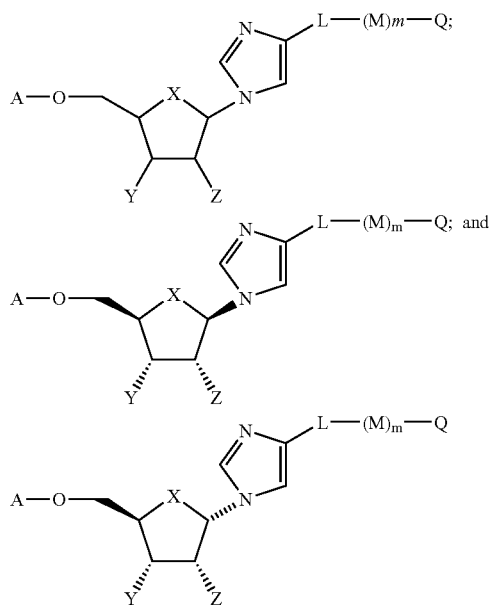

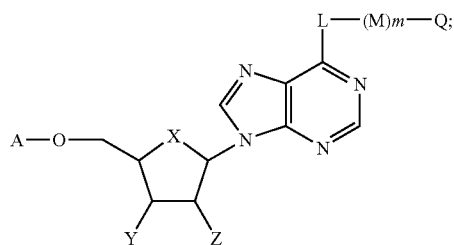

wherein A is H or $H_4O_9P_3$—; X is O; Y is H or $OR_9$, wherein $R_9$ is H, alkyl or aryl; Z is H, $N_3$, F or $OR_{10}$ wherein $R_{10}$ is H, alkyl or aryl; L is —C(O)NH(CH$_2$)$_n$NH—, wherein n is an integer ranging from about 2 to about 10; Q is biotin or a carboxyfluorescein; and, M is —CO(CH$_2$)$_5$NH—, wherein m is 1 or 0.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures for example:

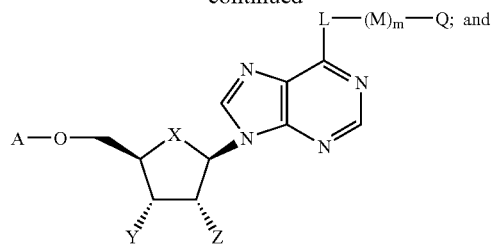

-continued

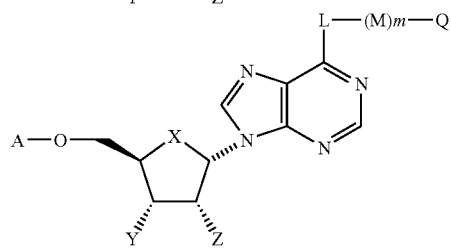

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —NH(CH$_2$)$_n$NH—, wherein n is an integer ranging from about 2 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures for example:

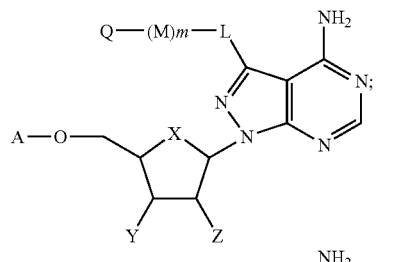

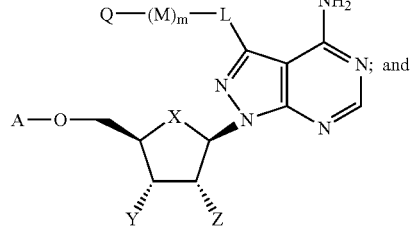

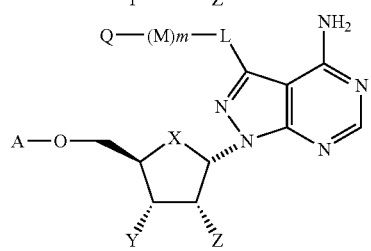

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —C≡C$(CH_2)_n$NH—, wherein n is an integer ranging from about 1 to about 10; Q is biotin or carboxyfluorescein; and, M is —CO$(CH_2)_5$NH—, wherein m is 1 or 0.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures for example:

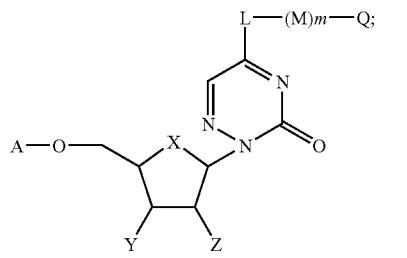

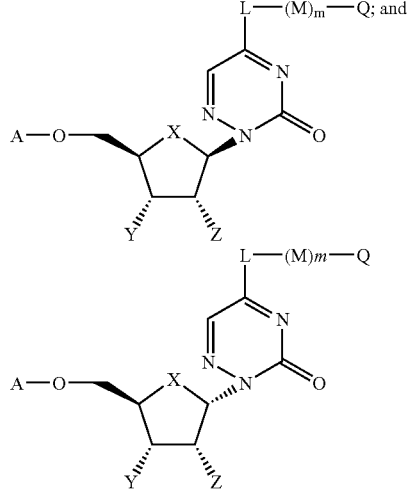

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —NH$(CH_2)_n$NH—, wherein n is an integer ranging from about 2 to about 10; Q is biotin or carboxyfluorescein; and, M is —CO$(CH_2)_5$NH— or —CO$(CH_2)_5$NHCO$(CH_2)_5$NH—, wherein m is 1 or 0.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures for example:

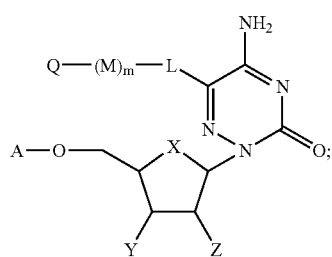

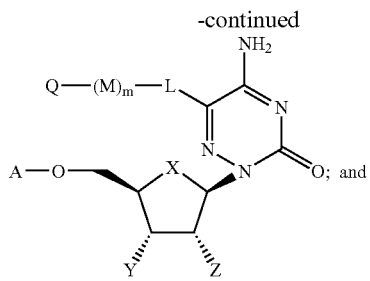

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —CH=CH$(CH_2)_n$NH—, wherein n is an integer ranging from about 1 to about 10; Q is biotin or carboxyfluorescein; and, M is —CO$(CH_2)_5$NH— or —CO$(CH_2)_5$NHCO$(CH_2)_5$NH—, wherein m is 1 or 0.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures for example:

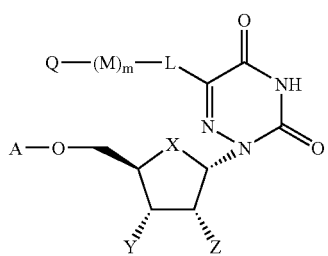

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —CH=CH$(CH_2)_n$NH—, wherein n is an integer ranging from about 1 to about 10; Q is biotin or carboxyfluorescein; and, M is —CO$(CH_2)_5$NH— or —CO$(CH_2)_5$NHCO$(CH_2)_5$NH—, wherein m is 1 or 0.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures for example:

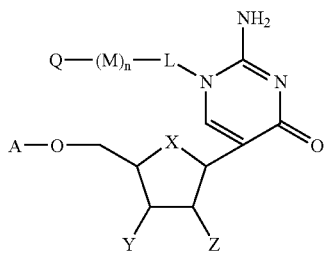

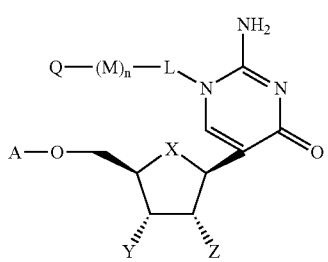

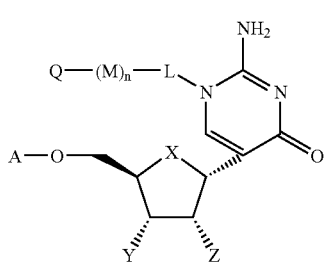

wherein A is H or a functional group that permits the attachment of the nucleic acid labeling compound to a nucleic acid; X is O, S, $NR_1$ or $CHR_2$, wherein $R_1$ and $R_2$ are, independently, H, alkyl, aryl or a functionalized alkyl or aryl; Y is H, $N_3$, F, $OR_9$, $SR_9$ or $NHR_9$, wherein $R_9$ is H, alkyl or aryl; Z is H, $N_3$, F or $OR_{10}$, wherein $R_{10}$ is H, alkyl or aryl; L is linker group; Q is a detectable moiety; and, M is a connecting group, wherein m is an integer ranging from 0 to about 3.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures for example:

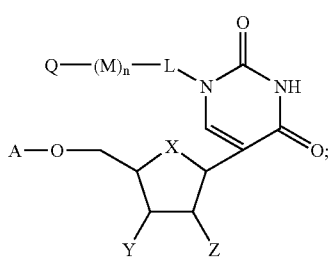

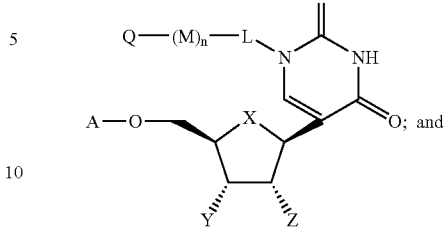

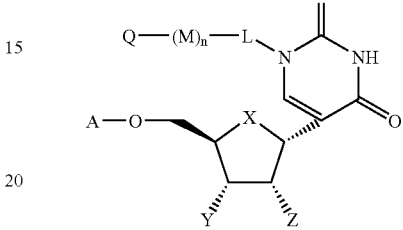

wherein A is H or a functional group that permits the attachment of the nucleic acid labeling compound to a nucleic acid; X is O, S, $NR_1$ or $CHR_2$, wherein $R_1$ and $R_2$ are, independently, H, alkyl or aryl; Y is H, $N_3$, F, $OR_9$, $SR_9$ or NHR9, wherein $R_9$ is H, alkyl or aryl; Z is H, $N_3$, F or $OR_{10}$, wherein $R_{10}$ is H, alkyl or aryl; L is functionalized alkyl; Q is a detectable moiety; and, M is a connecting group, wherein m is an integer ranging from 0 to about 3.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures for example:

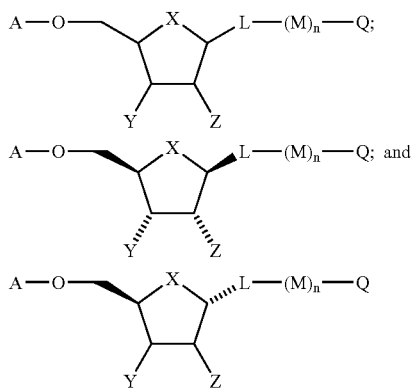

wherein A is H or a functional group that permits the attachment of the nucleic acid labeling compound to a nucleic acid; X is O, S, $NR_1$ or $CHR_2$, wherein $R_1$ and $R_2$ are, independently, H, alkyl or aryl; Y is H, $N_3$, F, $OR_9$, $SR_9$ or $NHR_9$, wherein $R_9$ is H, alkyl or aryl; Z is H, $N_3$, F or $OR_{10}$, wherein $R_{10}$ is H, alkyl or aryl; L is linker group; Q is a detectable moiety; and, M is a connecting group, wherein m is an integer ranging from 0 to about 3.

The method of nucleic acid detection using the nucleic acid derivative involves the incubation of the derivative with a probe. In one embodiment, the probe is attached to a glass chip.

In yet another embodiment, the methods involve the steps of: (a) providing at least one nucleic acid coupled to a support; (b) providing a labeled moiety capable of being coupled with a terminal transferase to said nucleic acid; (c) providing said terminal transferase; and (d) coupling said labeled moiety to said nucleic acid using said terminal transferase.

In still another embodiment, the methods involve the steps of: (a) providing at least two nucleic acids coupled to a support; (b) increasing the number of monomer units of said nucleic acids to form a common nucleic acid tail on said at least two nucleic acids; (c) providing a labeled moiety capable of recognizing said common nucleic acid tails; and (d) contacting said common nucleic acid tails and said labeled moiety.

In still yet another embodiment, the methods involve the steps of: (a) providing at least one nucleic acid coupled to a support; (b) providing a labeled moiety capable of being coupled with a ligase to said nucleic acid; (c) providing said ligase; and (d) coupling said labeled moiety to said nucleic acid using said ligase.

This invention also provides compounds of the formulas described herein.

BRIEF DESCRIPTION OF THE DRAWINGS

FIG. 18 shows various labeling reagents suitable for use in the methods disclosed herein.

DEFINITIONS

Figure 1:
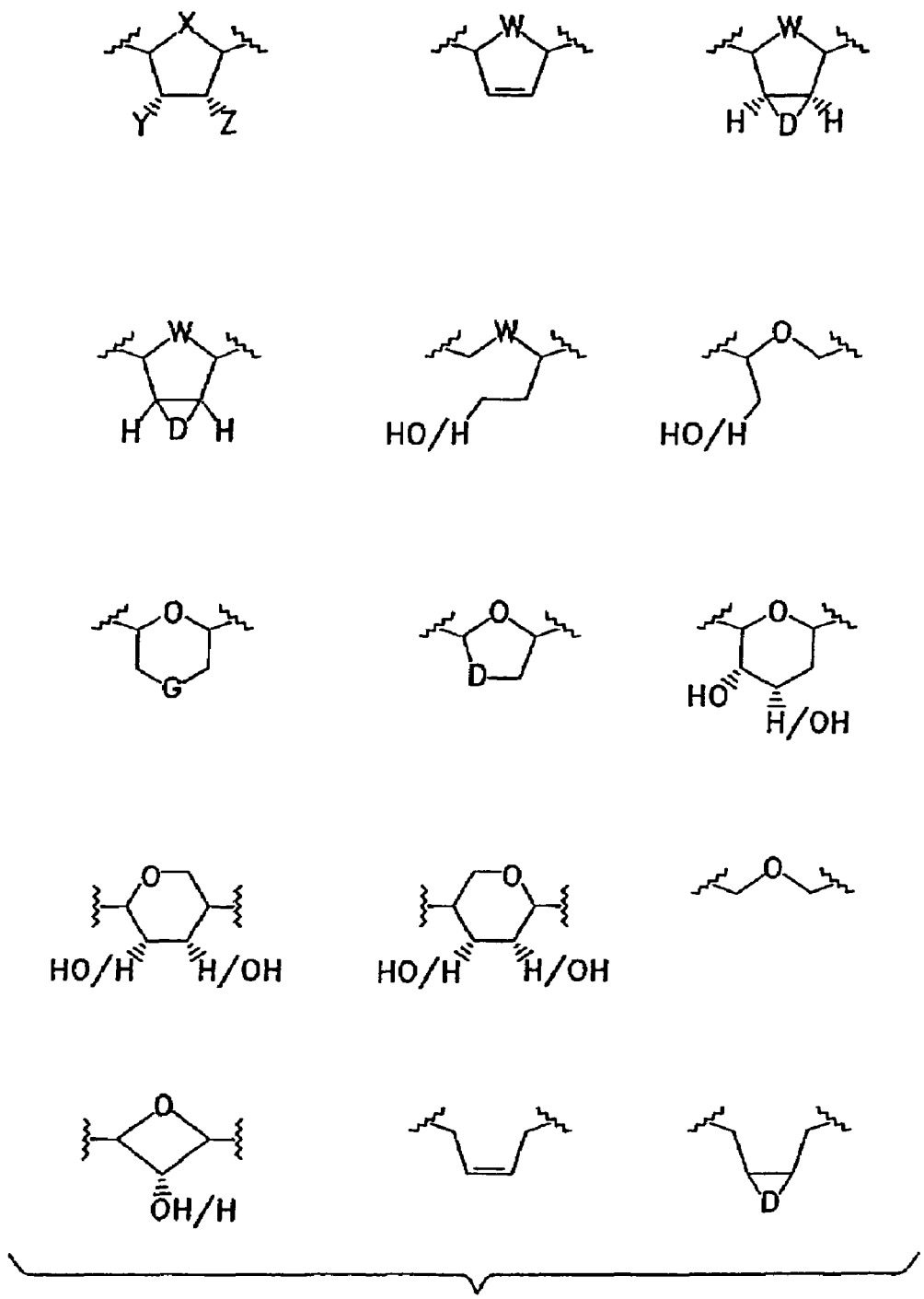
FIG. 1 shows a nonlimiting set of template moieties.

"Alkyl" refers to a straight chain, branched or cyclic chemical group containing only carbon and hydrogen. Alkyl groups include, without limitation, ethyl, propyl, butyl, pentyl, cyclopentyl and 2-methylbutyl. Alkyl groups are unsubstituted or substituted with 1 or more substituents (e.g., halogen, alkoxy, amino).

"Aryl" refers to a monovalent, unsaturated aromatic carbocyclic group. Aryl groups include, without limitation, phenyl, naphthyl, anthryl and biphenyl. Aryl groups are unsubstituted or substituted with 1 or more substituents (e.g. halogen, alkoxy, amino).

"Amido alkyl" refers to a chemical group having the structure —C(O)NR$_3$R$_4$—, wherein R$_3$ is hydrogen, alkyl or aryl, and R$_4$ is alkyl or aryl. Preferably, the amido alkyl group is of the structure —C(O)NH(CH$_2$)$_n$R$_5$—, wherein n is an integer ranging from about 2 to about 10, and R$_5$ is O, NR$_6$, or C(O), and wherein R$_6$ is hydrogen, alkyl or aryl. More preferably, the amido alkyl group is of the structure —C(O)NH(CH$_2$)$_n$N(H)—, wherein n is an integer ranging from about 2 to about 6. Most preferably, the amido alkyl group is of the structure —C(O)NH(CH$_2$)$_4$N(H)—.

"Alkynyl alkyl" refers to a chemical group having the structure —C≡C—R$_4$—, wherein R$_4$ is alkyl or aryl. Preferably, the alkynyl alkyl group is of the structure —C≡C—(CH$_2$)$_n$R$_5$—, wherein n is an integer ranging from 1 to about 10, and R$_5$ is O, NR$_6$ or C(O), wherein R$_6$ is hydrogen, alkyl or aryl. More preferably, the alkynyl alkyl group is of the structure —C≡C—(CH$_2$)$_n$N(H)—, wherein n is an integer ranging from 1 to about 4. Most preferably, the alkynyl alkyl group is of the structure —C≡C—CH$_2$N(H)—.

"Alkenyl alkyl" refers to a chemical group having the structure —CH=CH—R$_4$—, wherein R$_4$ is alkyl or aryl. Preferably, the alkenyl alkyl group is of the structure —CH=CH—(CH$_2$)$_n$R$_5$—, wherein n is an integer ranging from 1 to about 10, and R$_5$ is O, NR$_6$ or C(O), wherein R$_6$ is hydrogen, alkyl or aryl. More preferably, the alkenyl alkyl group is of the structure —CH=CH—(CH$_2$)$_n$N(H)—, wherein n is an integer ranging from 1 to about 4. Most preferably, the alkenyl alkyl group is of the structure —CH=CH—CH$_2$N(H)—.

"Functionalized alkyl" refers to a chemical group of the structure —(CH$_2$)$_n$R$_7$—, wherein n is an integer ranging from 1 to about 10, and R$_7$ is O, S, NH or C(O). Preferably, the functionalized alkyl group is of the structure —$(CH_2)_n$C(O)—, wherein n is an integer ranging from 1 to about 4. More preferably, the functionalized alkyl group is of the structure —$CH_2C(O)$—.

"Alkoxy" refers to a chemical group of the structure —$O(CH_2)_nR_8$—, wherein n is an integer ranging from 2 to about 10, and $R_8$ is O, S, NH or C(O). Preferably, the alkoxy group is of the structure —$O(CH_2)_nC(O)$—, wherein n is an integer ranging from 2 to about 4. More preferably, the alkoxy group is of the structure —$OCH_2CH_2C(O)$—.

"Thio" refers to a chemical group of the structure —$S(CH_2)_nR_8$—, wherein n is an integer ranging from 2 to about 10, and $R_8$ is O, S, NH or C(O). Preferably, the thio group is of the structure —$S(CH_2)_nC(O)$—, wherein n is an integer ranging from 2 to about 4. More preferably, the thio group is of the structure —$SCH_2CH_2C(O)$—.

"Amino alkyl" refers to a chemical group having an amino group attached to an alkyl group. Preferably an amino alkyl is of the structure —$NH(CH_2)_nNH$—, wherein n is an integer ranging from about 2 to about 10. More preferably it is of the structure —$NH(CH_2)_nNH$—, wherein n is an integer ranging from about 2 to about 4. Most preferably, the amino alkyl group is of the structure —$NH(CH_2)_4NH$—.

"Nucleic acid" refers to a polymer comprising 2 or more nucleotides and includes single-, double- and triple stranded polymers. "Nucleotide" refers to both naturally occurring and non-naturally occurring compounds and comprises a heterocyclic base, a sugar, and a linking group, preferably a phosphate ester. For example, structural groups may be added to the ribosyl or deoxyribosyl unit of the nucleotide, such as a methyl or allyl group at the 2'-O position or a fluoro group that substitutes for the 2'-O group. The linking group, such as a phosphodiester, of the nucleic acid may be substituted or modified, for example with methyl phosphonates or O-methyl phosphates. Bases and sugars can also be modified, as is known in the art. "Nucleic acid," for the purposes of this disclosure, also includes "peptide nucleic acids" in which native or modified nucleic acid bases are attached to a polyamide backbone.

The phrase "coupled to a support" means bound directly or indirectly thereto including attachment by covalent binding, hydrogen bonding, ionic interaction, hydrophobic interaction, or otherwise.

"Probe" refers to a nucleic acid that can be used to detect, by hybridization, a target nucleic acid. Preferably, the probe is complementary to the target nucleic acid along the entire length of the probe, but hybridization can occur in the presence of one or more base mismatches between probe and target.

"Perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe." In the case of expression monitoring arrays, perfect match probes are typically preselected (designed) to be complementary to particular sequences or subsequences of target nucleic acids (e.g., particular genes). In contrast, in generic difference screening arrays, the particular target sequences are typically unknown. In the latter case, prefect match probes cannot be preselected. The term perfect match probe in this context is to distinguish that probe from a corresponding "mismatch control" that differs from the perfect match in one or more particular preselected nucleotides as described below.

"Mismatch control" or "mismatch probe", in expression monitoring arrays, refers to probes whose sequence is deliberately selected not to be perfectly complementary to a particular target sequence. For each mismatch (MM) control in a high-density array there preferably exists a corresponding perfect match (PM) probe that is perfectly complementary to the same particular target sequence. In "generic" (e.g., random, arbitrary, haphazard, etc.) arrays, since the target nucleic acid(s) are unknown perfect match and mismatch probes cannot be a priori determined, designed, or selected. In this instance, the probes are preferably provided as pairs where each pair of probes differ in one or more preselected nucleotides. Thus, while it is not known a priori which of the probes in the pair is the perfect match, it is known that when one probe specifically hybridizes to a particular target sequence, the other probe of the pair will act as a mismatch control for that target sequence. It will be appreciated that the perfect match and mismatch probes need not be provided as pairs, but may be provided as larger collections (e.g., 3. 4, 5, or more) of probes that differ from each other in particular preselected nucleotides. While the mismatch(s) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions. In a particularly preferred embodiment, perfect matches differ from mismatch controls in a single centrally-located nucleotide.

"Labeled moiety" refers to a moiety capable of being detected by the various methods discussed herein or known in the art.

Nucleic Acid Labeling Compounds

The nucleic acid labeling compounds of the present invention are of the following structure:

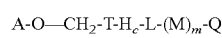

A-O—$CH_2$-T-$H_c$-L-$(M)_m$-Q wherein A is hydrogen or a functional group that permits the attachment of the nucleic acid labeling compound to a nucleic acid; T is a template moiety; $H_c$ is a heterocyclic group; L is a linker moiety; Q is a detectable moiety; and M is an connecting group, wherein m is an integer ranging from 0 to about 5.

The group A is either hydrogen or a functional group that permits the attachment of a nucleic acid labeling compound to a nucleic acid. Nonlimiting examples of such groups include the following: monophosphate; diphosphate; triphosphate ($H_4O_9P$); phosphoramidite (($R_2N$)(R'O)P), wherein R is linear, branched or cyclic alkyl, and R' is a protecting group such as 2-cyanoethyl; and H-phosphonate (HP(O)O—$HNR_3$), wherein R is linear, branched or cyclic alkyl.

The template moiety (T) is covalently attached to a methylene group ($CH_2$) at one position and a heterocyclic group ($H_c$) at another position. A nonlimiting set of template moieties is shown in FIG. 1, wherein the substituents are defined as follows: X is O, S, $NR_1$ or $CHR_2$; Y is H, $N_3$, F, $OR_9$, $SR_9$ or $NHR_9$; Z is H, $N_3$, F or $OR_{10}$; W is O, S or $CH_2$; D is or S; and, G is O, NH or $CH_2$. The substituents $R_1$, $R_2$, $R_9$ and $R_{10}$ are independent of one another and are H, alkyl or aryl.

Figure 2:
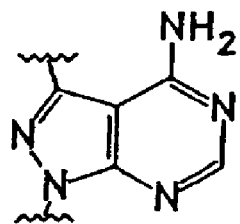
FIG. 2 shows a nonlimiting set of heterocyclic groups: 4-aminopyrazolo[3,4-d]pyrimidine, pyrazolo[3,4-d]pyrimidine, 1,3-diazole (imidazole), 1,2,4-triazine-3-one, 1,2,4-triazine-3,5-dione, and 5-amino-1,2,4-triazine-3-one.
Figure 2:
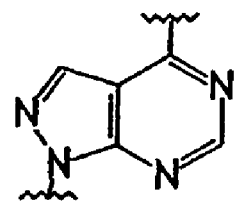
Figure 2:
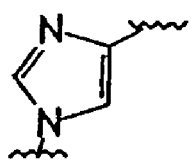
Figure 2:
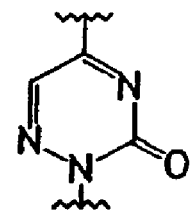
Figure 2:
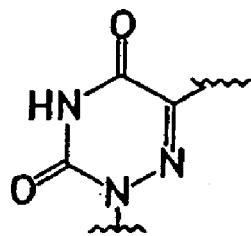
Figure 2:
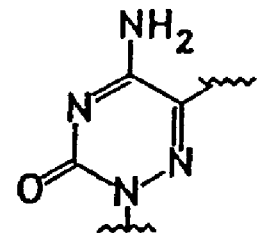
Figure 2:

The heterocyclic group ($H_c$) is a cyclic moiety containing both carbon and a heteroatom. Nonlimiting examples of heterocyclic groups contemplated by the present invention are shown in FIG. 2.: 4-aminopyrazolo[3,4-d]pyrimidine; pyrazolo[3,4-d]pyrimidine; 1,3-diazole (imidazole); 1,2,4-triazine-3-one; 1,2,4-triazine-3,5-dione; and, 5-amino-1,2,4-triazine-3-one.

The linker moiety (L) of the nucleic acid labeling compound is covalently bound to the heterocycle ($H_c$) at one terminal position. It is attached to the detectable moiety (Q) at another terminal position, either directly or through a connecting group (M). It is of a structure that is sterically and electronically suitable for incorporation into a nucleic acid. Nonlimiting examples of linker moieties include amido alkyl groups, alkynyl alkyl groups, alkenyl alkyl groups, functionalized alkyl groups, alkoxyl groups, thio groups and amino alkyl groups.

Amido alkyl groups are of the structure —C(O)$NR_3R_4$—, wherein $R_3$ is hydrogen, alkyl or aryl, and $R_4$ is alkyl or aryl. The amido alkyl group is preferably of the structure —C(O)NH(CH$_2$)$_n$$R_5$—, wherein n is an integer ranging from about 2 to about 10 and $R_5$ is O, $NR_6$ or C(O), and wherein $R_6$ is hydrogen, alkyl or aryl. More preferably, the amido alkyl group is of the structure —C(O)NH(CH$_2$)$_n$N(H)—, wherein n is an integer ranging from about 2 to about 6. Most preferably, the amido alkyl group is of the structure —C(O)NH(CH$_2$)$_4$N(H)—.

Alkynyl alkyl groups are of the structure —C≡C—$R_4$—, wherein $R_4$ is alkyl or aryl. The alkynyl alkyl group is preferably of the structure —C≡C(CH$_2$)$_n$$R_5$—, wherein n is an integer ranging from 1 to about 10 and $R_5$ is O, $NR_6$ or C(O), and wherein $R_6$ is hydrogen, alkyl or aryl. More preferably, the alkynyl alkyl group is of the structure —C≡C—(CH$_2$)$_n$N(H)—, wherein n is an integer ranging from 1 to about 4. Most preferably, the alkynyl alkyl group is of the structure —C≡C—CH$_2$N(H)—.

Alkenyl alkyl groups are of the structure —CH=CH—$R_4$—, wherein $R_4$ is alkyl or aryl. The alkenyl alkyl group is preferably of the structure —CH=CH(CH$_2$)$_n$$R_5$—, wherein n is an integer ranging from 1 to about 10, and $R_5$ is O, $NR_6$ or C(O), and wherein $R_6$ is hydrogen, alkyl or aryl. More preferably, the alkenyl alkyl group is of the structure —CH=CH(CH$_2$)$_n$NH—, wherein n is an integer ranging from 1 to about 4. Most preferably, the alkenyl alkyl group is of the structure —CH=CHCH$_2$NH—.

Functionalized alkyl groups are of the structure —(CH$_2$)$_n$$R_7$—, wherein n is an integer ranging from 1 to about 10, and $R_7$ is O, S, NH, or C(O). The functionalized alkyl group is preferably of the structure —(CH$_2$)$_n$C(O)—, wherein n is an integer ranging from 1 to about 4. More preferably, the functionalized alkyl group is —CH$_2$C(O)—.

Alkoxy groups are of the structure —O(CH$_2$)$_n$$R_8$—, wherein n is an integer ranging from 2 to about 10, and $R_8$ is O, S, NH, or C(O). The alkoxy group is preferably of the structure —O(CH$_2$)$_n$C(O)—, wherein n is an integer ranging from 2 to about 4. More preferably, the alkoxy group is of the structure —OCH$_2$CH$_2$C(O)—.

Thio groups are of the structure —S(CH$_2$)$_n$$R_8$—, wherein n is an integer ranging from 2 to about 10, and $R_8$ is O, S, NH, or C(O). The thio group is preferably of the structure —S(CH$_2$)$_n$C(O)—, wherein n is an integer ranging from 2 to about 4. More preferably, the thio group is of the structure —SCH$_2$CH$_2$C(O)—.

Amino alkyl groups comprise an amino group attached to an alkyl group. Preferably, amino alkyl groups are of the structure —NH(CH$_2$)$_n$NH—, wherein n is an integer ranging from about 2 to about 10. The amino alkyl group is more preferably of the structure —NH(CH$_2$)$_n$NH—, wherein n is an integer ranging from about 2 to about 4. Most preferably, the amino alkyl group is of the structure —NH(CH$_2$)$_4$NH—.

The detectable moiety (Q) is a chemical group that provides an signal. The signal is detectable by any suitable means, including spectroscopic, photochemical, biochemical, immunochemical, electrical, optical or chemical means. In certain cases, the signal is detectable by 2 or more means.

The detectable moiety provides the signal either directly or indirectly. A direct signal is produced where the labeling group spontaneously emits a signal, or generates a signal upon the introduction of a suitable stimulus. Radiolabels, such as $^3$H, $^{125}$I, $^{35}$S, $^{14}$C or $^{32}$P, and magnetic particles, such as Dynabeads™, are nonlimiting examples of groups that directly and spontaneously provide a signal. Labeling groups that directly provide a signal in the presence of a stimulus include the following nonlimiting examples: colloidal gold (40-80 nm diameter), which scatters green light with high efficiency; fluorescent labels, such as fluorescein, texas red, rhodamine, and green fluorescent protein (Molecular Probes, Eugene, Oreg.), which absorb and subsequently emit light; chemiluminescent or bioluminescent labels, such as luminol, lophine, acridine salts and luciferins, which are electronically excited as the result of a chemical or biological reaction and subsequently emit light; spin labels, such as vanadium, copper, iron, manganese and nitroxide free radicals, which are detected by electron spin resonance (ESR) spectroscopy; dyes, such as quinoline dyes, triarylmethane dyes and acridine dyes, which absorb specific wavelengths of light; and colored glass or plastic (e.g., polystyrene, polypropylene, latex, etc.) beads. See U.S. Pat. Nos. 3,817,837; 3,850,752; 3,939,350; 3,996,345; 4,277,437; 4,275,149 and 4,366,241.

A detectable moiety provides an indirect signal where it interacts with a second compound that spontaneously emits a signal, or generates a signal upon the introduction of a suitable stimulus. Biotin, for example, produces a signal by forming a conjugate with streptavidin, which is then detected. See Hybridization With Nucleic Acid Probes. In *Laboratory Techniques in Biochemistry and Molecular Biology*; Tijssen, P., Ed.; Elsevier: New York, 1993; Vol. 24. An enzyme, such as horseradish peroxidase or alkaline phosphatase, that is attached to an antibody in a label-antibody-antibody as in an ELISA assay, also produces an indirect signal.

A preferred detectable moiety is a fluorescent group. Flourescent groups typically produce a high signal to noise ratio, thereby providing increased resolution and sensitivity in a detection procedure. Preferably, the fluorescent group absorbs light with a wavelength above about 300 nm, more preferably above about 350 nm, and most preferably above about 400 nm. The wavelength of the light emitted by the fluorescent group is preferably above about 310 nm, more preferably above about 360 nm, and most preferably above about 410 nm.

The fluorescent detectable moiety is selected from a variety of structural classes, including the following nonlimiting examples: 1- and 2-aminonaphthalene, p,p'diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triarylmethanes, flavin, xanthene dyes (e.g., fluorescein and rhodamine dyes); cyanine dyes; 4,4-difluoro-4-bora-3a,4a-diaza-s-indacene dyes and fluorescent proteins (e.g., green fluorescent protein, phycobiliprotein).

A number of fluorescent compounds are suitable for incorporation into the present invention. Nonlimiting examples of such compounds include the following: dansyl chloride; fluoresceins, such as 3,6-dihydroxy-9-phenylxanthhydrol; rhodamineisothiocyanate; N-phenyl-1-amino-8-sulfonatonaphthalene; N-phenyl-2-amino-6-sulfonatonaphthanlene; 4-acetamido-4-isothiocyanatostilbene-2,2'-disulfonic acid; pyrene-3-sulfonic acid; 2-toluidinonapththalene-6-sulfonate; N-phenyl, N-methyl 2-aminonaphthalene-6-sulfonate; ethidium bromide; stebrine; auromine-0,2-(9'-anthroyl)palmitate; dansyl phosphatidylethanolamin; N,N'-dioctadecyl oxacarbocycanine; N,N'-dihexyl oxacarbocyanine; merocyanine, 4-(3'-pyrenyl) butyrate; d-3-aminodesoxy-equilenin; 12-(9'-anthroyl)stearate; 2-methylanthracene; 9-vinylanthracene; 2,2'-(vinylene-p-phenylene)bisbenzoxazole; p-bis[2-(4-methyl-5-phenyl oxazolyl)]benzene; 6-dimethylamino-1,2-benzophenzin; retinol; bis(3'-aminopyridinium)-1,10-decandiyl diiodide; sulfonaphthylhydrazone of hellibrienin; chlorotetracycline; N-(7-dimethylamino-4-methyl-2-oxo-3-chromenyl)maleimide; N-[p-(2-benzimidazolyl)phenyl]maleimide; N-(4-fluoranthyl)maleimide; bis(homovanillic acid); resazarin; 4-chloro-7-nitro-2,1,3-benzooxadizole; merocyanine 540; resorufin; rose bengal and 2,4-diphenyl-3(2H)-furanone. Preferably, the fluorescent detectable moiety is a fluorescein or rhodamine dye.

Another preferred detectable moiety is colloidal gold. The colloidal gold particle is typically 40 to 80 nm in diameter. The colloidal gold may be attached to a labeling compound in a variety of ways. In one embodiment, the linker moiety of the nucleic acid labeling compound terminates in a thiol group (—SH), and the thiol group is directly bound to colloidal gold through a dative bond. See Mirkin et al. *Nature* 1996, 382, 607-609. In another embodiment, it is attached indirectly, for instance through the interaction between colloidal gold conjugates of antibiotin and a biotinylated labeling compound. The detection of the gold labeled compound may be enhanced through the use of a silver enhancement method. See Danscher et al. *J. Histotech* 1993, 16, 201-207.

The connecting groups $(M)_m$ may serve to covalently attach the linker group (L) to the detectable moiety (Q). Each M group can be the same or different and can independently be any suitable structure that will not interfere with the function of the labeling compound. Nonlimiting examples of M groups include the following: amino alkyl, —CO(CH$_2$)$_5$NH—, —CO—, —CO(O)—, —CO(NH)—, —CO(CH$_2$)$_5$NHCO(CH$_2$)$_5$NH—, —NH(CH$_2$CH$_2$O)$_k$NH—, —NH(CH$_2$CH$_2$O)$_k$CH$_2$CH$_2$NH and —CO(CH$_2$)$_5$—; wherein, k is an integer from 1 to about 5, preferably k is 1 or 2; m is an integer ranging from 0 to about 5, preferably 0 to about 3.

In one embodiment, the nucleic acid labeling compounds of the present invention are of the following structure:

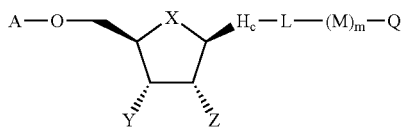

wherein L is a linker moiety; Q is a detectable moiety; X is O, S, NR$_1$ or CHR$_2$; Y is H, N$_3$, F, OR$_9$, SR$_9$ or NHR$_9$; Z is H, N$_3$, F or OR$_{10}$; H$_c$ is a heterocyclic group; A is H or a functional group that permits the attachment of the nucleic acid label to a nucleic acid; and, M is a connecting group, wherein m is an integer ranging from 0 to about 3. The substituents R$_1$, R$_2$, R$_9$ and R$_{10}$ are independent of one another and are H, alkyl or aryl.

In one embodiment, the heterocyclic group (H$_c$) is an imidazole, and the nucleic acid labeling compounds have the following structures:

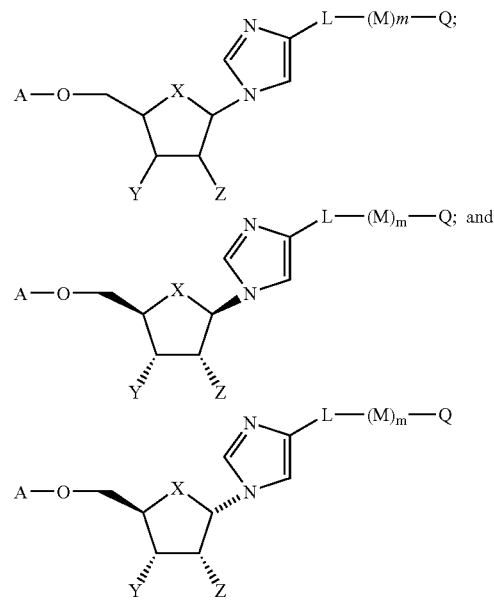

wherein L is a linker moiety; Q is a detectable moiety; X is O, S, NR$_1$ or CHR$_2$; Y is H, N$_3$, F, OR$_9$, SR$_9$ or NHR$_9$; Z is H, N$_3$, F or OR$_{10}$; A is H or a functional group that permits the attachment of the nucleic acid label to a nucleic acid; and, M is a connecting group, wherein m is an integer ranging from 0 to about 3. The substituents R$_1$, R$_2$, R$_9$ and R$_{10}$ are independent of one another and are H, alkyl or aryl.

In a preferred embodiment, the heterocyclic group (H.) is an imidazole and the linking moiety is amido alkyl:

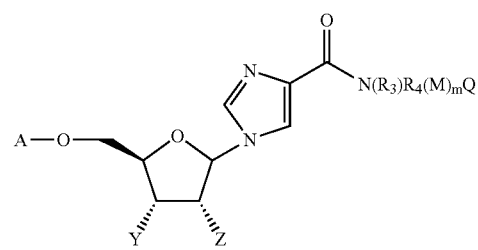

wherein Y is hydrogen or hydroxyl; Z is hydrogen or hydroxyl; R$_3$ is hydrogen or alkyl; R$_4$ is —(CH$_2$)$_n$NH—, wherein n is an integer ranging from about 2 to about 10; Q is biotin or carboxyfluorescein; A is hydrogen or H$_4$O$_9$P$_3$—; and, M is —CO(CH$_2$)$_5$NH— or —CO—, wherein m is 1 or 0. More preferably, Y and Z are hydrogen; R$_3$ is hydrogen; R$_4$ is —(CH$_2$)$_4$NH—; A is H$_4$O$_9$P$_3$—; and, Q is biotin, wherein M is —CO(CH$_2$)$_5$NH— and m is 1, or 5- or 6-carboxyfluorescein, wherein m is 0.

In another embodiment, the heterocyclic group ($H_c$) is a C3 substituted 4-amino-pyrazolo[3,4-d]pyrimidine, and the nucleic acid labeling compounds have the following structures:

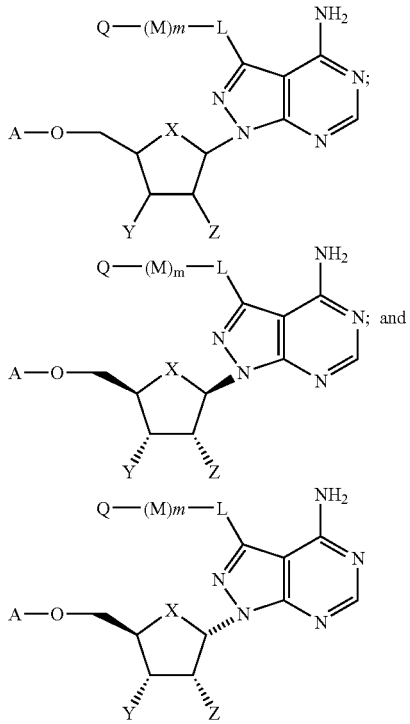

wherein L is a linker moiety; Q is a detectable moiety; X is O, S, $NR_1$ or $CHR_2$; Y is H, $N_3$, F, $OR_9$, $SR_9$ or $NHR_9$; Z is H, $N_3$, F or $OR_{10}$; A is H or a functional group that permits the attachment of the nucleic acid label to a nucleic acid; and, M is a connecting group, wherein m is an integer ranging from 0 to about 3. The substituents $R_1$, $R_2$, $R_9$ and $R_{10}$ are independent of one another and are H, alkyl or aryl.

In a preferred embodiment, the heterocyclic group ($H_c$) is a C3 substituted 4-aminopyrazolo[3,4-d]pyrimidine and the linking group is an alkynyl alkyl:

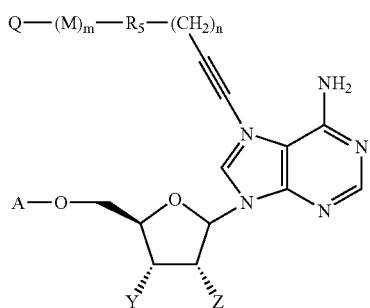

wherein Y is hydrogen or hydroxyl; Z is hydrogen or hydroxyl; n is an integer ranging from 1 to about 10; $R_5$ is 0 or NH; A is hydrogen or $H_4O_9P_3$—; Q is biotin or carboxyfluorescein; M is —$CO(CH_2)_5NH$—, wherein m is 1 or 0. More preferably, Y and Z are OH; n is 1; $R_5$ is NH; A is $H_4O_9P_3$—; and, Q is biotin or 5- or 6-carboxyfluorescein, wherein m is 1.

In another embodiment, the heterocyclic group ($H_c$) is an C4 substituted pyrazolo[3,4-d]pyrimidine, and the nucleic acid labeling compounds have the following structures:

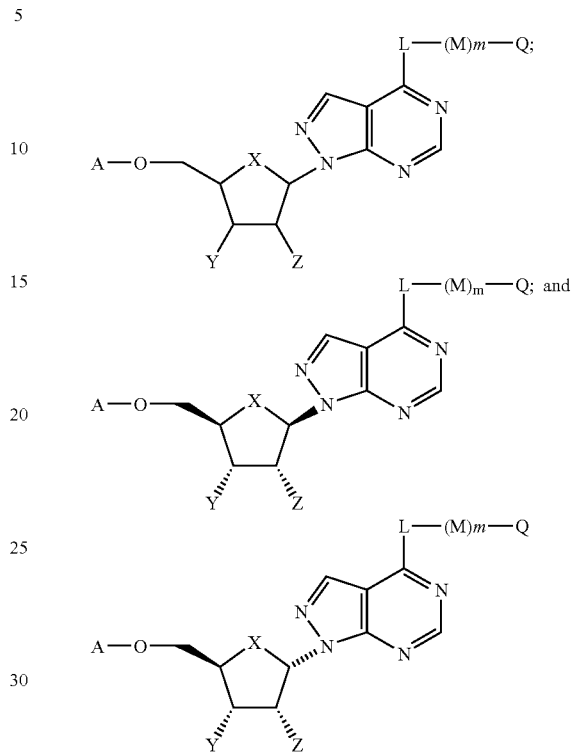

wherein L is a linker moiety; Q is a detectable moiety; X is O, S, $NR_1$ or $CHR_2$; Y is H, $N_3$, F, $OR_9$, $SR_9$ or $NHR_9$; Z is H, $N_3$, F or $OR_{10}$; A is H or a functional group that permits the attachment of the nucleic acid label to a nucleic acid; and, M is a connecting group, wherein m is an integer ranging from 0 to about 3. The substituents $R_1$, $R_2$, $R_9$ and $R_{10}$ are independent of one another and are H, alkyl or aryl.

In a preferred embodiment, the heterocyclic group ($H_c$) is an N4 substituted 4-aminopyrazolo[3,4-d]pyrimidine and the linking group is an amino alkyl:

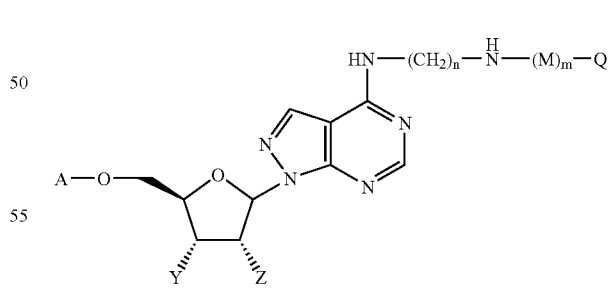

wherein Y is hydrogen or hydroxyl; Z is hydrogen or hydroxyl; n is an integer ranging from about 2 to about 10; A is hydrogen or $H_4O_9P_3$—; Q is biotin or carboxyfluorescein; M is —$CO(CH_2)_5NH$— or —$CO(CH_2)_5NHCO(CH_2)_5NH$—, wherein m is 1 or 0. More preferably, Y and Z are hydrogen; n is 4; A is $H_4O_9P_3$—; Q is biotin or 5- or 6-carboxyfluorescein, wherein m is 0.

In another embodiment, the heterocyclic group ($H_c$) is a 1,2,4-triazine-3-one, and the nucleic acid labeling compounds have the following structures:

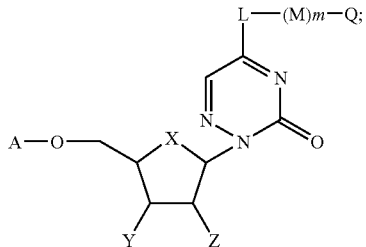

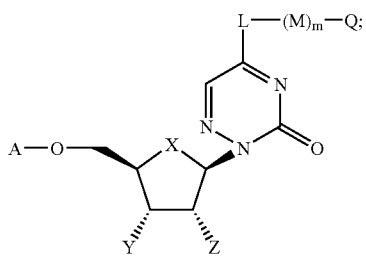

and

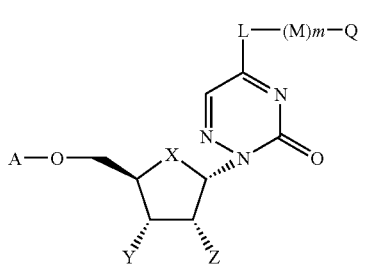

wherein L is a linker moiety; Q is a detectable moiety; X is O, S, $NR_1$ or $CHR_2$; Y is H, $N_3$, F, $OR_9$, $SR_9$ or $NHR_9$; Z is H, $N_3$, F or $OR_{10}$; A is H or a functional group that permits the attachment of the nucleic acid label to a nucleic acid; and, M is a connecting group, wherein m is an integer ranging from 0 to about 3. The substituents $R_1$, $R_2$, $R_9$ and $R_{10}$ are independent of one another and are H, alkyl or aryl.

In a preferred embodiment, the heterocyclic group ($H_c$) is a 1,2,4-triazine-3-one and the linking group is amino alkyl:

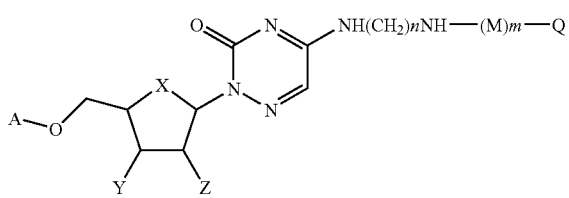

wherein Y is hydrogen or hydroxyl; Z is hydrogen or hydroxyl; n is an integer ranging from about 2 to about 10; A is hydrogen or $H_4O_9P_3$—; Q is biotin or carboxyfluorescein; M is —$CO(CH_2)_5NH$— or —$CO(CH_2)_5NHCO(CH_2)_5NH$—, wherein m is 1 or 0. More preferably, Y and Z are hydroxyl; n is 4; A is $H_4O_9P_3$—; Q is biotin or 5- or 6-carboxyfluorescein, wherein M is —$CO(CH_2)_5NH$—, and m is 1.

In another embodiment, the heterocyclic group ($H_c$) is a 1,2,4-triazine-3,5-dione, and the nucleic acid labeling compounds have the following structures:

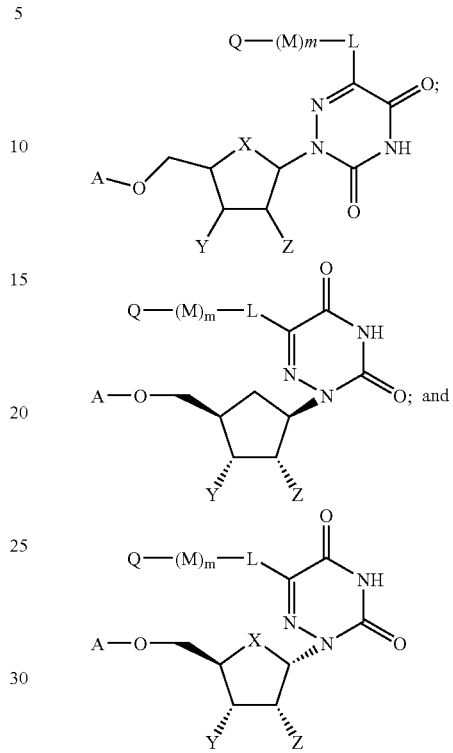

wherein L is a linker moiety; Q is a detectable moiety; X is O, S, $NR_1$ or $CHR_2$; Y is H, $N_3$, F, $OR_9$, $SR_9$ or $NHR_9$; Z is H, $N_3$, F or $OR_{10}$; A is H or a functional group that permits the attachment of the nucleic acid label to a nucleic acid; and, M is a connecting group, wherein m is an integer ranging from 0 to about 3. The substituents $R_1$, $R_2$, $R_9$ and $R_{10}$ are independent of one another and are H, alkyl or aryl.

In a preferred embodiment, the heterocyclic group ($H_c$) is a 1,2,4-triazine-3,5-dione and the linking group is alkenyl alkyl:

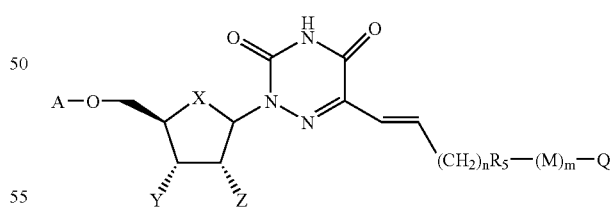

wherein Y is hydrogen or hydroxyl; Z is hydrogen or hydroxyl; n is an integer ranging from about 1 to about 10; $R_5$ is $NR_6$, wherein $R_6$ is hydrogen, alkyl or aryl; A is hydrogen or $H_4O_9P_3$—; Q is biotin or carboxyfluorescein; M is —$CO(CH_2)_5NH$— or —$CO(CH_2)_5NHCO(CH_2)_5NH$—, wherein m is 1 or 0.

In another embodiment, the heterocyclic group ($H_c$) is a 5-amino-1,2,4-triazine-3-one, and the nucleic acid labeling compounds have the following structures:

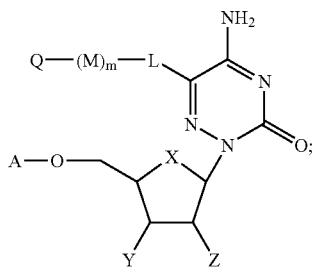

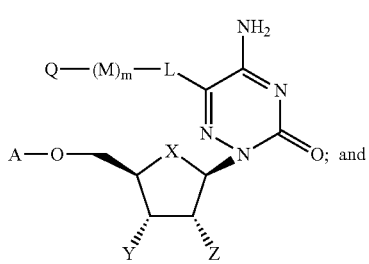

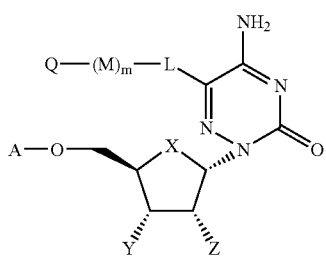

wherein L is a linker moiety; Q is a detectable moiety; X is O, S, NR$_1$ or CHR$_2$; Y is H, N$_3$, F, OR$_9$, SR$_9$ or NHR$_9$; Z is H, N$_3$, F or OR$_{10}$; A is H or a functional group that permits the attachment of the nucleic acid label to a nucleic acid; and, M is a connecting group, wherein m is an integer ranging from 0 to about 3. The substituents R$_1$, R$_2$, R$_9$ and R$_{10}$ are independent of one another and are H, alkyl or aryl.

In a preferred embodiment, the heterocyclic group (H$_c$) is a 5-amino-1,2,4-triazine-3-one and the linking group is alkenyl alkyl:

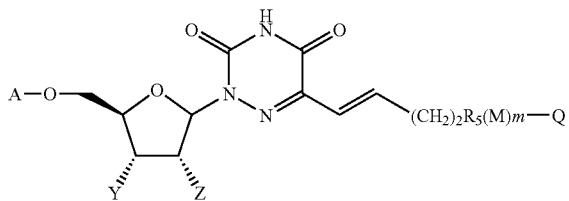

wherein Y is hydrogen or hydroxyl; Z is hydrogen or hydroxyl; n is an integer ranging from about 1 to about 10; R$_5$ is NR$_6$, wherein R$_6$ is hydrogen, alkyl or aryl; A is hydrogen or H$_4$O$_9$P$_3$—; Q is biotin or carboxyfluorescein; M is —CO(CH$_2$)$_5$NH— or —CO(CH$_2$)$_5$NHCO(CH$_2$)$_5$NH—, wherein m is 1 or 0.

In a preferred embodiment, the nucleic acid labeling compounds have the formulas:

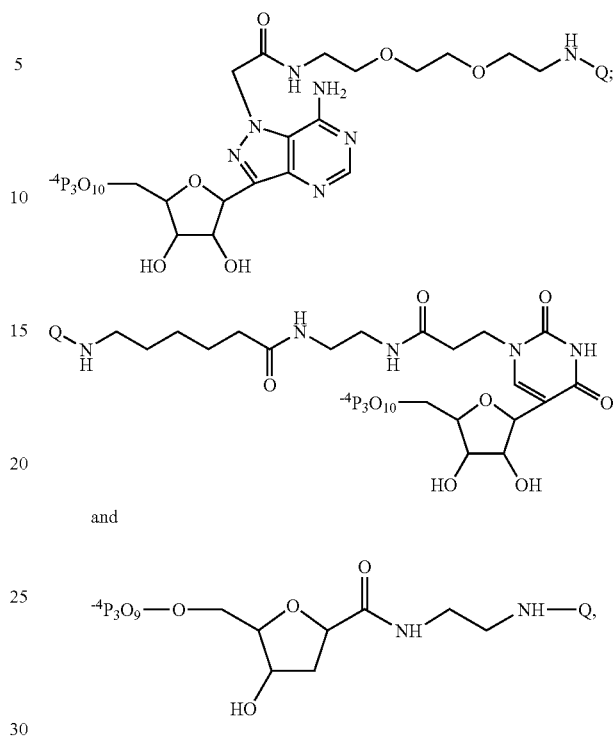

wherein Q is biotin or a carboxyfluorescein.

In another embodiment, the nucleic acid labeling compounds have the formulas:

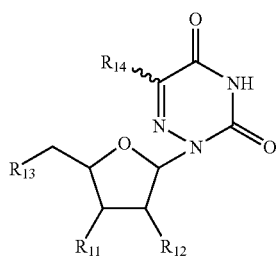

or

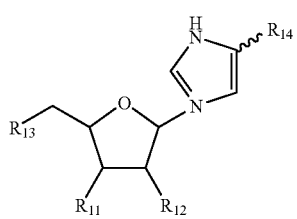

wherein R$_{11}$ is hydrogen, hydroxyl, a phosphate linkage, or a phosphate group; R$_{12}$ is hydrogen or hydroxyl; R$_{13}$ is hydrogen, hydroxyl, a phosphate linkage, or a phosphate group; and R$_{14}$ is a coupled labeled moiety.

In one embodiment, the nucleic acid labeling compounds have the following structures:

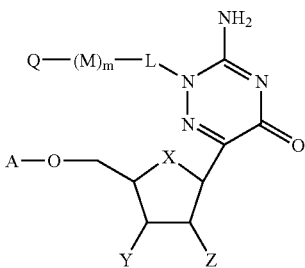

Stereoisomers are also included within the scope of the invention, examples of two of which are shown below:

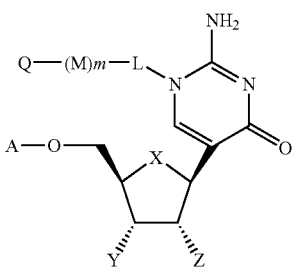

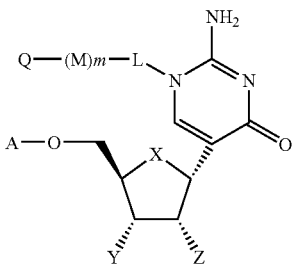

wherein A is H or a functional group that permits the attachment of the nucleic acid labeling compound to a nucleic acid; X is O, S, $NR_1$ or $CHR_2$, wherein $R_1$ and $R_2$ are, independently, H, alkyl or aryl; Y is H, $N_3$, F, $OR_9$, $SR_9$ or $NHR_9$, wherein $R_9$ is H, alkyl or aryl; Z is H, $N_3$, F or $OR_{10}$, wherein $R_{10}$ is H, alkyl or aryl; L is functionalized alkyl; Q is a detectable moiety; and, M is a connecting group, wherein m is an integer ranging from 0 to about 3.

In another embodiment, A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; ; L is —$(CH_2)_nC(O)$—, wherein n is an integer ranging from about 1 to about 10; Q is biotin or a fluorescein; and, a first M is —$NH(CH_2)_n$NH—, wherein n is an integer from about 2 to about 10, and a second M is —$CO(CH_2)_pNH$—, where p is an interger from about 2 to about 10, and wherein m is 1 or 2.

In another embodiment, Y is H or OH; Z is H or OH; L is —$(CH_2)_2C(O)$—, Q is biotin or a carboxyfluorescein; and the first M is —$NH(CH_2)_2NH$—, and the second M is —$CO(CH_2)_5NH$—, wherein m is 2.

In another embodiment, Y is OH; Z is OH; L is —$(CH_2)_2C(O)$—, Q is a carboxyfluorescein; and, a first M is —NH$(CH_2)_2NH$—, and a second M is —$CO(CH_2)_5NH$—, wherein m is 2.

In another embodiment, Y is OH; Z is OH; L is —$(CH_2)_2C(O)$—, Q is or biotin; and, a first M is —$NH(CH_2)_2NH$—, and a second M is —$CO(CH_2)_5NH$—, wherein m is 2.

In another embodiment, wherein A is a functional group the permits the attachment of the nucleic acid labeling compound to a nucleic acid; preferably, A is a triphosphate group with approprite counterions, said counterions selected from the group consisting of H+, Na+, Li+, K+, and NH4+; X is O; Y is OH; Z is OH; L is selected from the group consisting of —CH=CH—C(O)—NH—$CH_2$—$CH_2$—NH—C(O)— and —$CH_2$—$CH_2$—C(O)—NH—$CH_2$—$CH_2$—NH—C(O); M is —$(CH_2)_5$—NH— and Q is biotin having the structure:

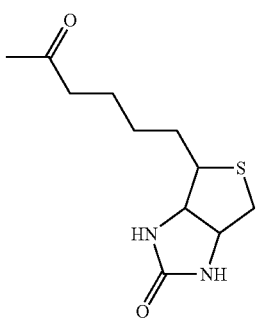

In another embodiment, L is selected from the group consisting of —CH=CH—C(O)— Q is a detectable moiety; and, M is a connecting group, wherein m is an integer ranging from 0 to about 3.

In this embodiment, A is preferably selected from the group consisting of H or $H_4O_9P_3$—; X is preferably O; Y is preferably H or $OR_9$, wherein $R_9$ is H, alkyl or aryl; Z is H, $N_3$, F or $OR_{10}$, wherein $R_{10}$ is H, alkyl or aryl. Q is preferably selected from the group consisting of a biotin or a fluorescein. In this embodiment there is preferably a first M and a second M wherein the first M is preferably —$NH(CH_2)_nNH$—, wherein n is an integer from about 2 to about 10, the second M is preferably —$CO(CH_2)_pNH$—, wherein p is an interger from about 2 to about 10 and m is 2.

In this embodiment the first M is preferably —$NH(CH_2)_2$NH— and the second M is preferably —$CO(CH_2)_5NH$—.

In another embodiment L comprises a vinyl group (—CH=CH—) attached at its 1 position directly to the N of the base. In accordance with this aspect of the present invention, where L is vinyl, further substituents are attached to the 2 position of the vinyl groups such as such as for example $R_{11}$(—CH=CH—$R_{11}$). Preferably $R_{11}$ is alkyl, aryl, functionalized alkyl, amido alkyl, alkenyl alkyl, alkoxy, thio and amino alkyl. Most preferablbly $R_{11}$ is $C(O)R_{12}$, where $R_{12}$ is a bond, aryl, functionalized alkyl, amido alkyl, alkenyl alkyl alkoxy, thio and amino alkyl.

In accordance with one aspect of the present invention, $R_{12}$ is preferably a bond, Y is OH; Z is OH; L is —$(CH_2)_2C(O)$—, and Q is selected from the group consisting of a fluorescein and a biotin; and a first M is —$NH(CH_2)_2NH$—, and a second M is —$CO(CH_2)_5NH$—, wherein m is 2.

In one embodiment, the nucleic acid labeling compounds have the following structures:

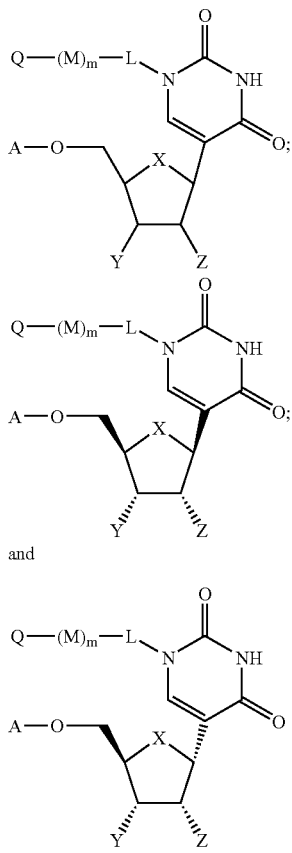

and wherein A is H or a functional group that permits the attachment of the nucleic acid labeling compound to a nucleic acid;

X is O, S, $NR_1$ or $CHR_2$, wherein $R_1$ and $R_2$ are, independently, H, alkyl or aryl; Y is H, $N_3$, F, $OR_9$, $SR_9$ or $NHR_9$, wherein $R_9$ is H, alkyl or aryl; Z is H, $N_3$, F or $OR_{10}$, wherein $R_{10}$ is H, alkyl or aryl; L is functionalized alkyl; Q is a detectable moiety; and, M is a connecting group, wherein m is an integer ranging from 0 to about 3.

In another embodiment, A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; ; L is —$(CH_2)_n$C(O)—, wherein n is an integer ranging from about 1 to about 10; Q is biotin or a fluorescein; and, a first M is —NH$(CH_2)_n$NH—, wherein n is an integer from about 2 to about 1 0, and a second M is —CO$(CH_2)_5$NH—, wherein m is 1 or 2.

In another embodiment, Y is H or OH; Z is H or OH; L is —$(CH_2)_2$C(O)—, Q is biotin or a carboxyfluorescein; and a first M is —NH$(CH_2)_2$NH—, and a second M is —CO$(CH_2)_5$NH—, wherein m is 2.

In another embodiment, Y is OH; Z is OH; L is —$(CH_2)_2$C(O)—, Q is a carboxyfluorescein; and, a first M is —NH$(CH_2)_2$NH—, and a second M is —CO$(CH_2)_5$NH—, wherein m is 2.

In another embodiment, Y is OH; Z is OH; L is —$(CH_2)_2$C(O)—, Q is or biotin; and, a first M is —NH$(CH_2)_2$NH—, and a second M is —CO$(CH_2)_5$NH—, wherein m is 2.

In another embodiment, wherein A is a functional group the permits the attachment of the nucleic acid labeling compound to a nucleic acid; preferably, A is a triphosphate group with appropriate counterions, said counterions selected from the group consisting of H+, Na+, Li+, K+, and $NH_4$+; X is O; Y is OH; Z is OH; L is selected from the group consisting of —CH=CH—C(O)—NH—$CH_2$—$CH_2$—NH—C(O)— and —$CH_2$—$CH_2$—C(O)—NH—$CH_2$—$CH_2$—NH—C(O); M is —$(CH_2)_5$—NH— and Q is biotin having the structure:

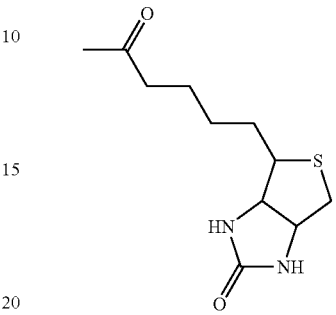

In another embodiment, L is —CH=CH—C(O)—; Q is a detectable moiety; and, M is a connecting group, wherein m is an integer ranging from 0 to about 3.

In this embodiment, A is preferably selected from the group consisting of H or $H_4O_9P_3$—; X is preferably O; Y is preferably H or $OR_9$, wherein $R_9$ is H, alkyl or aryl; Z is H, $N_3$, F or $OR_{10}$, wherein $R_{10}$ is H, alkyl or aryl. Q is preferably selected from the group consisting of a biotin or a fluorescein. In this embodiment there is preferably a first M and a second M wherein the first M is preferably —NH$(CH_2)_n$NH—, wherein n is an integer from about 2 to about 10, the second M is preferably —CO$(CH_2)_p$NH—, wherein p is an interger from about 2 to about 10 and m is 2.

In this embodiment the first M is preferably —NH$(CH_2)_2$NH— and the second M is preferably —CO$(CH_2)_5$NH—.

In another embodiment L comprises a vinyl group (—CH=CH—) attached at its 1 position directly to the N of the base. In accordance with this aspect of the present invention, where L is vinyl, further substituents are attached to the 2 position of the vinyl groups such as such as for example $R_{11}$(—CH=CH—$R_{11}$). Preferably $R_{11}$ is alkyl, aryl, functionalized alkyl, amido alkyl, alkenyl alkyl, alkoxy, thio and amino alkyl. Most preferablbly $R_{11}$ is C(O)$R_{12}$, where $R_{12}$ is a bond, aryl, functionalized alkyl, amido alkyl, alkenyl alkyl alkoxy, thio and amino alkyl. Importantly, as disclosed in accordance with one aspect of the present invention, the linker group L is selected to provide a linking function, which either alone or in conjunction with appropirate connecting groups (M) appropriately spaces the Q group from the Hc group (nucleotide base) at such a length and in such a configuration as to allow an appropriate assay to be performed on the Q group, but at the same time substantially preserving the ability of the nucleic acid labeling compound to act as a substrate for the appropriate enzyme, e.g., terminal transferase and/or RNA polymerase . Those of skill in the art will also appreciate that the chosen Hc-L-(M)m-Q groups must not adversely impact the ability of a nucleic acid strand incorporating such group to undergo Watson-Crick type base pairing with complementary sequences.

In accordance with one aspect of the present invention, $R_{12}$ is preferably a bond, Y is OH; Z is OH; L is —$(CH_2)_2$(O)—, and Q is selected from the group consisting of a fluorescein and a biotin; and a first M is —NH(CH₂)₂NH—, and a second M is —CO(CH₂)₅NH—, wherein m is 2.

In one embodiment, the nucleic acid labeling compounds have the following structures:

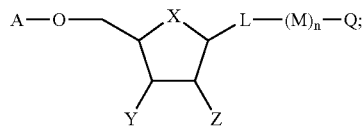

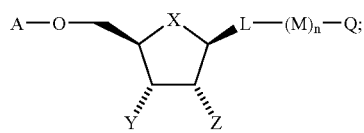

and

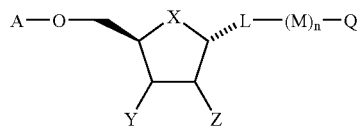

wherein A is H or a functional group that permits the attachment of the nucleic acid labeling compound to a nucleic acid;

X is O, S, NR₁ or CHR₂, wherein R₁ and R₂ are, independently, H, alkyl or aryl; Y is H, N₃, F, OR₉, SR₉ or NHR₉, wherein R₉ is H, alkyl or aryl; Z is H, N₃, F or OR₁₀, wherein R₁₀ is H, alkyl or aryl; L is amido alkyl; Q is a detectable moiety; and, M is a connecting group, wherein m is an integer ranging from 0 to about 3.

In another embodiment, A is H or H₄O₉P₃—; X is O; Y is H or OR₉, wherein R₉ is H, alkyl or aryl; Z is H, N₃, F or OR₁₀, wherein R₁₀ is H, alkyl or aryl; ; L is —C(O)NH (CH₂)ₙNH—, wherein n is an integer ranging from about 2 to about 10; Q is biotin or a fluorescein; wherein m is 0, 1, or 2.

In another embodiment, Y is H or OH; Z is H or OH; L is —C(O)NH(CH₂)₄NH— or, more preferably, C(O)NH (CH2)2NH; M is C(O)(CH2)5)NH and Q is biotin or a carboxyfluorescein.

In another embodiment, Y is OH; Z is H; L is —C(O) NH(CH₂)₄NH— or, more preferably, C(O)NH(CH2)2NH; M is C(O)(CH2)5)NH; Q is biotin.

In another embodiment, Y is OH; Z is H; L is —C(O) NH(CH₂)₄NH— or, more preferably, C(O)NH(CH2)2NH; M is C(O)(CH2)5)NH; and Q is a carboxyfluorescein.

In another embodiment, wherein A is a functional group the permits the attachment of the nucleic acid labeling compound to a nucleic acid; preferably, A is a triphosphate group with apporpriate counterions, said counterions selected from the group consisting of H+, Na+, Li+, K+, and NH₄+, Y is OH, Z is H or OH, L is —C(O)NH(CH₂)₂NH—, M is —C(O)(CH2)5NH—, n is 1 and Q is biotin, having the structure:

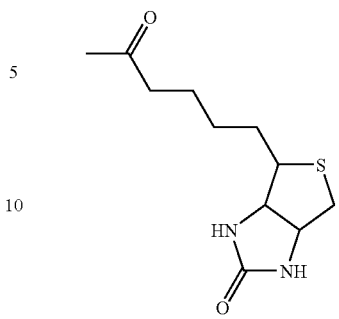

In another embodiment, wherein A is a functional group the permits the attachment of the nucleic acid labeling compound to a nucleic acid; preferably, A is a triphosphate group with apporpriate counterions, said counterions selected from the group consisting of H+, Na+, Li+, K+, and NH₄+, Y is OH, Z is H or OH, L is —C(O)NH(CH₂)₂NH—, M is —C(O)((CH₂)₂O)₄(CH₂)₂NH—, n is 1 and Q is biotin, having the structure:

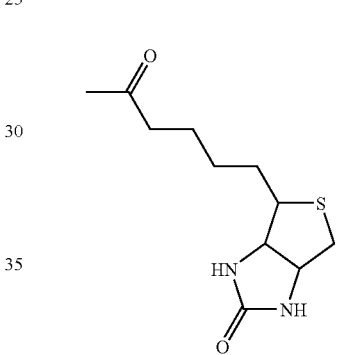

Synthesis of Nucleic Acid Labeling Compounds

Figure 3:
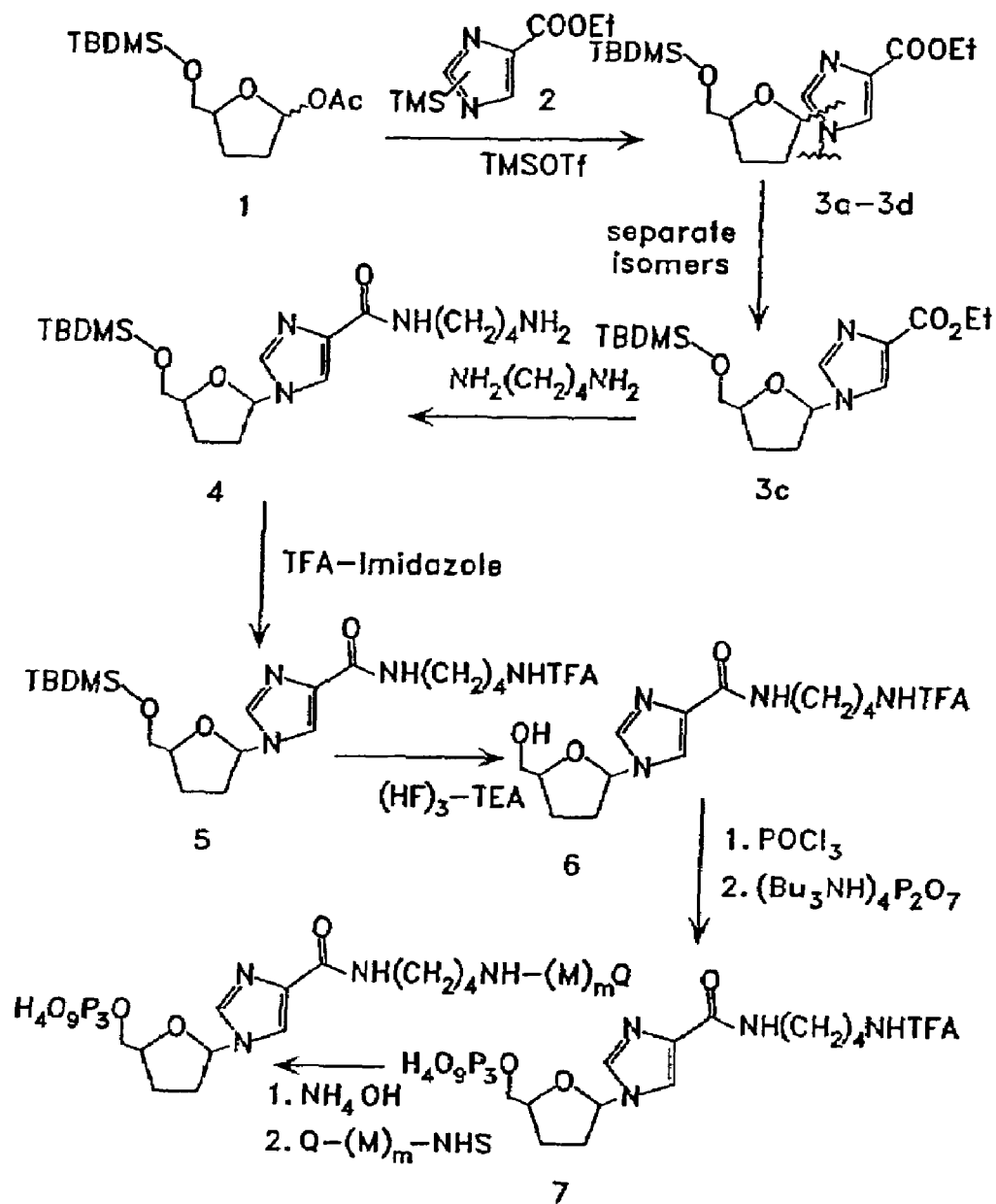
FIG. 3 shows a synthetic route to fluorescein and biotin labeled 1-(2,3-dideoxy-D-glycero-pentafuranosyl)imidazole-4-carboxamide nucleotides.

FIG. 3 shows a synthetic route to nucleic acid labeling compounds 8a and 8b, in which the heterocyclic group (H$_c$) is an imidazole and the linker moiety (L) is an amido alkyl. The silyl protected imidazole (2) was added to pentofuranose (1) to provide a mixture of carboethoxyimidazole dideoxyriboside isomers (3a-3d). The isomers were separated to afford purified 3c. The carboethoxy group of 3c was converted into an amino carboxamide (4) upon treatment with a diamine. The terminal amine of 4 was protected to give the trifluoroacetylated product 5. The silyl protecting group of 5 was removed, providing the primary alcohol 6. Compound 6 was converted into a 5'-triphosphate to afford 7. The trifluoroacetyl protecting group of 7 was removed, and the deprotected amine was reacted with biotin-NH (CH₂)₅ CO—NHS or 5-carboxyfluorescein-NHS giving, respectively, nucleic acid labeling compounds 8a and 8b.

Figure 4:
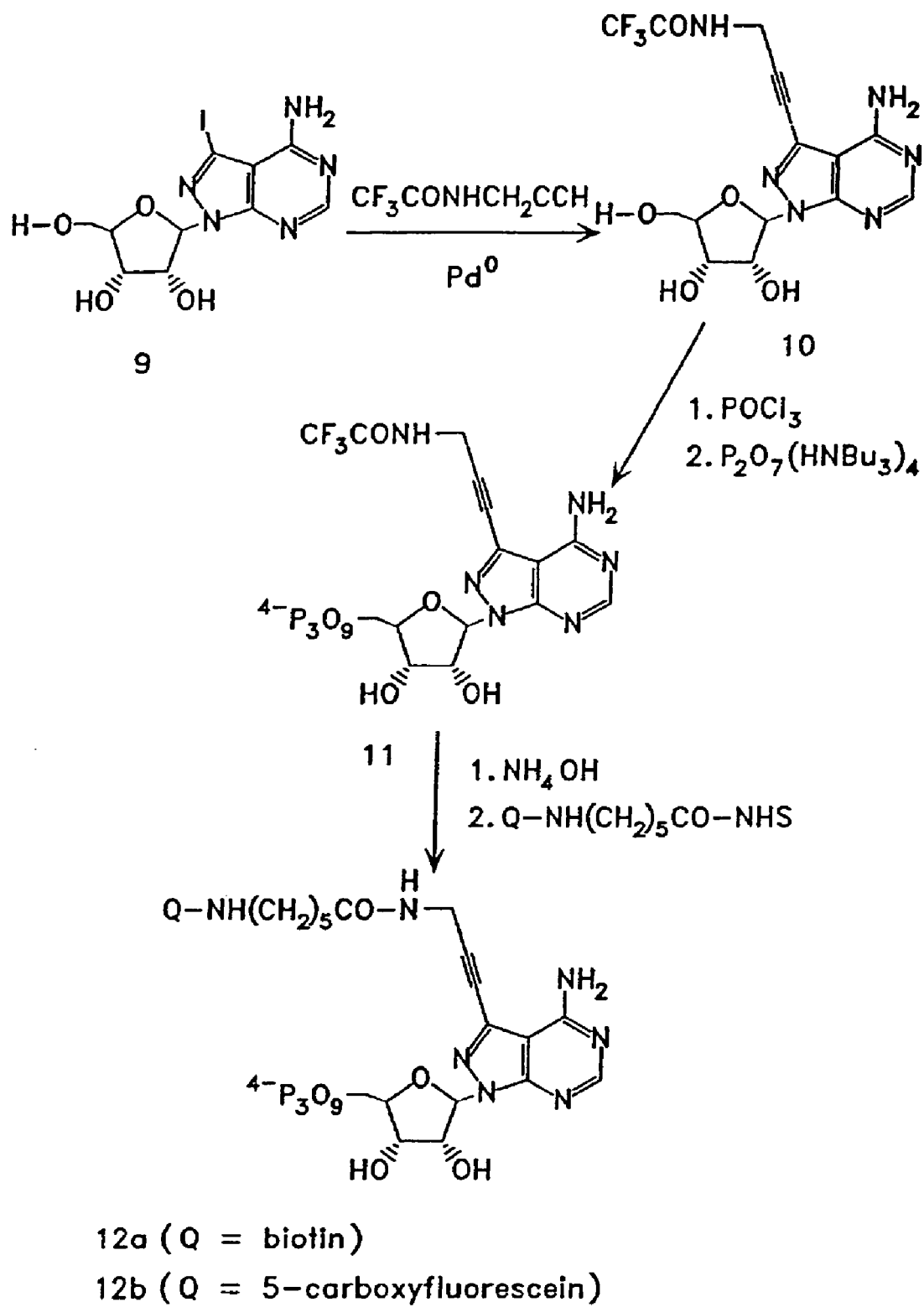
FIG. 4 shows a synthetic route to C3-labeled 4-aminopyrazolo[3,4-d]pyrimidine β-D-ribofuranoside triphosphates.

FIG. 4 shows a synthetic route to C3-labeled 4-aminopyrazolo[3,4-d]pyrimidine β-D-ribofuranoside triphosphates. A protected propargylamine linker was added to nucleoside (9) under palladium catalysis to provide the coupled product (10). The primary alcohol of the alkyne substituted nucleoside (10) was phosphorylated, yielding the 5'-triphosphate 11. The protected amine of triphosphate 11 was then deprotected, and the resulting primary amine was treated with a reactive biotin or fluorescein derivative to afford, respectively, nucleic acid labeling compounds 12a and 12b.

Figure 5:
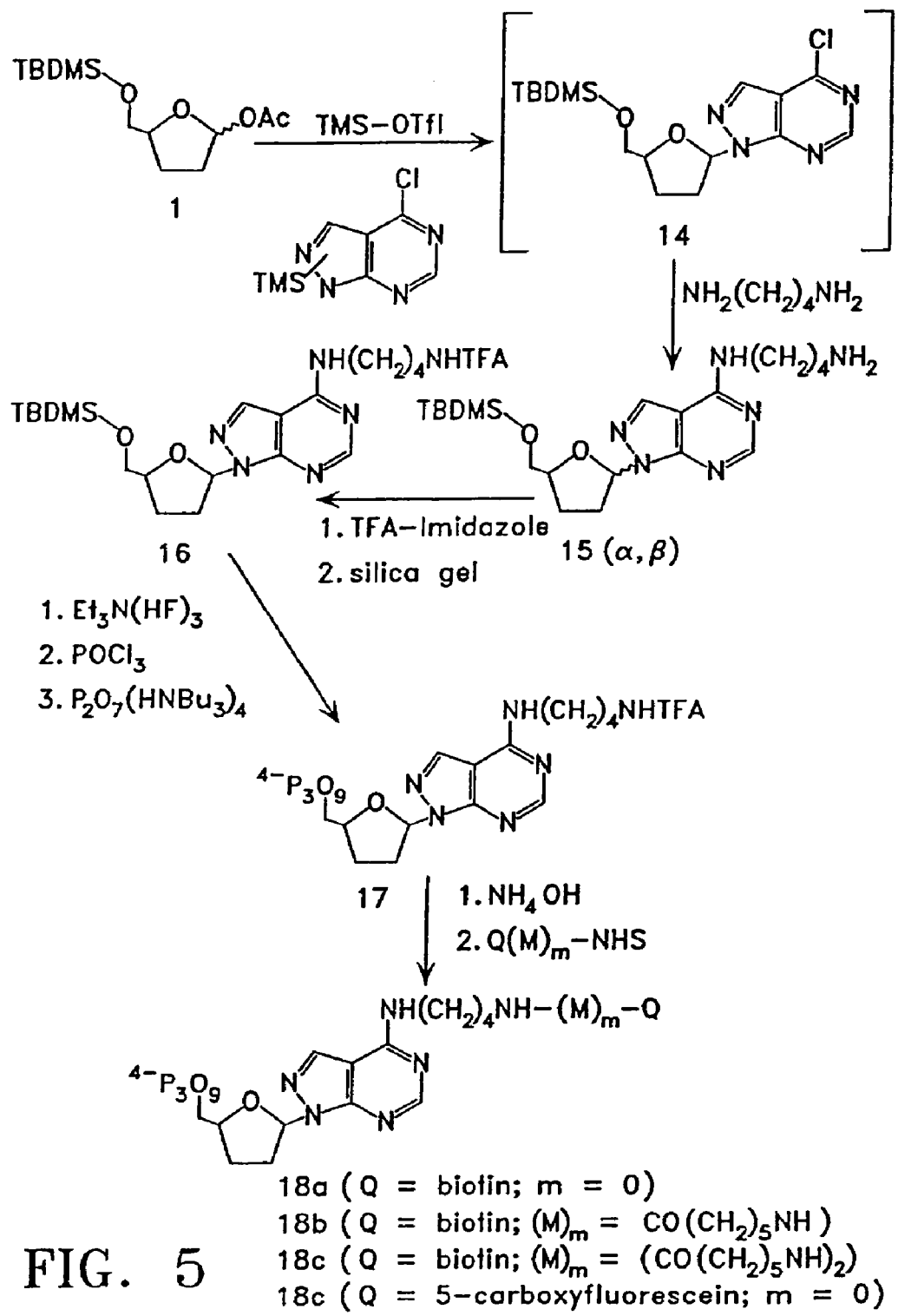
FIG. 5 shows a synthetic route to fluorescein and biotin labeled N6-dideoxy-pyrazolo[3,4-d]pyrimidine nucleotides.

FIG. 5 shows a synthetic route to pyrazolopyrimidine nucleotides. A chloropyrazolopyrimidine (13) was added to pentofuranose 1 to provide adduct 14 as a mixture of anomers. A diamine was added to compound 14, affording a mixture of primary amines (15). The primary amines (15) were protected and chromatographically separated to yield the pure β-anomer 16. The silyl group of 16 was removed and the resulting primary alcohol was phosphorylated to provide triphosphate 17. The trifluoroacetyl group of 17 was removed and the deprotected amine was treated with a reactive biotin or carboxyfluorescein derivative giving, respectively, nucleic acid labeling compounds 18a-18d.

Figure 6:
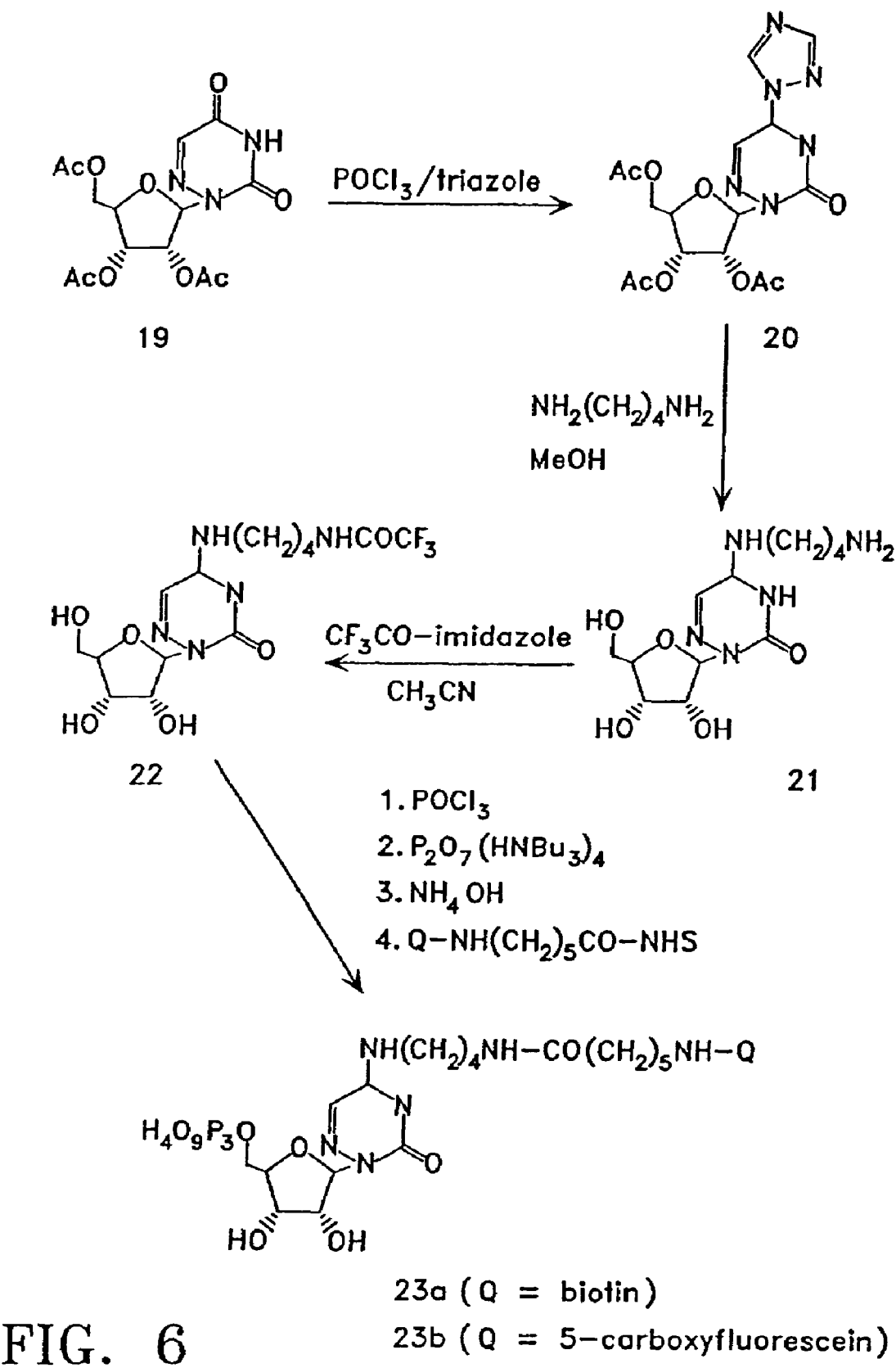
FIG. 6 shows a synthetic route to N4-labeled 1,2,4-triazine-3-one β-D-ribofuranoside triphosphates.

FIG. 6 shows a synthetic route to N4-labeled 1,2,4-triazine-3-one β-D-ribofuranoside triphosphates. 1,2,4-Triazine-3,5-dione ribonucleoside 19 was converted into the triazole nucleoside 20 upon treatment with triazole and phosphorous trichloride. Addition of a diamine to 20 provided aminoalkyl nucleoside 21. The primary amine of 21 was protected, affording trifluoroacetamide 22. The primary alcohol of 22 was phosphorylated, and the protected amine was deprotected and reacted with a reactive biotin or carboxyfluorescein derivative, giving, respectively, nucleic acid labeling compounds 23a and 23b.

Figure 7:
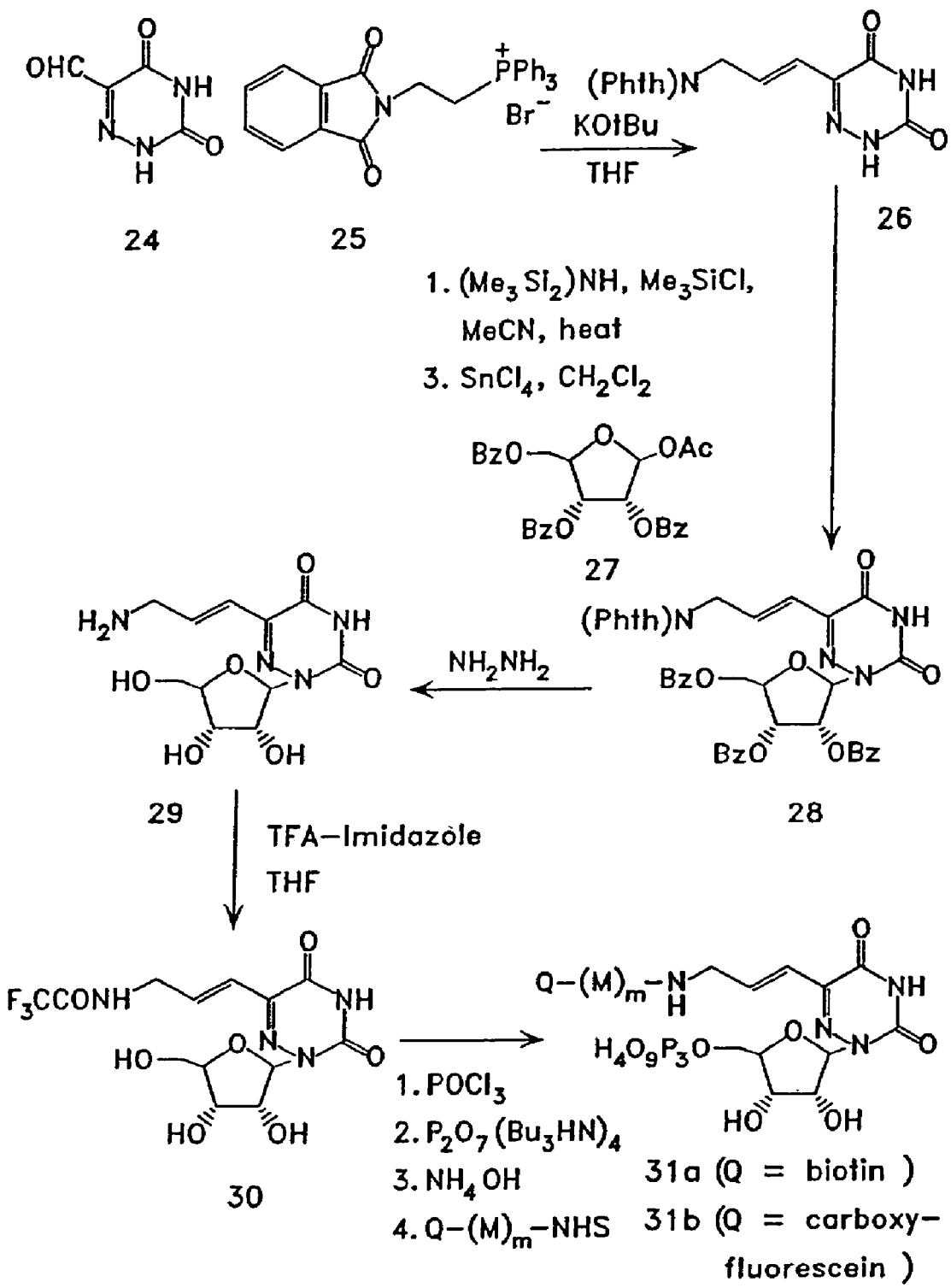
FIG. 7 shows a synthetic route to biotin and fluorescein C5-labeled 1,2,4-triazine-3,5-dione riboside triphosphates.

FIG. 7 shows a synthetic route to C5-labeled 1,2,4-triazine-3,5-dione riboside phosphates. Aldehyde 24 is reacted with ylide 25 to provide the phthalimide protected allylamine 26. Compound 26 is coupled with pentofuranoside 27, yielding nucleoside 28. The phthalimide group of 28 is removed upon treatment with hydrazine to afford primary amine 29. Amine 29 is protected as amide 30. Amide 30 is phosphorylated, deprotected and treated with a reactive derivative of biotin or carboxyfluorescein, giving, respectively, nucleic acid labeling compounds 31a and 31b.

Figure 8:
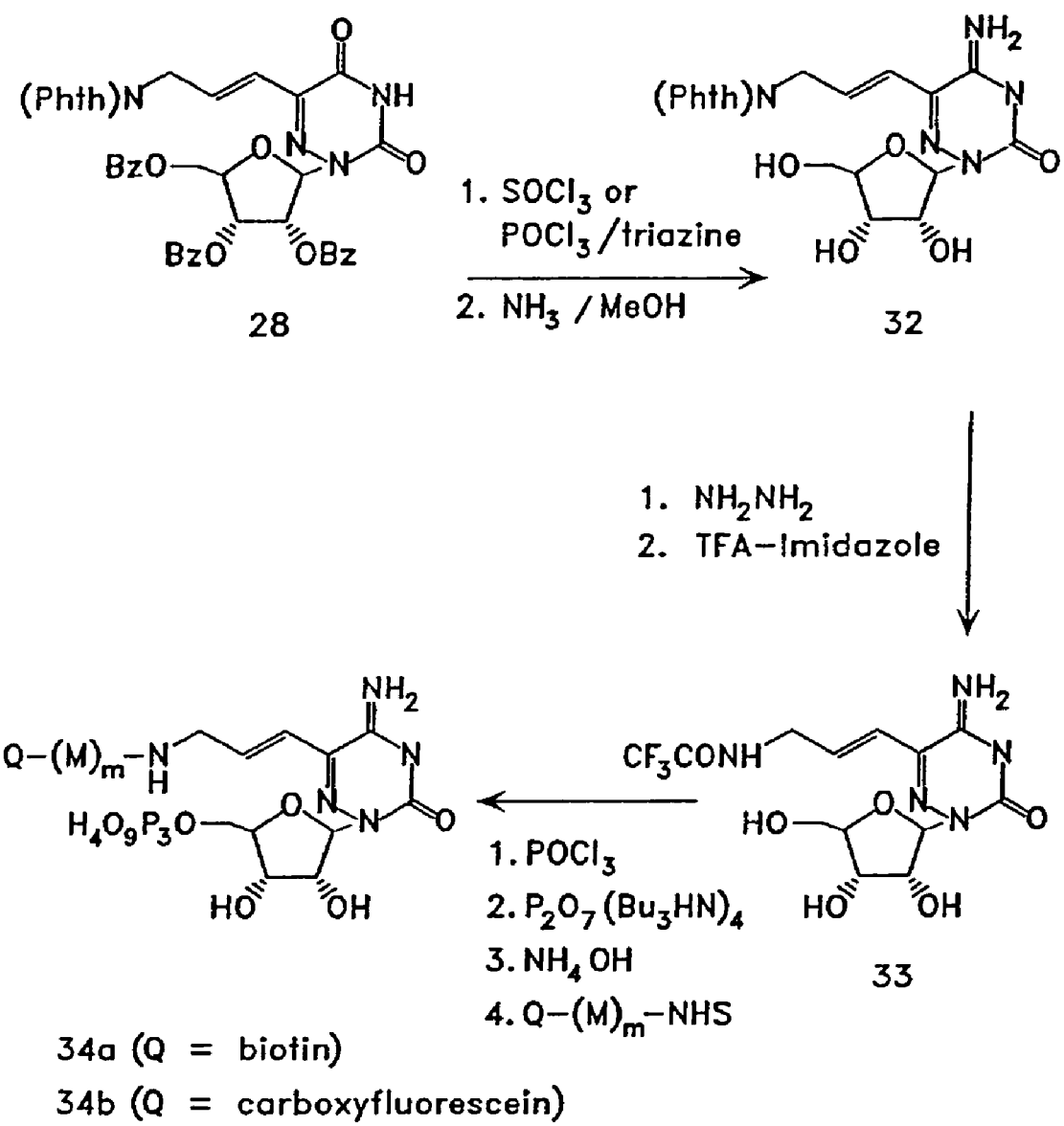
FIG. 8 shows a synthetic route to biotin and fluorescein C5-labeled 5-amino-1,2,4-triazine-3-one riboside triphosphates.

FIG. 8 shows a synthetic route to C5-labeled 5-amino-1,2,4-triazine-3-one riboside triphosphates. Compound 28 is converted into the amino-1,3-6-triazine compound 32 upon treatment with a chlorinating agent and ammonia. The phthalimide group of 32 is removed upon treatment with hydrazine, and the resulting primary amine is protected to provide 33. Compound 33 is phosphorylated, deprotected and treated with a reactive derivative of biotin or carboxyfluorescein, giving, respectively, nucleic acid labeling compounds 34a and 34b.

Nucleic Acid Labeling

Nucleic acids can be isolated from a biological sample or synthesized, on a solid support or in solution for example, according to methods known to those of skill in the art. As used herein, there is no theoretical limitation on the length or source of the nucleic acid used in the labeling process. Limitations on length may, however, be imposed or suggested by the hybridization process. Exemplary methods of nucleic acid isolation and purification are described in Theory and Nucleic Acid Preparation. In *Laboratory Techniques in Biochemistry and Molecular Biology: Hybridization With Nucleic Acid Probes*; P. Tijssen, Ed.; Part I; Elsevier: N.Y., 1993. A preferred method of isolation involves an acid guanidinium-phenol-chloroform extraction followed by oligo dT column chromotography or (dT)n magnetic bead use. Sambrook et al. *Molecular Cloning: A Laboratory Manual*, 2nd ed.; Cold Spring Harbor Laboratory, 1989; Vols. 1-3; and *Current Protocols in Molecular Biology*; F. Ausubel et al. Eds.; Greene Publishing and Wiley Interscience: N.Y., 1987.

In certain cases, the nucleic acids are increased in quantity through amplification. Suitable amplification methods include, but are not limited to, the following examples: polymerase chain reaction (PCR) (Innis, et al. *PCR Protocols. A guide to Methods and Application*; Academic Press: San Diego, 1990); ligase chain reaction (LCR) (Wu and Wallace. *Genomics* 1989, 4, 560; Landgren, et al. *Science* 1988, 241, 1077; and Barringer, et al. *Gene* 1990, 89, 117); transcription amplification (Kwoh et al. *Proc. Natl. Acad. Sci. USA* 1989, 86, 1173); and self-sustained sequence replication (Guatelli, et al. *Proc. Nat. Acad. Sci. USA* 1990, 87, 1874). Each of these references is hereby incorporated by reference.

The nucleic acid labeling compound can be incorporated into a nucleic acid using a number of methods. For example, it can be directly attached to an original nucleic acid sample (e.g., mRNA, polyA mRNA, cDNA) or to an amplification product. Methods of attaching a labeling compound to a nucleic acid include, without limitation, nick translation, 3-end-labeling, ligation, in vitro transcription (IVT) or random priming. Where the nucleic acid is an RNA, a labeled riboligonucleotide is ligated, for example, using an RNA ligase such asT4 RNA Ligase. See *The Enzymes*; Uhlenbeck and Greensport, Eds.; Vol. XV, Part B, pp. 31-58; and, Sambrook et al., pp. 5.66-5.69 (incorporated here by reference). Terminal transferase is used to add deoxy-, dideoxy- or ribonucleoside triphosphates (dNTPs, ddNTPs or NTPs), for example, where the nucleic acid is single stranded DNA.

The labeling compound can also be incorporated at an internal position of a nucleic acid. For example, PCR in the presence of a labeling compound provides an internally labeled amplification product. See, e.g., Yu et al. *Nucleic Acids Research* 1994, 22, 3226-3232 (incorporated by reference). Similarly, IVT in the presence of a labeling compound can provide an internally labeled nucleic acid.

Probe Hybridization

The nucleic acid to which the labeling compound is attached can be detected after hybridization with a nucleic acid probe. Alternatively, the probe can be labeled, depending upon the experimental scheme preferred by the user. The probe is a nucleic acid, or a modified nucleic acid, that is either attached to a solid support or is in solution. It is complementary in structure to the labeled nucleic acid with which it hybridizes. The solid support is of any suitable material, including polystyrene based beads and glass chips. In a preferred embodiment, the probe or target nucleic acid is attached to a glass chip, such as a GeneChip® product (Affymetrix, Inc., Santa Clara, Calif.). See International Publication Nos. WO 97/10365, WO 97/29212, WO 97/27317, WO 95/11995, WO 90/15070, and U.S. Pat. Nos. 5,744,305 and 5,445,934 which are hereby incorporated by reference.

Because probe hybridization is often a step in the detection of a nucleic acid, the nucleic acid labeling compound must be of a structure that does not substantially interfere with that process. The steric and electronic nature of the labeling compound, therefore, is compatible with the binding of the attached nucleic acid to a complementary structure.

EXAMPLES

The following examples are offered to illustrate, but not to limit, the present invention.

General Experimental Details

Reagents were purchased from Aldrich Chemical Company (Milwaukee, Wis.) in the highest available purity. All listed solvents were anhydrous. Intermediates were characterized by $^1$H NMR and mass spectrometry.

Example 1

Synthesis of Fluorescein- and Biotin-labeled 1-(2,3-dideoxy-β-D-glycero-pentafuranosyl)imidazole-4-carboxamide nucleotides 1-O-acetyl-5-O-(t-butyldimethylsilyl)-2,3-dideoxy-D-glycero-pentafuranose 1 (9.4 g, 34.2 mmole) (see, Duelholm, K.; Penderson, E. B., *Synthesis*, 1992, 1) and 1-trimethylsilyl-4-carboethoxyimidazole 2 (6.3 g; 34.2 mmole) (see, Pochet, S, et. al., *Bioorg. Med. Chem. Lett.*, 1995, 5, 1679) were combined in 100 ml dry DCM under Ar, and trimethylsilyl triflate catalyst (6.2 ml; 34.2 mmole) was added at 0° C. The solution was allowed to stir at room temperature for 5 hours and was then washed 3× with 100 ml of saturated aqueous $NaHCO_3$, 1× with saturated aqueous NaCl, dried with $NaSO_4$ and evaporated to provide 14 g of a crude mixture of four carboethoxyimidazole dideoxyriboside isomers (3a-d), corresponding to α and β-anomers of both N1 and N3 alkylation products. The isomeric products were purified and separated by flash chromatography (silica gel, EtOAc-hexane), in 52% total yield. The β-N1 isomer (2.2 g; 18% yield), was identified by $^1$H-NMR chemical shift and NOE data (see, Pochet, S, et. al., *Bioorg. Med. Chem. Lett.*, 1995, 5, 1679). Purified 3c (0.5 g; 1.4 mmole) was heated with a 20-fold excess of 1,4-diaminobutane (3.0 ml, 30 mmole) neat at 145° C. for 4 hours, and then the resulting mixture was diluted with 50 ml EtOAc, washed 3× with water, 1× with brine, and dried with $NaSO_4$ and evaporated to provide 500 mg (95%) of the imidazole-4-(4-aminobutyl)carboxamide dideoxyriboside 4 as a colorless oil. After coevaporation with toluene, 4 (393 mg; 0.75 mmole) was combined with trifluoroacetylimidazole (94 uL; 0.83 mmole) in 5 ml dry THF at 0° C., and stirred for 10 minutes. The solvent was evaporated, and the oily residue taken up in 50 ml EtOAc, extracted 2× with saturated aqueous $NaHCO_3$, 1× with saturated aqueous NaCl, dried with $NaSO_4$, and evaporated to yield 475 mg (99%) of the N-TFA protected nucleoside 5 as a colorless oil. The TBDMS group was removed by addition of excess triethylamine trihydrofluoride (2.3 ml; 14.4 mmole) in 20 ml dry THF and stirring overnight. The THF was evaporated in vacuo, the residue was taken up in 50 ml EtOAc and the solution was washed carefully with a 1:1 mixture of saturated aqueous $NaHCO_3$ and brine until neutral, then dried with $NaSO_4$, and evaporated to yield 340 mg (96%) of the 5 as a pale yellow oil. The NMR & MS data were consistent with the assigned structure.

Nucleoside 6 was converted to a 5'-triphosphate, deprotected, reacted with biotin-$NH(CH_2)_5CO$—NHS or 5-carboxyfluorescein-NHS and purified according to procedures reported elsewhere (see, Prober, J. M., et al., 1988, PCT 0 252 683 A2) to give the labeled nucleotides 8a,b in >95% purity by HPLC, $^{31}$P-NMR.

Example 2

Synthesis of C3-Labeled 4-aminopyrazolo[3,4-d]pyrimidine β-D-ribofuranoside triphosphates The synthesis of 3-iodo-4-aminopyrazolo[3,4-d]pyrimidine ribofuranside (9) was carried out as described by H. B. Cottam, et al. 1993, J. Med. Chem. 36:3424. Using the appropriate deoxyfuranoside precursors, both the 2'-deoxy and 2',3'-dideoxy nucleosides are prepared using analogous procedures. See, e.g., U. Neidballa & H. Vorbruggen 1974, J. Org. Chem. 39:3654; K. L. Duehom & E. B. Pederson 1992, Synthesis 1992:1). Alternatively, these are prepared by deoxygenation of ribofuranoside 9 according to established procedures. See, M. J. Robins et al. 1983 J. Am. Chem. Soc. 103:4059; and, C. K. Chu, et al. 1989 J. Org. Chem. 54:2217.

A protected propargylamine linker was added to the 4-aminopyrazolo[3,4-d]pyrimidine nucleoside (9) via organopalladium-mediated substitution to the 3-position of 4-aminopyrazolo[3,4-d]pyrimidine riboside using the procedure described by Hobbs (J. Org. Chem. 54: 3420; Science 238: 336.). Copper iodide (38 mg; 0.2 mmole), triethylamine (560 uL; 4.0 mmole), N-trifluoroacetyl-3-aminopropyne (700 uL; 6.0 mmole) and 3-iodo-4-aminopyrazolo[3,4-d]pyrimide Э-D-ribofuranoside (9) (H. B. Cottam, et al., 1993, J. Med. Chem. 36: 3424.) (786 mg; 2.0 mmole) were combined in 5 ml of dry DMF under argon. To the stirring mixture was added tetrakis(triphenylphosphine) palladium (0) (232 mg; 0.2 mmole). The solution became homogeneous within 10 minutes, and was left stirring for an additional 4 hours in the dark, at which time the reaction was diluted with 20 mL of MeOH-DCM (1:1), 3.3 g of Dowex AG-1 anion exchange resin (bicarbonate form) was added, and stirring was continued for another 15 minutes. The resin was removed by filtration and washed with MeOH-DCM (1:1), and the combined filtrates were evaporated to dryness. The residue was dissolved in 4 mL of hot MeOH, then 15 mL DCM was added and the mixture kept warm to maintain a homogeneous solution while it was loaded onto a 5 cm×25 cm column of silica gel that had been packed in 1:9 MeOH-DCM. The product ($R_f$~0.4, 6:3:1:1 DCM-EtOAc-MeOH-HOAc) was eluted with a 10-15-20% MeOH-DCM step gradient. The resulting pale yellow solid was washed 3× with 2.5 ml of ice-cold acetonitrile, then 2× with ether and dried in vacuo to obtain 630 mg (75%) of 4-amino-3-(N-trifluoroacetyl-3-aminopropynyl)pyrazolo[3,4-d]pyrimidine β-D-ribofuranoside (10). Identity of the product was confirmed by $^1$H-nmr, mass spectrometry and elemental analysis.

The nucleoside was converted to a 5'-triphosphate (11), deprotected, reacted with oxysuccinimidyl-(N-biotinoyl-6-amino)hexanoate, or oxysuccinimidyl-(N-(fluorescein-5-carboxyl)-6-amino)hexanoate, and purified according to procedures reported elsewhere (Prober, J. M., et al., 1988, PCT 0 252 683 A2.) to give the biotin- and fluorescein-labeled nucleotides (12a, 12b) in >95% purity.

Example 3

Synthesis of Fluorescein- and Biotin-N6-dideoxy-pyrazalo[3,4-d]pyrimidine Nucleotides 1-O-acetyl-5-O (t-butyldimethylsilyl)-2,3-dideoxy-D-glycero-pentofuranose (1) and 1-trimethylsilyl-4-chloropyrazolo[3,4-d]pyrimidine (13) were synthesized according to literature procedures. Duelholm, K. L.; Penderson, E. B., *Synthesis* 1992, 1-22; and, Robins, R. K., *J. Amer Chem Soc.* 1995, 78, 784-790. To 2.3 g (8.3 mmol) of 1 and 1.9 g (8.3 mmol, 1 eq) of 13 in 40 ml of dry DCM at 0° C. under argon was added slowly over 5 minutes 1.5 mL (8.3 mmol, 1 eq) of trimethylsilyl triflate. After 30 min. 4.2 ml (41.5 mmol, 5 eq) of 1,2-diaminobutane was added rapidly and the reaction was stirred at room temperature for 1 hr. The solvent was evaporated; the residue was dissolved in 50 ml of ethylacetate and washed with 50 ml of saturated aqueous. $NaHCO_3$ and dried over $Na_2SO_4$, filtered and the solvent evaporated to yield 4.2 g of a yellow foam. The foam was dissolved in 100 ml of diethyl ether and 100 ml of hexanes was added to precipitate the product as an oil. The solvent was decanted and the oil was dried under high vacuum to give 3.4 g of 15 as a pale yellow foam. HPLC, UV and MS data were consistent with a 2:1 mixture of the α- and β-anomers.

To the crude mixture of isomers (3.4 g, 8.1 mmol, ~50% pure) in 140 ml of dry THF at 0° C. under argon was added slowly 1.0 ml of 1-trifluoroacetylimidazole (8.9 mmol, 1.1 eq). The reaction was followed by RP-HPLC. An additional 5% of the acylating agent was added to completely convert the starting material to mixture of TFA-protected anomers. Bergerson, R. G. ; McManis, J. S *J. Org. Chem* 1998, 53, 3108-3111. The reaction was warmed to room temperature, and then the solvent was evaporated to about 25 ml volume and diluted with 100 ml of ethylacetate. The solution was extracted twice with 25 ml of 1% aq. NaHCO$_3$, once with brine, then dried over Na$_2$SO$_4$ and evaporated to afford 3.4 g of yellow foam. The crude material was purified by flash chromatography on silica gel in EtOAc-hexanes to give 1.3 g of the α-anomer and 0.7 g of the β-anomer of 16 (50% total yield). The 1H-NMR and MS data were consistent with the assigned structure and stereochemistry.

To 1.3 g (2.5 mmol) of 16 (α-anomer) in 50 ml of dry THF under argon was added 1 ml (13.6 mmol) of triethylamine and 6.1 ml (37.5 mmol, 15 eq) of triethylamine trihydrofluoride. After stirring for 16 hr., the solvent was evaporated, and residual triethylamine trihydrofluoride removed under high vacuum. Pirrung, M. C.; et al. *Biorg. Med. Chem. Lett.* 1994, 4, 1345-1346. The residue was dissolved in 100 ml of ethylacetate and washed carefully with 4×100 ml of sat. aq. NaHCO$_3$,once with brine, then dried over Na$_2$SO$_4$ and evaporated to give 850 mg (95%) of white foam. 1H-NMR, UV and MS data were consistent with the assigned structure of the desilylated nucleoside, which was used in the next step without further purification.

The nucleoside was converted to the triphosphate using the Eckstein phosphorylation procedure (Ludwig, J. L. ; Eckstein, F. *J. Org. Chem.* 1989, 54, 631-635) followed by HPLC purification on a ResourceQ anion exchange column (buffer A is 20 mM Tri pH8, 20% CH$_3$CN and buffer B is 20 mM Tris pH8, 1 M NaCl, 20% CH3CN). $^{31}$P-NMR, UV and MS data were consistent with the structure of the triphosphate. The trifluoroacetyl-protecting group was removed by treatment with excess NH$_4$OH at 55° C. for 1 hr. followed by evaporation to dryness. The mass spectral data were consistent with the aminobutyl nucleotide 17. Without further purification, the nucleotide was treated with either Biotin-NHS esters or 5-Carboxyfluorescein-NHS as described elsewhere (Prober, J. M., et al., 1988, PCT 0 252 683 A2) to form the labeled nucleotides 18a-18d, respectively, which were purified by HPLC as described (Prober, J. M., et al., 1988, PCT 0 252 683 A2) except that, in the case of 18a, the buffer was 20 mM sodium phosphate pH6. The $^{31}$P-NMR and UV data were consistent with the structure of the labeled analogs.

Example 4

Synthesis of N4-labeled 1,2,4-triazine-3-one β-D-ribofuranoside triphosphates

To a solution of 1,2,4-triazole (6.7 g; 97 mmole) in 30 mL dry ACN was added POCl$_3$ (2.1 mL; 22 mmole) slowly with stirring under argon. After 30 minutes, the solution was cooled to 0° C., and a solution of triethylamine (21 mL; 150 mmole) and 2',3',5'-tri-O-acetyl-6-azauridine (19, 4.14 g; 11 mmole (commercially available from Aldrich Chemical Company)) in 10 mL ACN was added. After stirring for an additional hour at room temperature, the resulting solution of activated nucleoside was transferred dropwise to a stirring solution of 1,4-diaminobutane (46 g; 524 mmole) in 20 mL MeOH. The solvents were removed in vacuo, and the residue was taken up in water, neutralized with acetic acid, and evaporated again to dryness. The crude residue was purified by chromatography on silica gel (95:5 MeOH—NH$_4$OH), followed by preparative reverse-phase HPLC to yield 150 mg (0.45 mmole; 3%) of the aminobutyl nucleoside (21). This was converted directly to the TFA-protected nucleoside (22) by reaction with 1-trifluoroacetylimidazole (300 uL; 1.8 mmole) in 3 ml ACN at 0° C. for 2 hours, evaporating the solvent and purifying by flash chromatography (1:9 MeOH-DCM). Yield 175 mg (0.42 mmole; 93%). Identity of the product was confirmed by $^1$H-nmr and mass spectrometry.

The nucleoside was converted to a 5'-triphosphate, deprotected, reacted with oxysuccinimidyl-(N-biotinoyl-6-amino) hexanoate, or oxysuccinimidyl-(N-(fluorescein-5-carboxyl)-6-amino)hexanoate, and purified according to procedures reported elsewhere (Prober, J. M., et al., 1988, PCT 0 252 683 A2.) to give the biotin- and fluorescein-labeled nucleotides (23a, 23b) in >95% purity.

Example 5

Synthesis of Biotin and Fluorescein C5-Labeled 1,2,4-Triazine-3,5-dione Riboside Triphosphates 5-Formyl-6-azauracil (24) is prepared according to literature procedures. See, Scopes, D. I. C. 1986, J. Chem. Med., 29, 809-816, and references cited therein. Compound 24 is reacted with the phosphonium ylide of 25, which is formed by treating 25 with catalytic t-butoxide, to provide the phthalimidoyl-protected allylamine 26. Protected allylamine 26 is ribosylated to provide β-anomer 28 upon reaction of 26 with β-D-pentofiuranoside 27 (commercially available from Aldrich) according to the procedure of Scopes et al. 1986, J. Chem. Med., 29, 809-816. β-ribonucleoside 28 is deprotected with anhydrous hydrazine in THF to provide allylamine 29. Reaction of primary amine 29 with trifluoroacetylimidazole in THF affords the protected amine 30.

Nucleoside 30 is converted to a 5'-triphosphate, deprotected, reacted with oxysuccinimidyl-(N-biotinoyl-6-amino) hexanoate or oxysuccinimidyl-(N-(fluorescein-5-carboxy)-6-amino)hexanoate and purified according to procedures reported elsewhere (Prober, J. M., et al. 1988, PCT 0 252 683 A2), giving, respectively, the biotin- and fluorescein-labeled nucleotides 31a and 31b.

Example 6

Synthesis of Biotin and Fluorescein C5-Labeled 5-Amino-1,2,4-triazine-3-one Riboside Triphosphates β-ribonucleoside 28, described above, is treated with SOCl$_2$ or POCl$_3$ and subsequently reacted with ammonia to provide the 4-amino-1,3,6-triazine nucleoside 32. The phthalimide group of 32 is removed upon reaction with hydrazine, and the resulting primary amine is protected to afford nucleoside 33. Nucleoside 33 is converted to a 5'-triphosphate, deprotected, reacted with oxysuccinimidyl-(N-biotinoyl-6-amino)hexanoate or oxysuccinimidyl-(N-(fluorescein-5-carboxy)-6-amino)hexanoate and purified according to procedures reported elsewhere (Prober, J. M., et al. 1988, PCT 0 252 683 A2), giving, respectively, the biotin- and fluorescein-labeled nucleotides 34a and 34b.

Example 7

Procedure for HPLC Analysis of Enzymatic Incorporation of Modified Nucleotides

Reaction Conditions

TdT 3 uM $dT_{16\ template}$
15(30) uM NTP
40 U TdT (Promega)
1× buffer, pH 7.5 (Promega)

Procedure: incubate 1 hr. at 37° C., then for 10 min. at 70° C., followed by the addition of EDTA (2 mM final concentration) in a volume of 50 uL

HPLC Analysis

Materials and Reagents 4.6 mm×250 mm Nucleopac PA-100 ion-exchange column (Dionex)

buffer A: 20 mM NaOH (or 20 mM Tris pH 8, in the case of TdT incorporation of nucleotide triphoshates that are not dye-labeled)

buffer B: 20 mM NaOH, 1M NaCl (or 20 mM Tris pH 8, 1M NaCl, in the case of TdT incorporation of nucleotide triphoshates that are not dye-labeled)

General Procedure

Dilute the reaction with 50 uL of buffer A. Inject 50 uL of this sample onto the HPLC column and fractionate using a gradient of 5 to 100% buffer B over 30 minutes at a flow rate of 1 mL/min. Detect the peaks simultaneously at 260 nm absorbance and the absorbance maximum of the dye (or the fluorescence emission maximum of the dye).

The incorporation efficiency is expressed as the fraction of oligonucleotide that is labeled. This number is determined by dividing the peak area measured at 260 nm absorbance of the labeled oligonucleotide by the sum of the peak areas of the unlabeled and labeled oligonucleotide. (The retention time of fluorescein-labeled $dT_{16}$ is on the order of 2 to 3 min. longer than the unlabeled $dT_{16}$.) The error in this type of assay is about 10%. The percentage labeling efficiency for 4 types of nucleic acid labeling compounds is shown below in Tables 1, 2 and 3.

TABLE 1

Labeling Efficiency

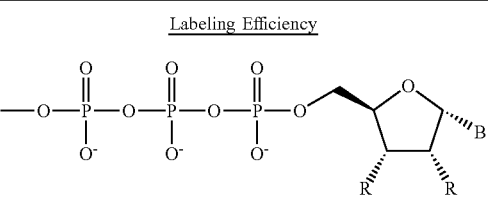

| R | B | X | % Labeling Efficiency [TdT] = | |
|---|---|---|---|---|
| | | | 40U | 160U |
| H | (1-methyl-imidazole-4-carbonyl)-NH(CH₂)₄NH—X | —C(O)(CH₂)₅NH-Biotin | 100 | — |
| H | (1-methyl-imidazole-4-carbonyl)-NH(CH₂)₄NH—X | 5-carboxy-fluorescein | 94 | 97 |
| H | (1-methyl-pyrazolo[3,4-d]pyrimidin-4-yl)-NH(CH₂)₄NH—X | 5-carboxy-fluorescein | 58 | 98 |

TABLE 1-continued

Labeling Efficiency

[Structure: triphosphate-O-CH2-sugar (with R groups at 2' and 3'), with base B]

| R | B | X | % Labeling Efficiency [TdT] = 40U | 160U |
|---|---|---|---|---|
| H | NH(CH₂)₄NH—X, 1-methyl-pyrazolo[3,4-d]pyrimidine | trifluoroacetyl | 55 | — |
| H | NH(CH₂)₄NH—X, 1-methyl-pyrazolo[3,4-d]pyrimidine | —C(O)(CH₂)₅NH-trifluoroacetyl | 49 | — |

Summary of TdT labeling efficiency data

[Structure: triphosphate-O-CH2-sugar with X groups at 2' and 3', base B]

| X = | B = | R = linker and label | % Labeling Efficiency [TdT] = 40U | 160U |
|---|---|---|---|---|
| control | | | | |
| OH | HN—(CH₂)₄NHCO(CH₂)₅NH—R, cytosine | R = 5-carboxyfluorescein | 100 | 100 |
| control | | | | |
| H | HN—(CH₂)₄NH—R, adenine | R= -biotin | 98 | 90 |
|   |   | 5-carboxyfluorescein | 97 | 100 |

-continued

Summary of TdT labeling efficiency data

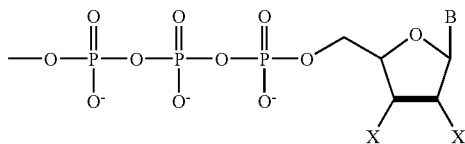

| X = | B = | R = linker and label | % Labeling Efficiency [TdT] = 40U | 160U |
|---|---|---|---|---|
| analogs: | | | | |
| H | HN—(CH₂)₄NH—R (4-amino pyrazolopyrimidine) | R= -biotin | 48 | 100 |
| | | —CO(CH₂)₅NH-biotin | 41 | 96 |
| | | —CO(CH₂)₅NHCO(CH₂)₅NH-biotin | 57 | 94 |
| | | 5-carboxyfluorescein | 58 | 98 |
| OH | NHCO(CH₂)₅NH—R (alkynyl pyrazolopyridine with NH₂) | R = -biotin | 25 | 84 |
| | | 5-carboxyfluorescein | 53 | 97 |
| | | 6-carboxyfluorescein | 37 | 86 |
| OH | (amide-PEG linker NH—R on methyl pyrazolopyrimidine NH₂) | R = -biotin | 54 | 94 |
| H | HN—(CH₂)₄NH—R (imidazole carboxamide) | R = —CO(CH₂)₅NH-biotin | 100 | —¹² |
| | | 5-carboxyflorescein | 94 | 97 |
| | | 6-carboxyfluorescein | 73 | 99 |
| H | HN—(CH₂)₄NH—R (pyrazolopyrimidine) | R = -biotin | 48 | 100 |
| | | —CO(CH₂)₅NH-biotin | 41 | 96 |
| | | —CO(CH₂)₅NHCOCH₂)₅NH-biotin | 57 | 94 |
| | | 5-carboxyflourescein | 58 | 98 |

-continued

Summary of TdT labeling efficiency data

[Structure: triphosphate-sugar with B (base) at 1' position and X substituents at 2' and 3' positions]

| X = | B = | R = linker and label | % Labeling Efficiency [TdT] = 40U | % Labeling Efficiency [TdT] = 160U |
|---|---|---|---|---|
| OH | HN—(CH₂)₄NHCO(CH₂)₅NH—R attached to 1,2,4-triazin-3(2H)-one ring | R = -biotin | 47 | 85 |
| | | 5-carboxyfluorescein | 67 | 98 |
| | | 6-carboxyfluorescein | 50 | 93 |
| OH | Uracil with N1-CH₂CH₂C(O)NH-CH₂CH₂-NH—R | R = —CO(CH₂)₅NH-biotin | 98 | 96 |
| | | —CO(CH₂)₅NH-fluorescein | 61 | 88 |
| H | —C(O)NH-CH₂CH₂-NHR | R = —CO(CH₂)₅NH-biotin | 90 | 98 |
| | | 5-carboxyfluorescein | 81 | 93 |

Example 8

Hybridization Studies of Labeled Imidazole Carboxamide ("ITP") and 4-Aminopyrazolo[3,4-d]pyrimidine ("APPTP") Nucleotides.

The performance of the labeled imidazolecarboxamide and 4-aminopyrazolo[3,4-d]pyrimidine nucleotides was evaluated in a p53 assay using standard GeneChip® product protocols (Affymetrix, Inc., Santa Clara, Calif.), which are described, for example, in detail in the GeneChip® p53 assay package insert. The sample DNA used in these experiments was the plasmid "p53mut248." The labeled nucleotide analog was substituted for the usual labeling reagent (Fluorescein-N6-ddATP or Biotin-M-N6-ddATP (wherein M=aminocaproyl), from NEN, part #'s NEL-503 and NEL-508, respectively). Labeling reactions were carried out using both the standard amount of TdT enzyme specified in the assay protocol (25 U) and with 100 U of enzyme. After labeling, Fluorescein-labeled targets were hybridized to the arrays and scanned directly. In experiments using the biotin-labeled targets, the GeneChip® chips were stained in a post-hybridization step with a phycoerythrin-streptavidin conjugate (PE-SA), prior to scanning, according to described procedures (Science 280:1077-1082 (1998)).

Figure 9:
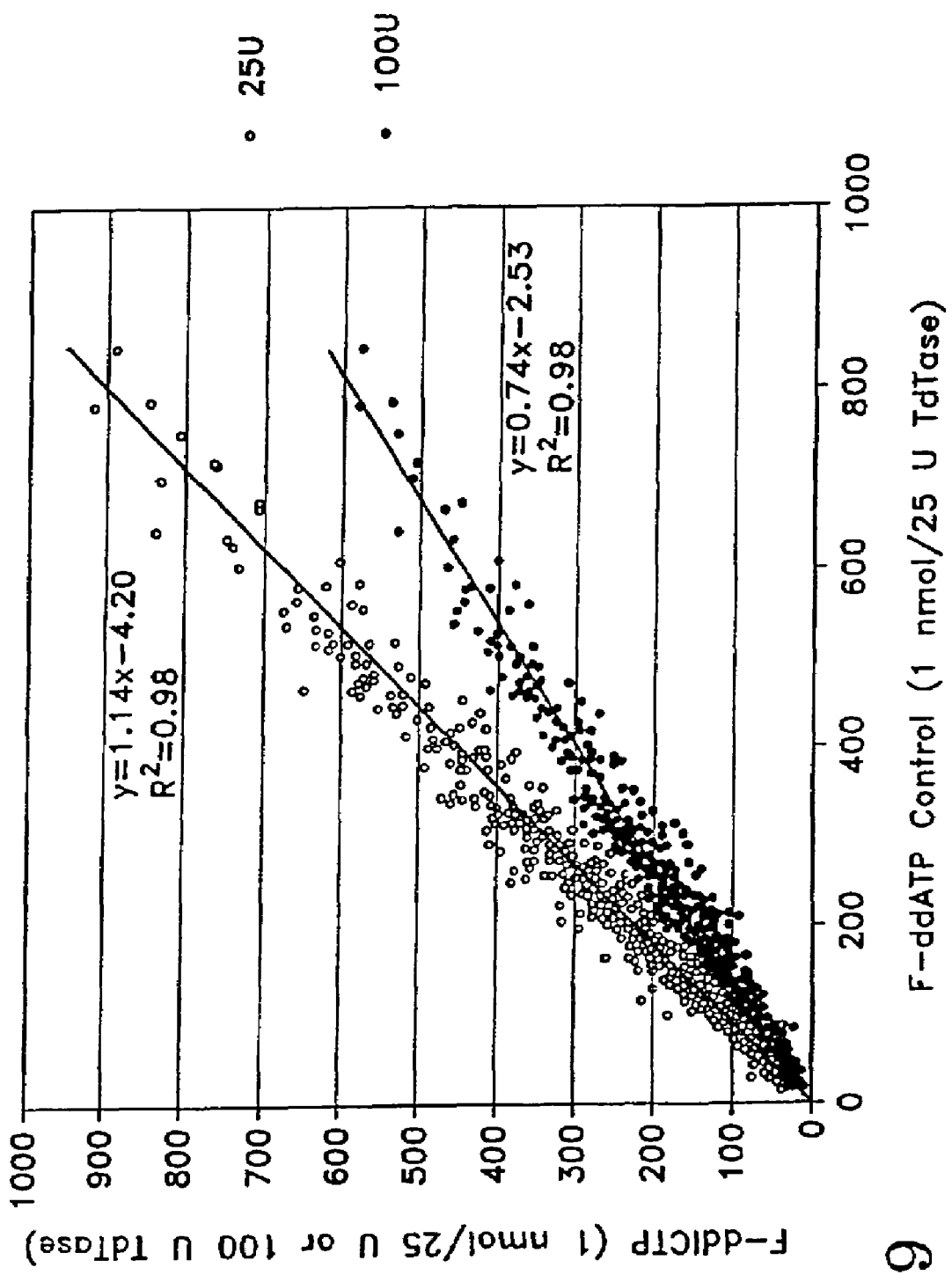
FIG. 9 shows graphical comparisons of observed hybridization fluorescence intensities using Fluorescein-ddITP and Fluorescein-ddATP.

FIG. 9 shows comparisons of the observed hybridization fluorescence intensities for the 1300 bases called in the "Unit-2" part of the chip. In the lower plot, intensities for the Fluorescein-ddATP (8b) labeled targets are plotted against those for the standard Fluorescein-N6-ddATP labeled targets (control), both at 25 U of TdT. The observed slope of ~0.75 indicates that the labeling efficiency of 8b was about 75% of that of Fluorescein-N6-ddATP under these conditions. In the upper plot, the same comparison is made, except that 100 U of TdT was used in the 8b labeling reaction. The slope of ~1.1 indicates equivalent or slightly better labeling than the standard Fluorescein-N6-ddATP/25 U control reaction.

Figure 10:
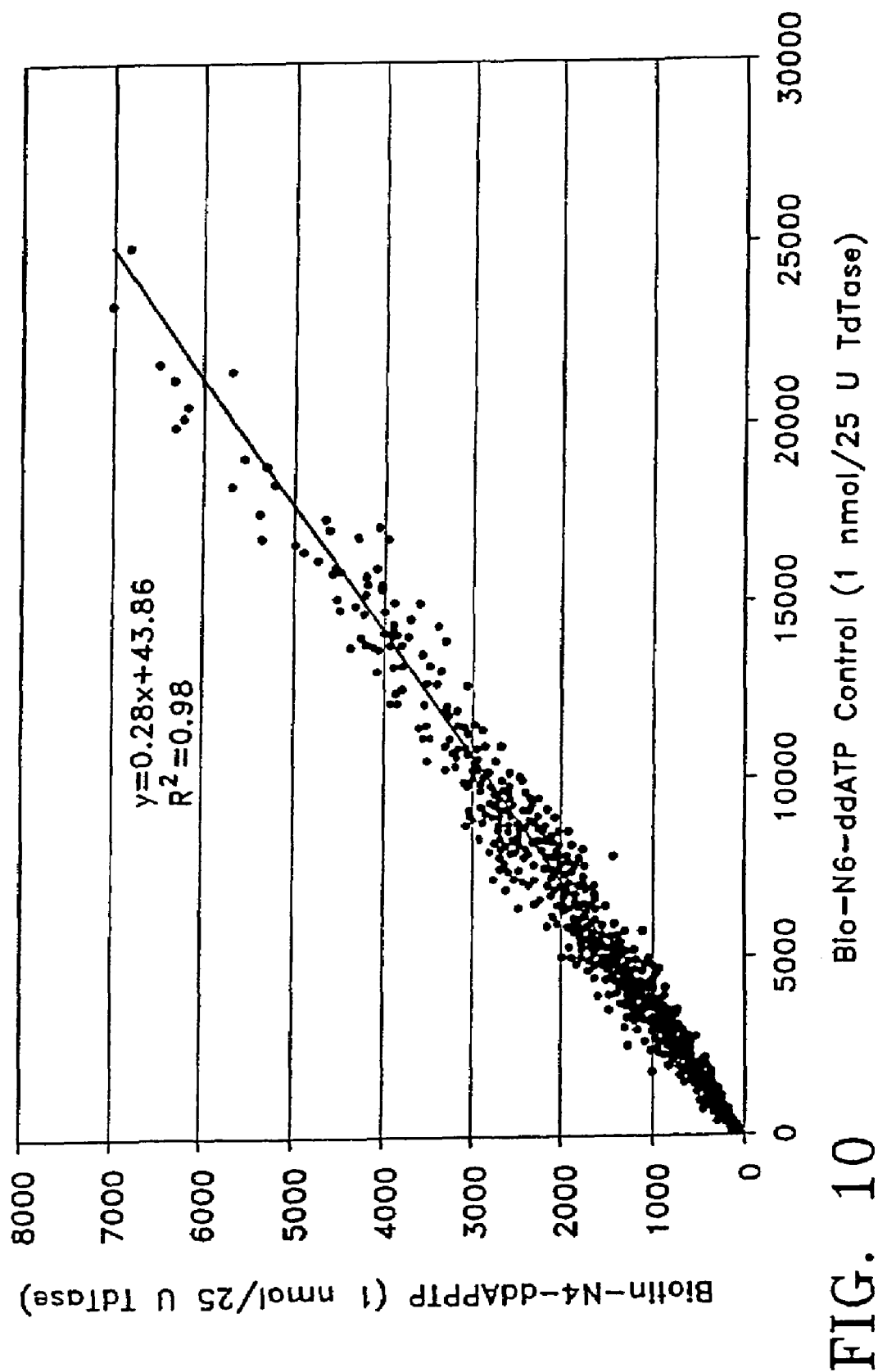
FIG. 10 shows a graphical comparison of observed hybridization fluorescence intensities using Biotin-(M)$_2$-ddAPTP (wherein M=aminocaproyl) and Biotin-N6-ddATP.

FIG. 10 shows comparisons of the observed hybridization fluorescence intensities for the 1300 bases called in the "Unit-2" part of the chip. Intensities for the Biotin-(M)₂-ddAPPTP (18c, M=aminocaproyl linker; referred to as Biotin-N4-ddAPPTP in FIG. 10) labeled targets (after PE-SA staining) are plotted against those for the standard Biotin-M-N6-ddATP labeled targets (control), both at 25 U of TdT. The observed slope of ~0.3 indicates that the labeling efficiency withBiotin-(M)₂-ddAPPTP (18c) was about 30% of that of Biotin-M-N6-ddATP under these conditions.

Figure 11:
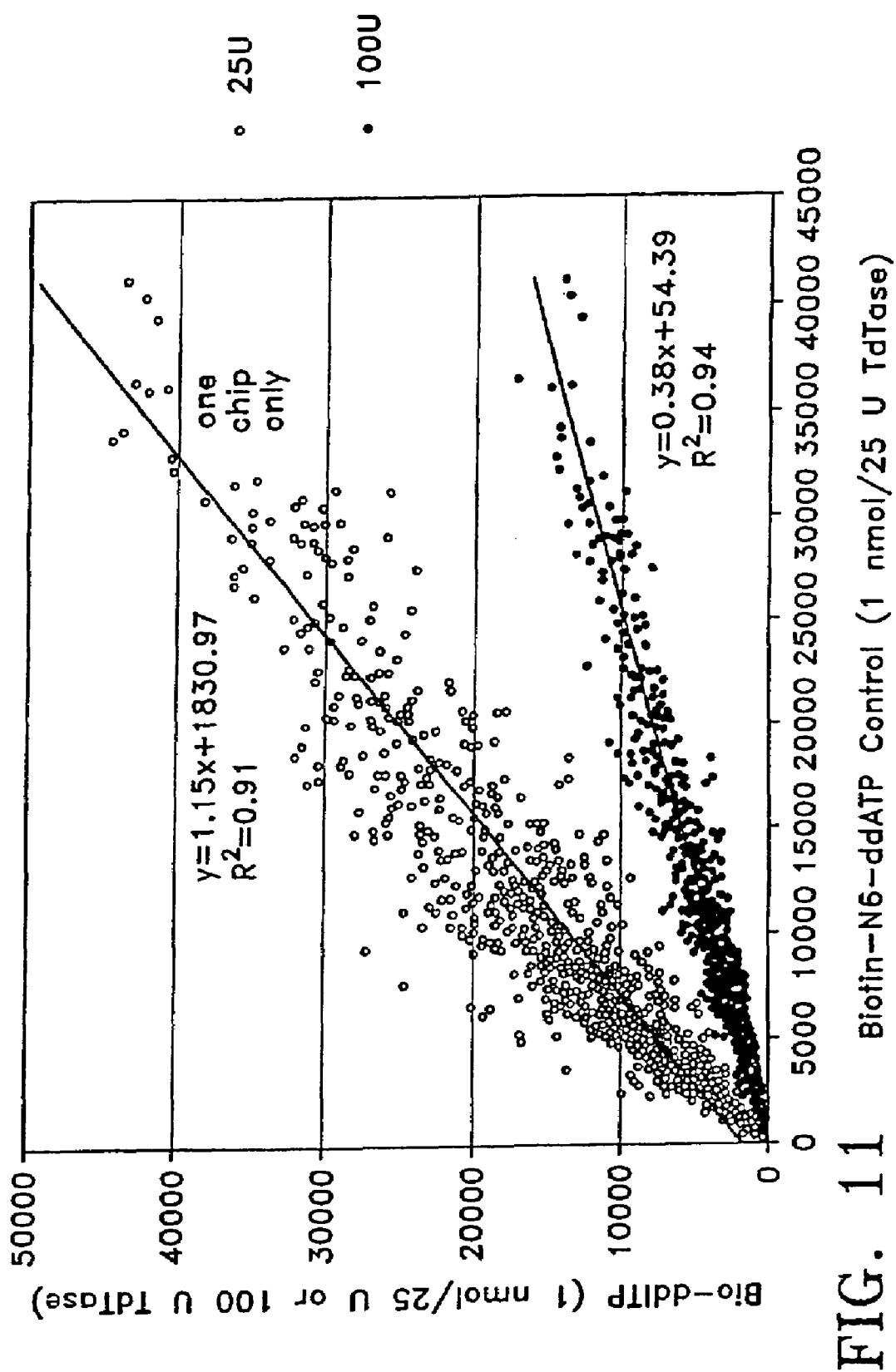
FIG. 11 shows graphical comparisons of observed hybridization fluorescence intensities using Biotin-M-ddITP (wherein M=aminocaproyl) and Biotin-N6-ddATP.

FIG. 11 shows comparisons of the observed hybridization fluorescence intensities for the 1300 bases called in the "Unit-2" part of the chip. In the lower plot, intensities for the Biotin-M-ddITP (8a, M=aminocaproyl; referred to as Bio-ddITP in FIG. 11) labeled targets are plotted against those for the standard Biotin-M-N6-ddATP labeled control targets, both at 25 U of TdT. The observed slope of ~0.4 indicates that the labeling efficiency with 8a was about 40% of that of Biotin-M-N6-ddATP under these conditions. In the upper plot, the same comparison is made, except that 100 U of TdT was used in the 8a labeling reaction. The slope of ~1.1 indicates equivalent or slightly better labeling than the standard Biotin-M-N6-ddATP/25 U control reaction.

Figure 12:
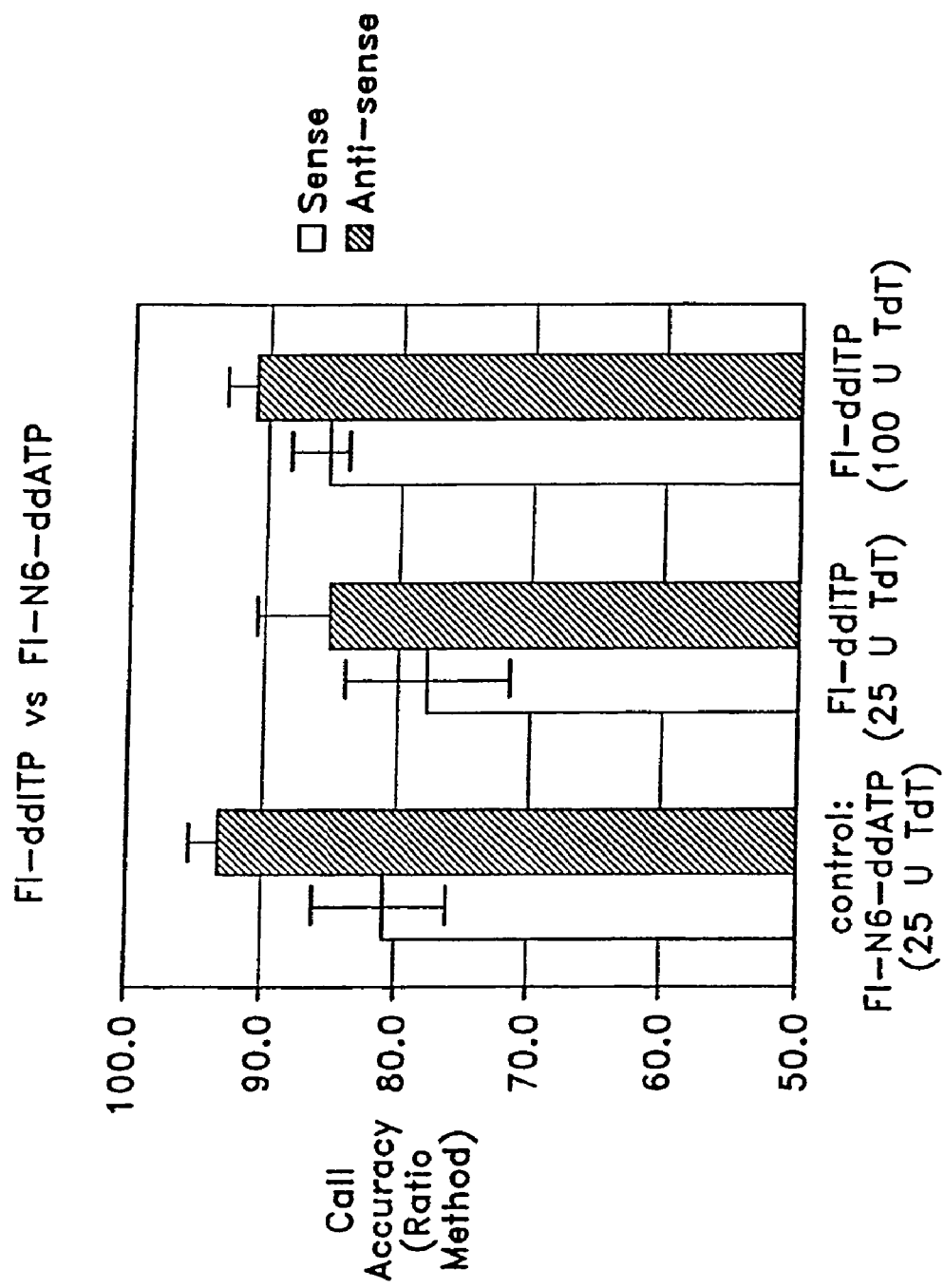
FIG. 12 shows a graphical comparison of overall re-sequencing (base-calling) accuracy using Fluorescein-ddITP and Fluorescein-N6-ddATP labeled targets.
Figure 13:
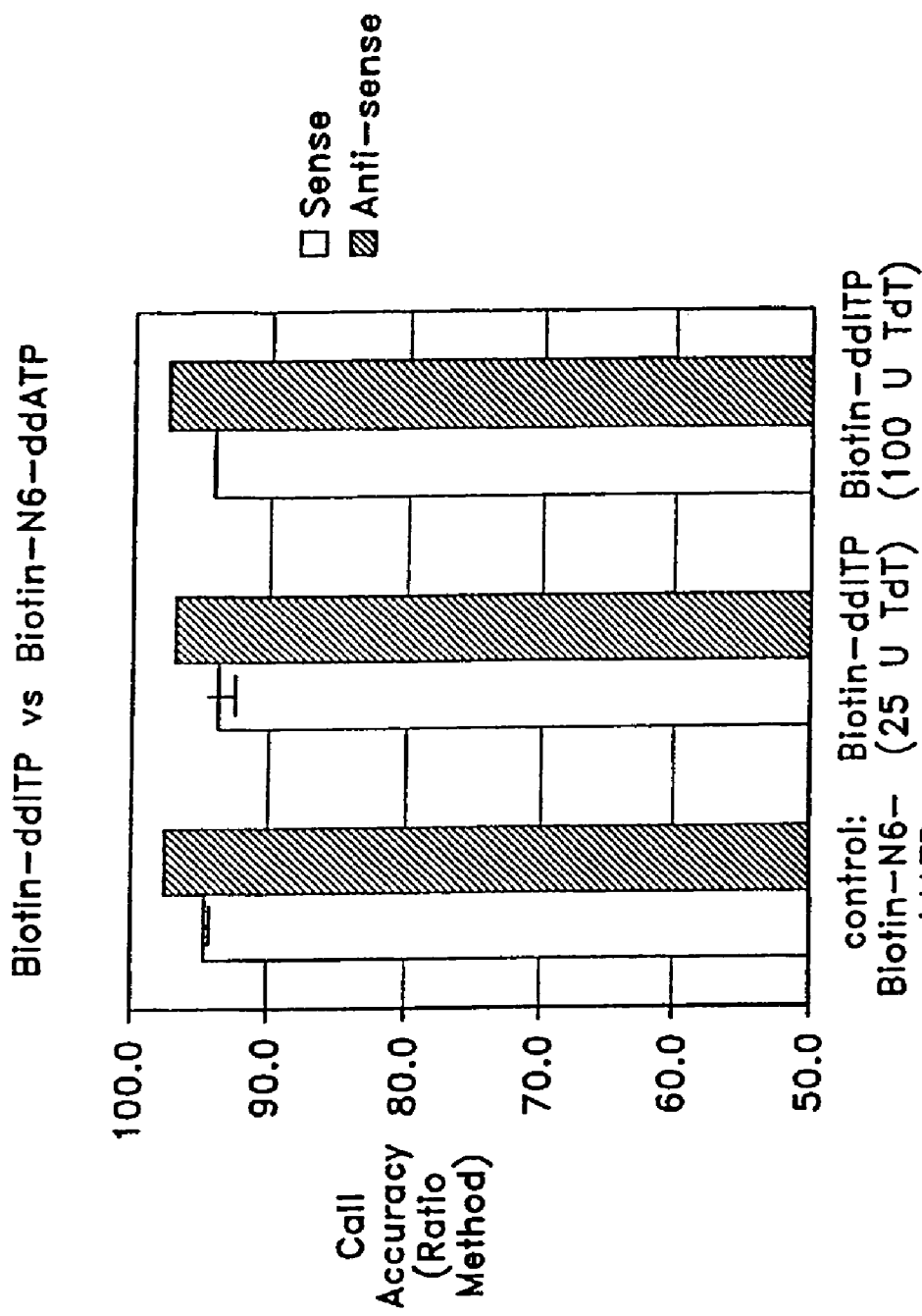
FIG. 13 shows a graphical comparison of overall re-sequencing accuracy using Biotin-M-ddITP (wherein M=aminocaproyl) and Biotin-N6-ddATP.
Figure 14:
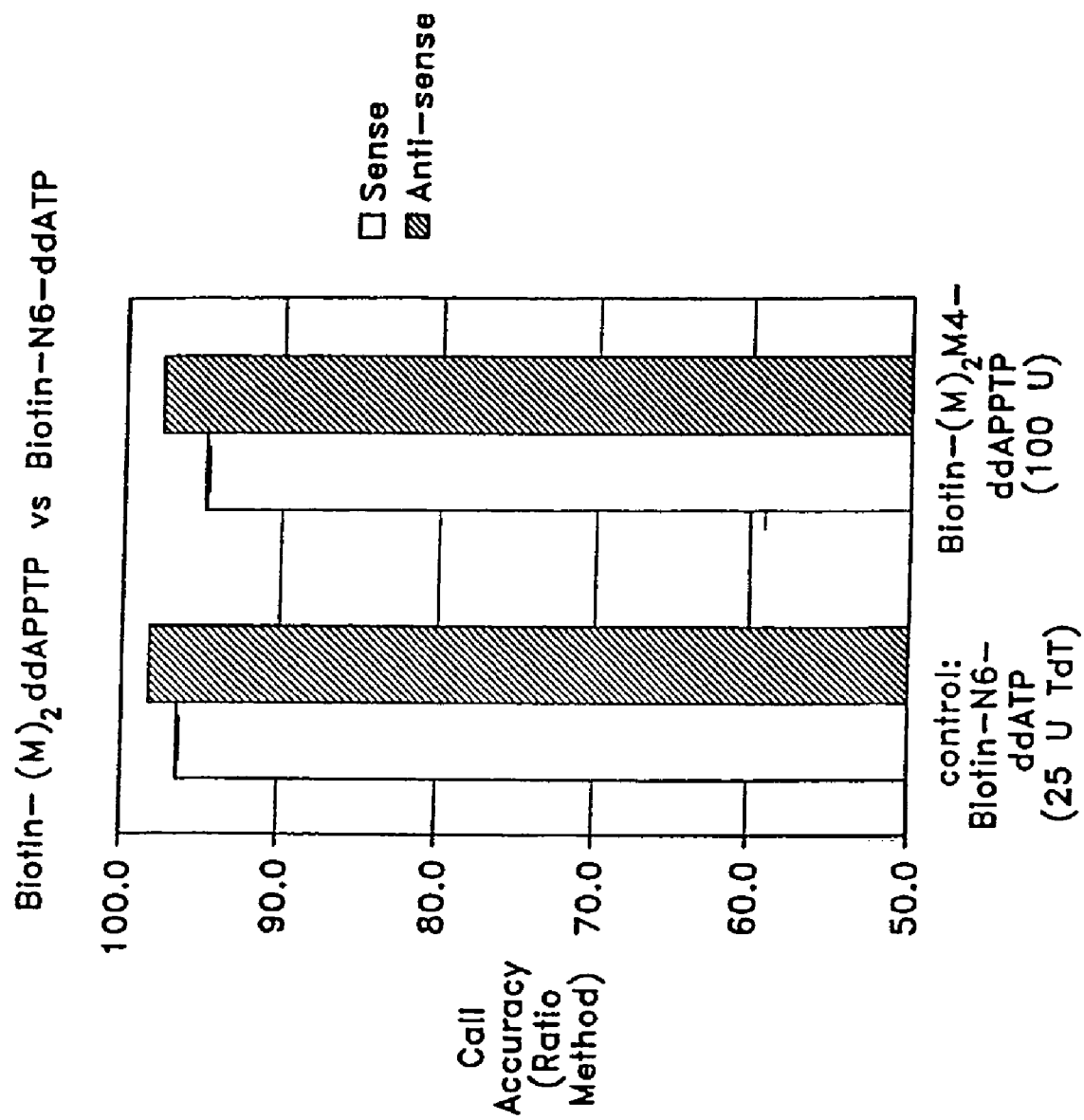
FIG. 14 shows a graphical comparison of re-sequencing accuracy using Biotin-(M)$_2$-ddAPPTP (wherein M=aminocaproyl) and Biotin-N6-ddATP.
Figure 15:
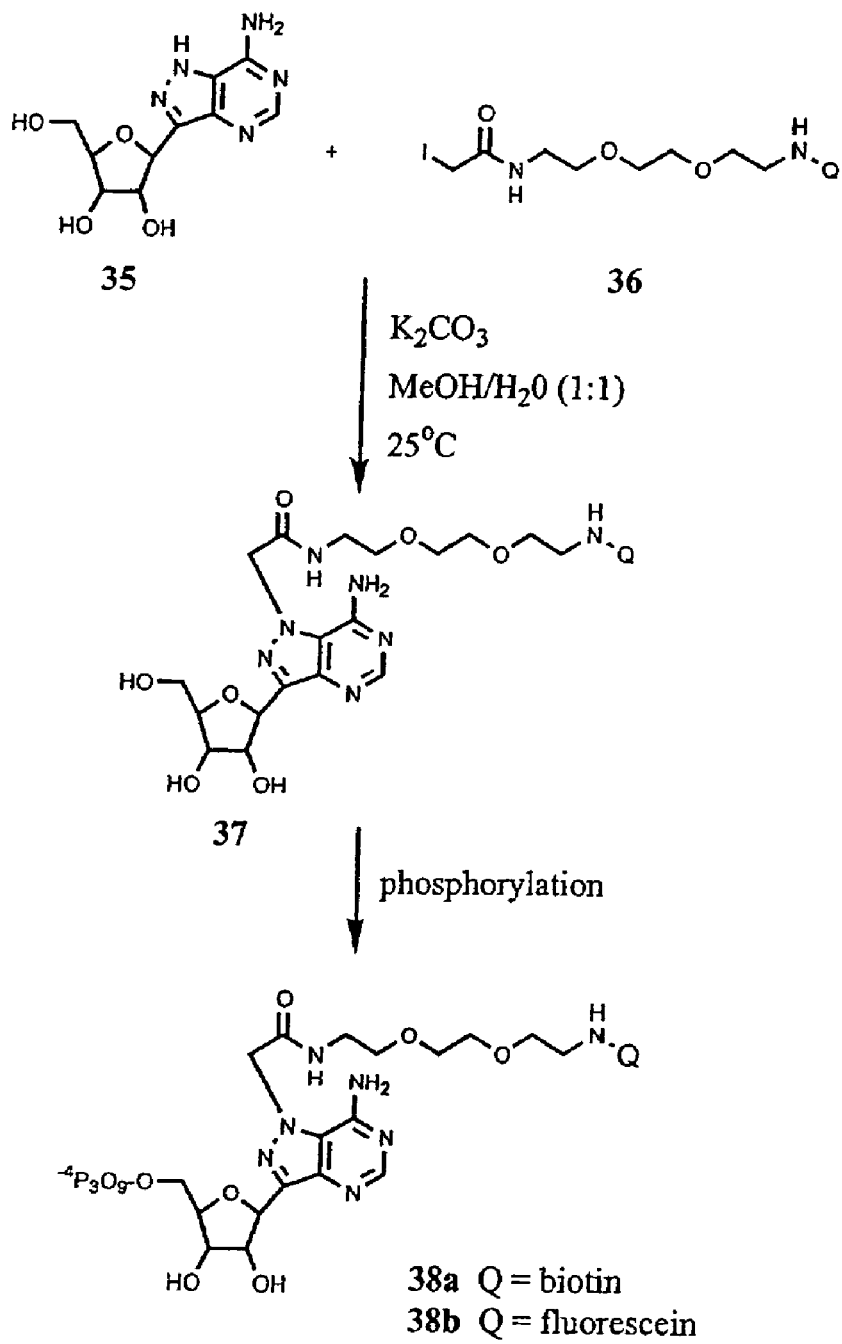
FIG. 15 shows a schematic for the preparation of N1-labeled 3-(β-D-ribofuranosyl)-1H-pyrazalo-[4,3-d]pyrimidine 5'-triphosphate.

FIG. 12 shows a comparison of the overall re-sequencing (base-calling) accuracy, for both strands, obtained using Fluorescein-ddITP labeled targets at both 25 U and 100 U of TdT, as well as the standard Fluorescein-N6-ddATP/25 U TdT labeled "control" targets. FIG. 13 shows a similar comparison for the targets labeled with biotin-M-ddITP (8a; referred to as Biotin-ddITP in FIG. 13) and biotin-M-N6-ddATP "control," followed by PESA staining. FIG. 14 shows a comparison of re-sequencing accuracy using Biotin-(M)₂-ddAPPTP/100 U TdT and Biotin-M-N6-ddATP/25 U TdT. These data indicate that labeled imidazolecarboxamide and 4-aminopyrazolo[3,4-d]pyrimidine dideoxynucleotide analogs can be used for DNA target labeling in hybridization-based assays and give equivalent performance to the standard labeled-N6-ddATP reagent.

Example 9

The performance of the biotin-labeled imidazolecarboxamide and 4-aminopyrazolo[3,4-d]pyrimidine nucleotides ("biotin-M-ITP" (8a) and "biotin-(M)₂-APPTP" (18c)) was evaluated using a single-nucleotide polymorphism genotyping GeneChip® chip array. Published protocols (D. G. Wang, et al., 1998, Science 280: 1077-82.) were used in these experiments, except for the following variations: 1) labeling reactions were carried out using both the standard amount of TdT enzyme specified in the published protocol (15U), or three-fold (45 U) enzyme; 2) substitution of the labeled nucleotide analog for the standard labeling reagent (Biotin-N6-ddATP, from NEN: P/N NEL-508); 3) the labeled nucleotide analog was used at either twice the standard concentration specified in the published protocol (25 uM), or at six-fold (75 uM). After labeling, biotin-labeled targets were hybridized to the arrays, stained with a phycoerythrin-streptavidin conjugate (PE-SA), and the array was scanned and analyzed according to the published procedure.

The data is shown in the Table 4 below. As indicated by the mean intensities of the observed hybridization signal (averaged over the entire array), labeling efficiency with biotin-M-ITP (8a) at 25 uM was as good as Biotin-N6-ddATPat 12.5 uM, and even higher intensity was gained by using 8a at 75 uM (entries 1-3; 7,8). Compared with the control, this analog provided equivalent or better assay performance, expressed as the ratio of correct base calls. Somewhat lower mean signal intensities are observed with biotin-(M)₂-APPTP (18c), reflecting the lower incorporation efficiency of this analog, but equivalent assay performance could still be achieved with this analog, using somewhat higher enzyme and nucleotide concentrations (entries 3-6).

TABLE 4

Comparison of Polymorphism Chip Data

| Entry | Sample | Nucleotide | [Nucleotide] | Units TdT | Mean Intensity | Correct Base Call Ratio |
|---|---|---|---|---|---|---|
| 1 | A | Biotin-M-ddIcTP (8a) | 75 | 15 | 164 | 0.98 |
| 2 | A | Biotin-M-ddIcTP (8a) | 75 | 45 | 235 | 0.98 |
| 3 control | B | Biotin-N6-M-ddATP (NEL 508) | 12.5 | 15 | 138 | 0.95 |
| 4 | B | Biotin-N4-(M)₂-ddAppTP (18c) | 25 | 15 | 37 | 0.88 |
| 5 | B | Biotin-N4-(M)₂-ddAppTP (18c) | 75 | 15 | 35 | 0.92 |
| 6 | B | Biotin-N4-(M)₂-ddAppTP (18c) | 75 | 45 | 87 | 0.95 |
| 7 | B | Biotin-M-ddIcTP (8a) | 25 | 15 | 116 | 0.95 |
| 8 | B | Biotin-M-ddIcTP (8a) | 75 | 15 | 149 | 0.95 |

Example 10

High-density DNA probe arrays are proving to be a valuable tool for hybridization-based genetic analysis. These assays require covalent labeling of nucleic acid molecules with fluorescent or otherwise detectable molecules in order to detect hybridization to the arrays. We have pursued a program to develop a set of novel nucleotide analogs for enzymatic labeling of nucleic acid targets for a variety of array-based assays. Our primary goal was to provide new reagents for two particular labeling procedures: (i.), 3' end labeling of fragmented, PCR-generated DNA targets with terminal deoxynucleotidyl transferase (TdT); and (ii.), template-directed internal labeling of in vitro transcription-generated RNA targets with T7 RNA polymerase (T7).

The general approach taken was to screen various base-substituted nucleotide analogs, using a rapid and quantitative HPLC-based assay, to empirically determine which analogs were efficient substrates for the polymerase of interest. The analogs selected for this study were nucleotides in which the native heterocyclic base was substituted with the following: 1-(imidazole-4-carboxamide), 1-(1,3,6-trazine-2,4-dione), 5-(1,3-pyrimidine-2,4-dione), 3-(pyrazalo-[4,3-d]pyrimidine), 1-(pyrazalo-[3,4-d]pyrimidine) and a simple carboxamide moiety. Labeled versions of promising candidate molecules were then designed and synthesized for further testing of relative incoproation efficiency and functional performance in array-based assays.

It was determined that TdT was generally tolerant of base substitutions, and that ribonucleotides were about as efficiently incorporated as 2'-deoxy, and 2',3'-dideoxynucleotides. In contrast, T7 was relatively intolerant of heterocyclic base substitutions with the exception of the 5-(1,3- pyrimidine-2,4-dione), i.e. the pseudo-uridine analog. Two new reagents, a C4-labeled 1-(2',3'-didexoy-∃-D-ribofuranosyl) imidazole-4 carboxamide 5'-triphophate and an N1-labeled pseudo-uridine 5'-triphophate, were found to be excellent substrates for TdT andT7, respectively. These new analogs prove array assay performance equivalent to that obtained using conventional labeling reagents.

Example 11

Synthesis of Fluorescent Triphosphate Labels

To 0.5 μmoles (50 μL of a 10 mM solution) of the amino-derivatized nucleotide triphosphate, 3'amino-3'deoxythymidinetriphosphate (1) or 2'-amino-2'-deoxyuridine triphosphate (2), in a 0.5 ml ependorf tube was added 25 μL of 11 M aqueous solution of sodium borate, pH 7, 87 μL of methanol, and 88 μL (10 μmol, 20 wquiv) of a 100 mM solution of 5-carboxyfluorescein-X-NHS ester in methanol. The mixture was vortexed briefly and allowed to stand at room temperature in the dark for 15 hours. The sample was then purified by ion-exchange HPLC to afford the fluoresceinated derivatives Formula 3 or Formula 4, below, in about 78-84% yield.

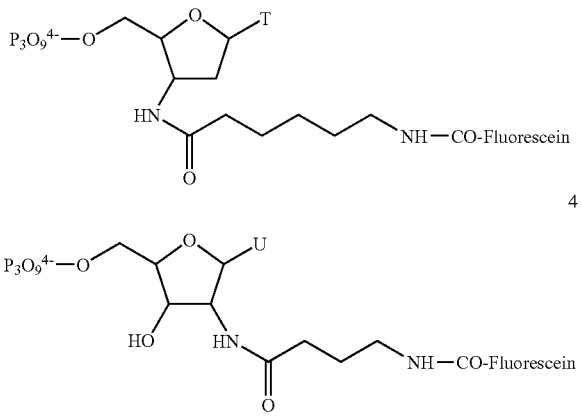

Experiments suggest that these molecules are not substrates for terminal transferase (TdT). It is believed, however, that these molecules would be sutstrates for a polymerase, such as klenow fragment.

Example 12

Synthesis of as-Triazine-3,5[2H,4H]-diones

The analogs as-triazine-3,5[2H,4H]-dione ("6-aza-pyrimidine") nucleotides (see, FIG. 23a) are synthesized by methods similar to those used by Petrie, et al., *Bioconj. Chem.* 2: 441 (1991).

Other useful labeling reagents are sythesized including 5-bromo-U/dUTO or ddUTP. See for example Lopez-Canovas, L. Et al., *Arch. Med. Res* 25: 189-192 (1994); Li, X., et al., *Cytometry* 20: 172-180 (1995); Boultwood, J. Et al., *J. Pathol.* 148: 61 ff. (1986); Traincard, et al., *Ann. Immunol.* 1340: 399-405 (1983); and FIGS. 23a, and 23b set forth herein.

Details of the synthesis of nucleoside analogs corresponding to all of the above structures (in particular those of FIG. 23b) have been described in the literature Known procedures can be applied in order to attach a linker to the base. The linker modified nucleosides can then be converted to a triphosphate amine for final attachment of the dye or hapten which can be carried out using commercially available activated derivatives.

Other suitable labels include non-ribose or non-2'-deoxyribose-containing structures some of which are illustrated in FIG. 23c and sugar-modified nucleotide analogues such as are illustrated in FIG. 23d.

Using the guidance provided herein, the methods for the synthesis of reagents and methods (enzymatic or otherwise) of label incorporation useful in practicing the invention will be apparent to those skilled in the art. See, for example, *Chemistry of Nucleosides and Nucleotides* 3, Townsend, L. B. ed., Plenum Press, New York, at chpt. 4, Gordon, S. The Synthesis and Chemistry of Imidazole and Benzamidizole Nucleosides and Nucleotides (1994); Gen Chem. *Chemistry of Nucleosides and Nucleotides* 3, Townsend, L. B. ed., Plenum Press, New York (1994);

can be made by methods simliar to those set forth in *Chemistry of Nucleosides and Nucleotides* 3, Townsend, L. B. ed., Plenum Press, New York, at chpt. 4, Gordon, S. "The Synthesis and Chemistry of Imidazole and Benzamidizole Nucleosides and Nucleotides (1994); Lopez-Canovas, L. Et al., *Arch. Med. Res* 25: 189-192 (1994); Li, X., et al., *Cytometry* 20: 172-180 (1995); Boultwood, J. Et al., *J. Pathol.* 148: 61 ff. (1986); Traincard, et al., *Ann. Immunol.*1340: 399-405 (1983).

Example 13

Figure 16:
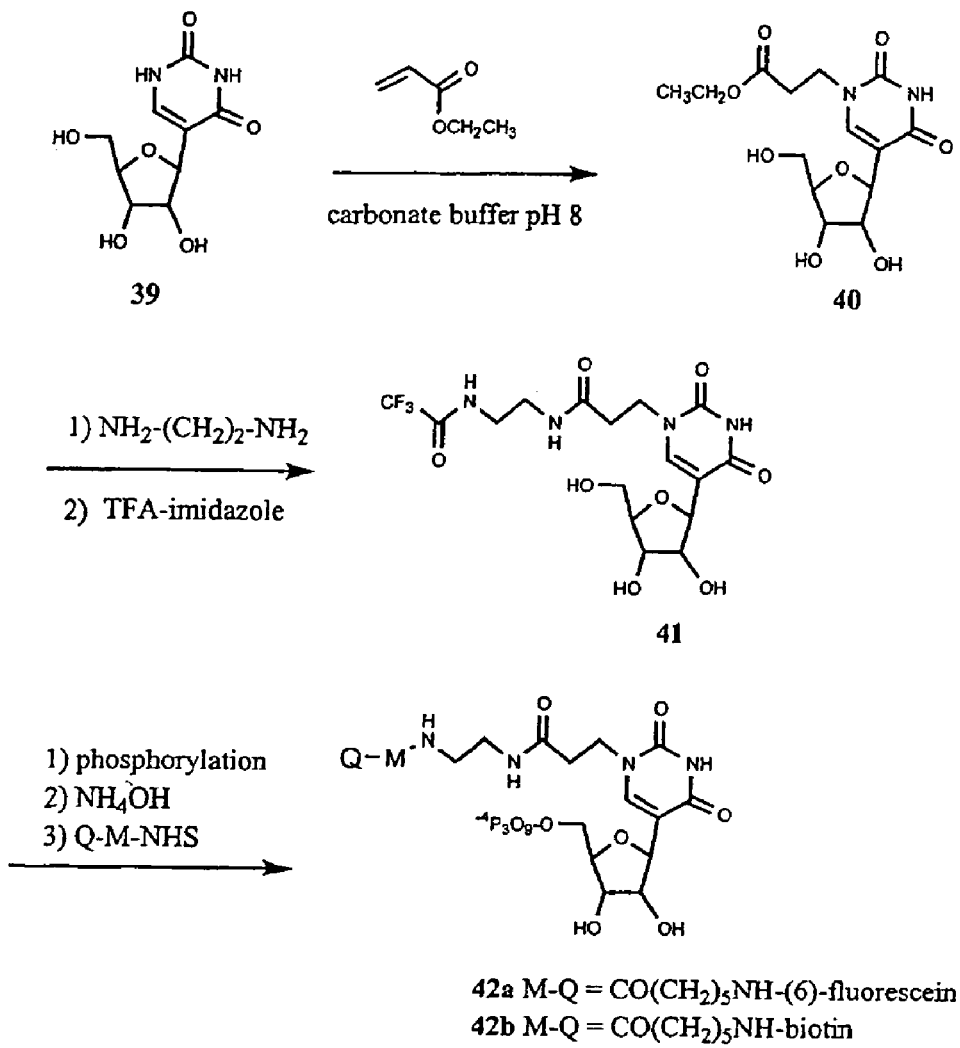
FIG. 16 shows a schematic for the preparation of N1-labeled 5-(β-D-ribofuranosyl)-2,4[1H,3H]-pyrimidinedione 5'-triphosphate.

Synthesis of N1-labeled 5-(β-D-ribofuranosyl)-2,4 (1H, 3H)-pyrimidinedione 5'-triphosphate 42a and 42b (FIG. 16)

To 5-(β-D-ribofuranosyl)-2,4(1H,3H)-pyrimidinedione 39 (100 mg, 0.41 mmol, 1 eq.) in acetonitrile (5 ml) was added 1 M TEAB, pH 9 (5 ml) followed by methyl acrylate (5.5 ml, 61 mmol, 150 eq). The reaction was stirred at room temperature overnight. The solvents were evaporated, and the residue was coevaporated with water (3×, 5 ml) yielding 135 mg of acrylate 40. The acrylate 40 was then treated with neat ethylenediamine (2 ml, excess) and two drops of TEA and heated to 100° C. After 1 hour the excess EDA was evaporated, yielding 146 mg of the free amine (quantitative). The crude residue was then co-evaporated with pyridine (3×, 5 ml, insoluble), resuspended in a mixture of pyridine and DMF and was cooled to 0° C. To this mixture was added TFA-imidazole (73.8 mg, 1.1 eq.). The reaction was then allowed to warm to room temperature and stirred overnight. An additional 1 eq. of TFA-imidazole was added at this time and the reaction was stirred an additional 15 minutes. The solvent was then evaporated, and the residue was co-evaporated with water(2×, 5 ml) and dissolved in 5 ml of water. The white precipitate that formed was removed by filtration. The mother liquor, which contained the TFA-protected nucleoside 3, was separated into two aliquots and purified by reverse phase HPLC. The fractions were then pooled and evaporated to yield 20% (35 mg) of pure 41, which was verified by 'H NMR. Using standard procedures (eg., Prober, et al., EP 0252683), compound 41 was converted to the triphosphate, which was then conjugated to biotin and fluorescein to afford 42a and 42b.

Synthesis of the N1-labeled 2-amino-5-(β-D-ribofuranosyl)-4(1H)-pyrimidinone, 55, involved alkylation at N1 using conditions similar to those described by Muehlegger, et al. (WO 96/28640) for the N1-alkylation of pyrazalo-[4, 3-d]pyrimidines (Scheme 2).

The IVT incorporation efficiency (the number of labeled analogs incorporated per transcript) of the N1-fluorescein-X-5-(β-D-ribofuranosyl)-2,4(1   H,3H)-pyrimidinedione 5′-triphosphate 42a was measured by HPLC (diode array UV detection at 260 nm and 495 nm) in an IVT amplification of a 1.24 kb transcript. See U.S. patent application Ser. No. 09/126,645 for additional details on test methods used. Table 1 summarizes the data obtained using different ratios of UTP/5 At a ratio of 1:5, the incorporation and relative yield (measured relative to the yield obtained with UTP only) of transcript are optimal. This transcript was compared in a hybridization assay to transcript labeled using fluorescein. The preliminary results indicated that the N1-fluorescein-X-5-(β-D-ribofuranosyl)-2,4(1H,3H)-pyrimidinedione 5′-triphosphate (42a) performed equivalently in a hybridization assay in terms of number of correct calls and in hybridization intensity (Charts 2 and 3). The hybridization assay used for this purpose was the Affymetrix HIV-PRT GeneChip assay (see Kozal, et al. Nature Medicine 1996, 2: 753-9.).

Similarly, the efficiency of DNA 3′-end labeling of a polythymidylate oligonucleotide ($T_{16}$) using terminal deoxynucleotidyl transferase and N1-fluorescein and biotin-labeled 5-(β-D-ribofuranosyl)-2,4(1H,3H)-pyrimidinedione 5′-triphosphate, was determined by HPLC. In this analysis, the percent conversion of oligo-$T_{16}$ to the 3′-end labeled $T_{16}$-Fl, is determined by AX-HPLC (see U.S. patent application Ser. No. 09/126,645 for detailed procedures). The data is summarized in Chart 4. The incorporation of the biotin and fluorescein triphosphates was very efficient as determined by HPLC.

Scheme 2

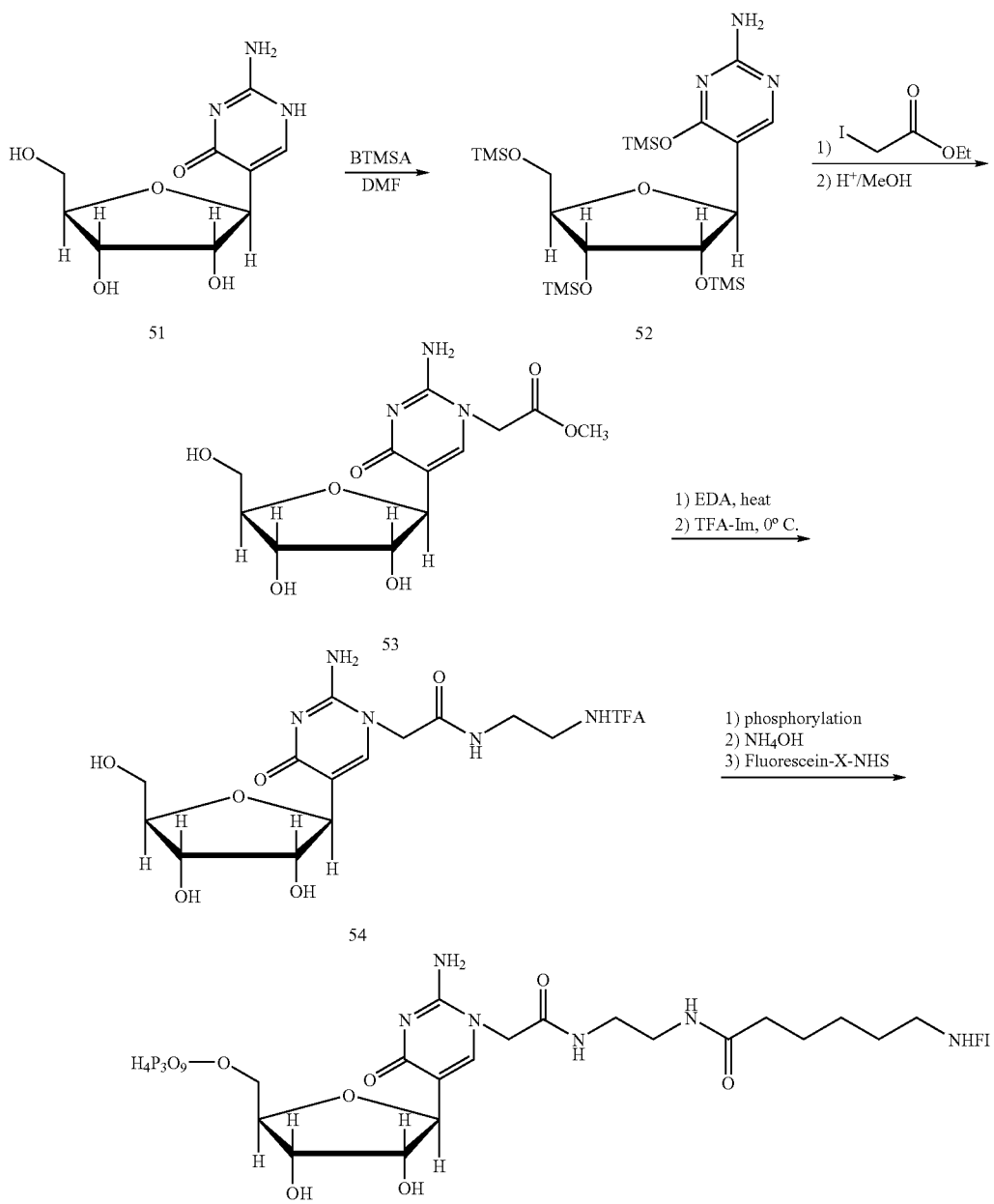

Chart 1. Incorporation efficiency of N1-fluorescein-labeled 5-(β-D-ribofuranosyl)-2,4(1H,3H)-pyrimidinedione 5'-triphosphate 42a, determined by HPLC

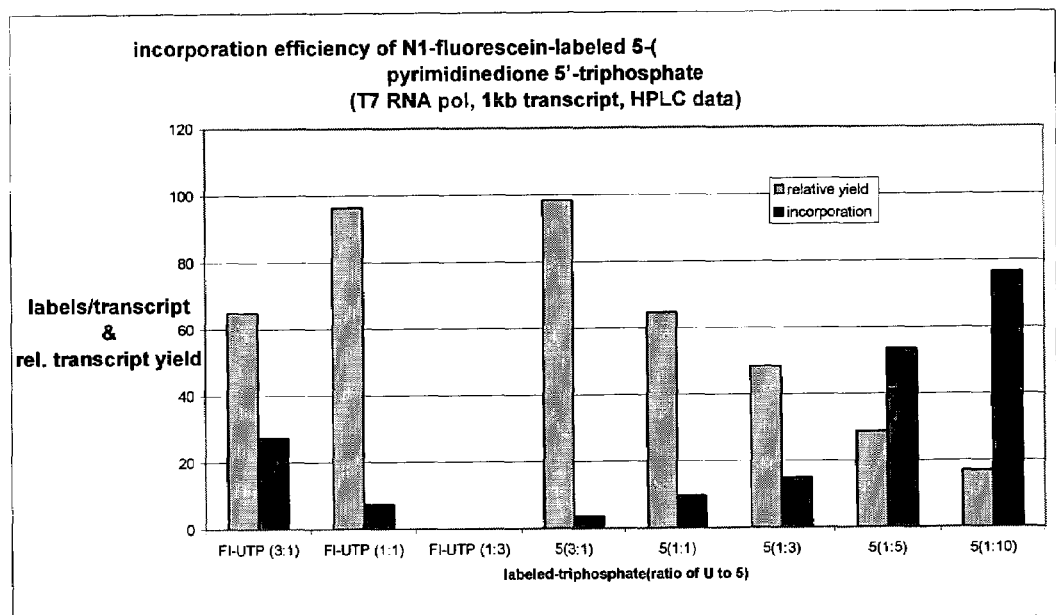

The labeling reaction conditions are the standard conditions used in the Affymetrix HIV-PRT GeneChip product assay (see Kozal, et al. Nature Medicine 1996, 2: 753-9.).

Chart 2. Call accuracy of N1-fluorescein-labeled 5-(β-D-ribofuranosyl)-2,4(1H,3H)-pyrimidinedione 5'-triphosphate 42a.

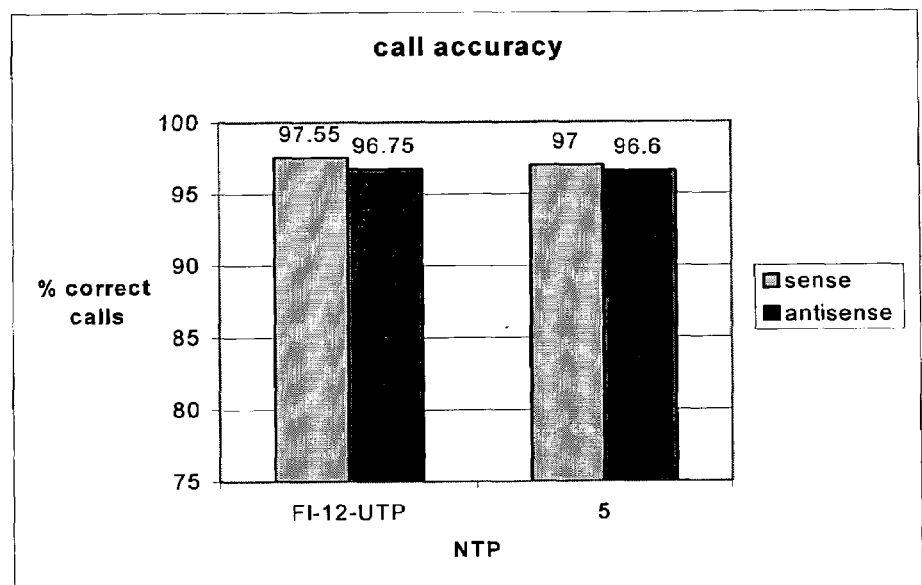

Data was obtained from Affymetrix HIV-PRT GeneChip hybridization assay (see Kozal, et al. Nature Medicine 1996, 2: 753-9.).
*Chart 3. Hybridization signal of fluorescein labeled triphosphate 42a*
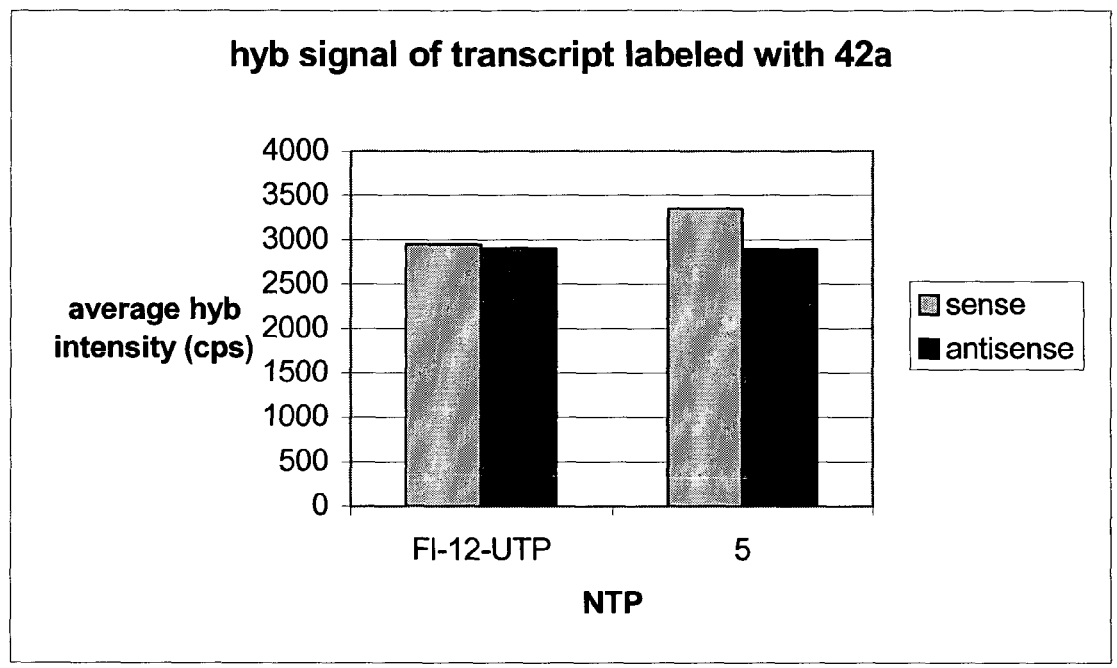
Data obtained from hybridization of labeled transcript to the Affymetrix HIV-PRT GeneChip array (see Kozal, et al. Nature Medicine 1996, 2: 753-9.).

*Chart 4. TdT labeling efficiency of Fluorescein and Biotin labeled 5-(β-D-ribofuranosyl)-2,4(1H,3H)-pyrimidinedione 5'-triphosphate* 42a *and* 42b, *determined by HPLC.*
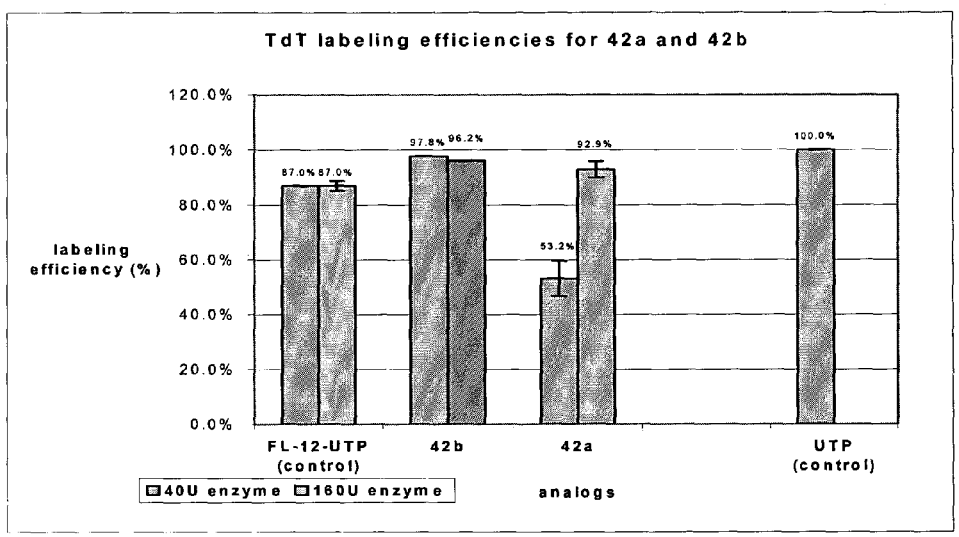
Reaction conditions: TdT (40 units), 20 uM U*TP and 3.2 uM $T_{16}$ oligo in 50 ul of water. Heated at 37°C for 1 hour and 70°C for 10 min., followed by 1 ul of 100 mM EDTA. HPLC analysis was performed on a Dionex DNAPac™ PA-100 column.

Example 14

Synthesis of fluorescein derivatives of 2'-amino-2'-deoxyuridine triphosphate and 3'-amino-3'-deoxythymidinetriphosphate (Scheme 3).

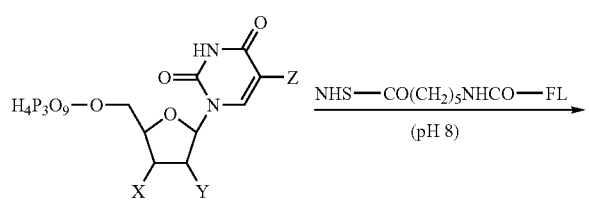

Scheme 3

99 X = OH, Y = NH$_2$ Z = H
98 X = NH$_2$, Y = H, Z = CH$_3$

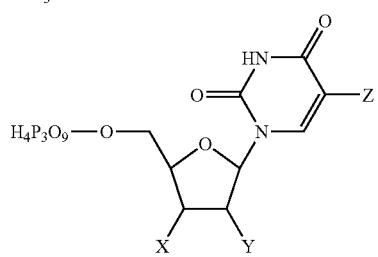

97 X = OH, Y = NHCO(CH$_2$)$_5$NHCOFL, Z = H
96 X = NHCO(CH$_2$)$_5$NHCOFL, Y = H, Z = CH$_3$

To 0.5 umoles (50 uL of a 10 mM solution) of the amino nucleotide triphosphate (1 or 2) in a 0.5 ml ependorf tube was added 25 ul of a 1 M aqueous solution of sodium borate, pH 8, 87 uL of methanol, and 88 uL (10 umol, 20 equiv) of a 100 mM solution of 5-carboxyfluorescein-X-NHS ester in methanol. The mixture was vortexed briefly and allowed to stand at room temperature in the dark for 15 hours. The sample was then purified by ion-exchange HPLC to afford the fluoresceinated derivatives 3 or 4 in about 78-84% yield. Relative efficiencies of incorporation of these compounds by TdT are shown in Table 5.

Example 15

Figure 17:
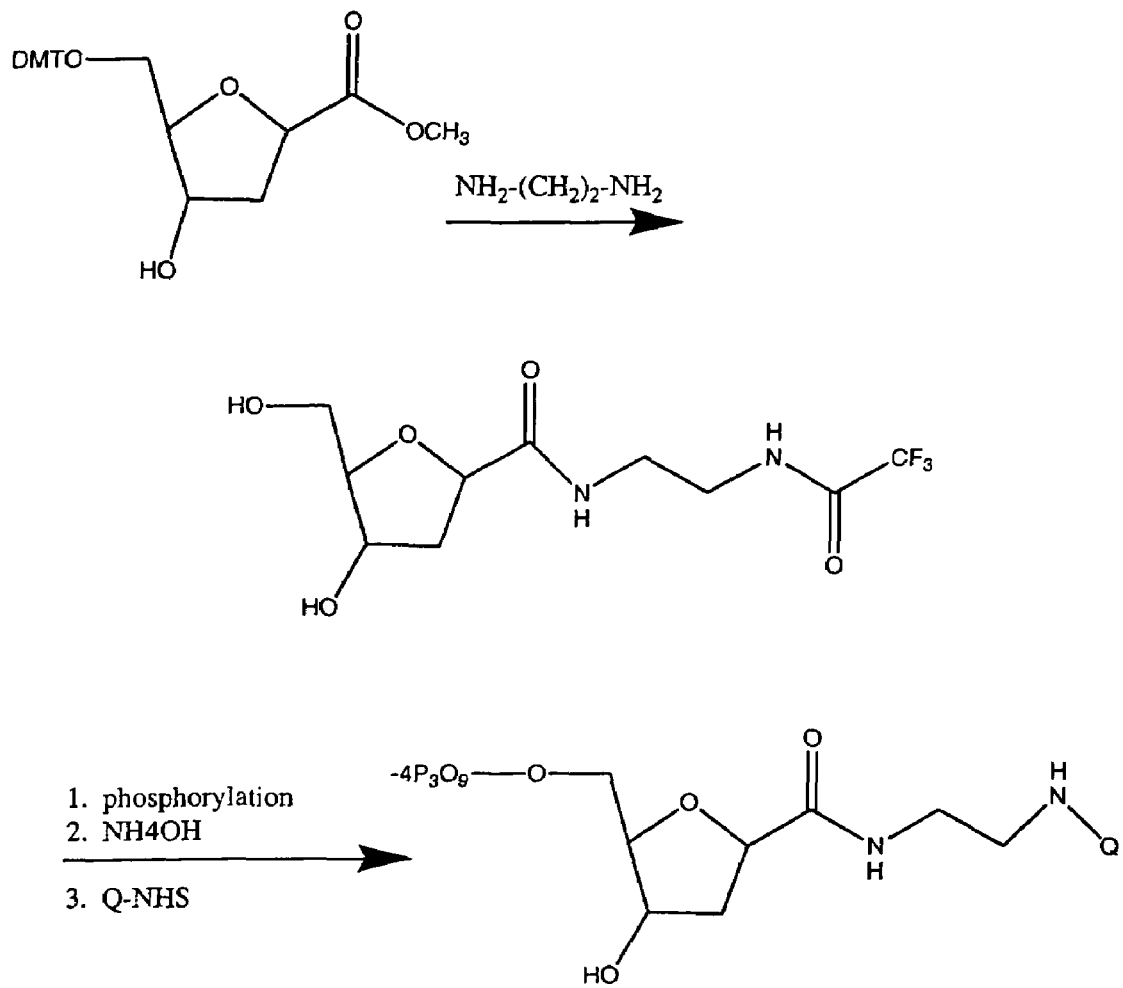
FIG. 17 shows a schematic for the preparation of N-labeled 2,5-anhydro-3-deoxy-D-ribo-hexamide 6-triphosphate.
Figure 18A:
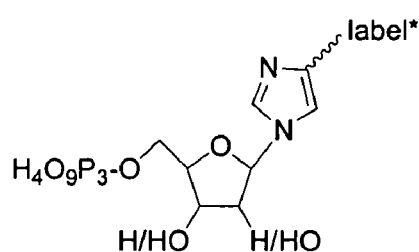
FIG. 18*a* shows various labeling reagents.
Figure 18A:
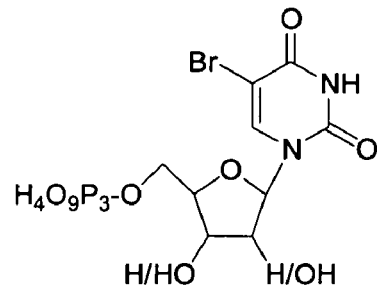
Figure 18A:
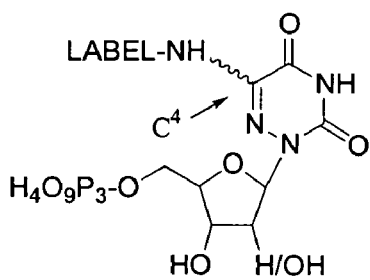
Figure 18A:
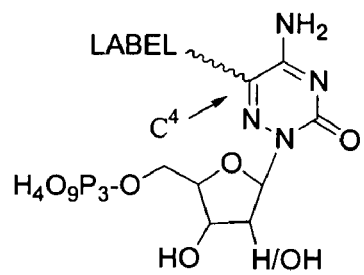
Figure 18A:
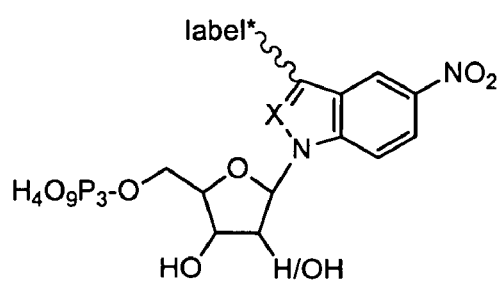
Figure 18A:
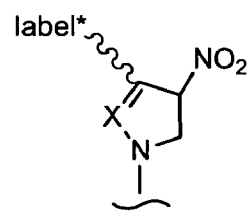
Figure 18A:
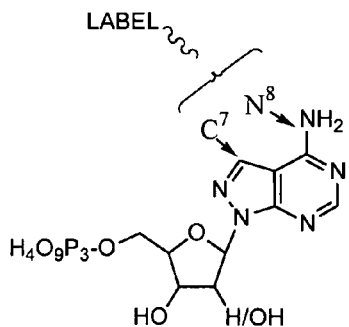
Figure 18A:
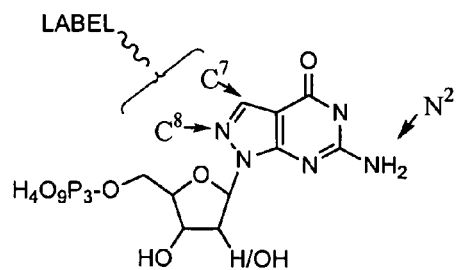
Figure 18B:
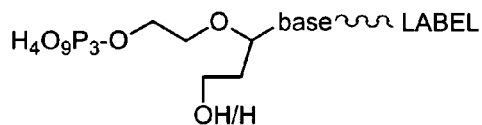
FIG. 18*b* shows still other labeling reagents.
Figure 18B:
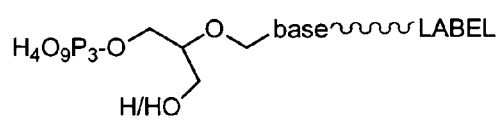
Figure 18B:
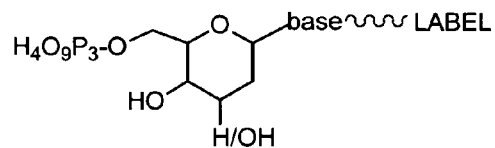
Figure 18B:
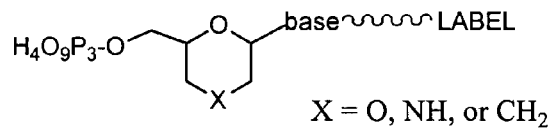
Figure 18B:
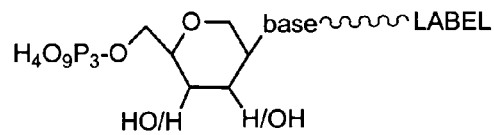
Figure 18B:
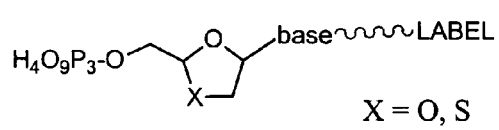
Figure 18B:
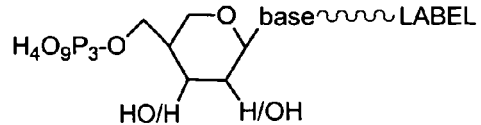
Figure 18C:
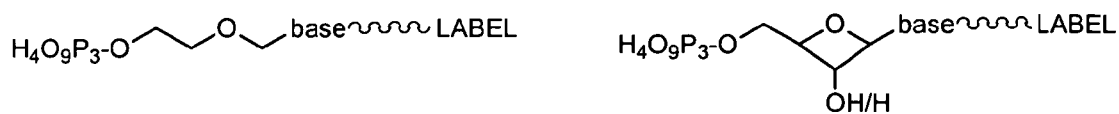
FIG. 18*c* shows non-ribose or non-2'-deoxyribose-containing labels.
Figure 18D:
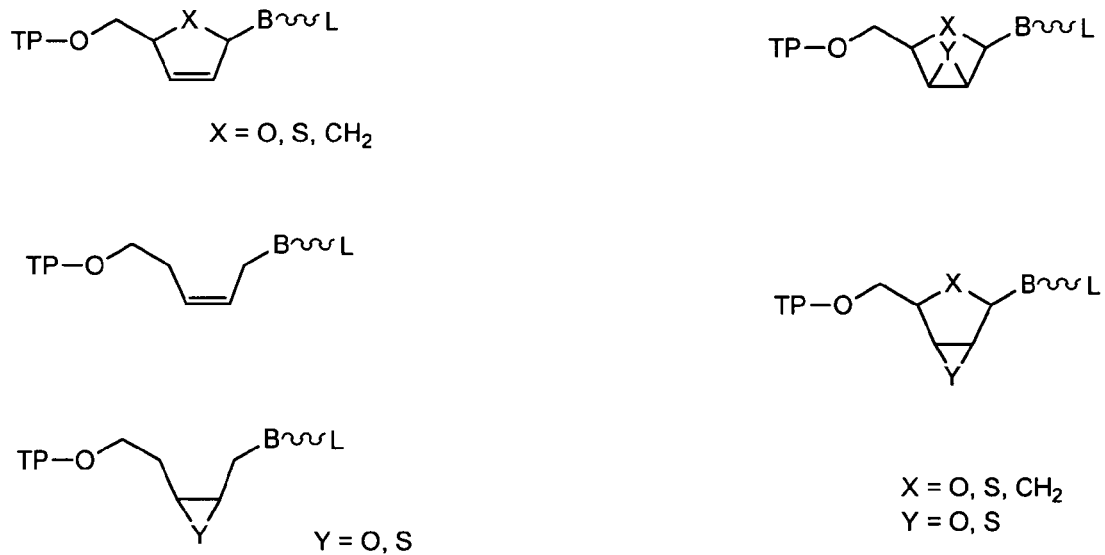
FIG. 18*d* shows sugar-modified nucleotide analogue labels.
Figure 19:
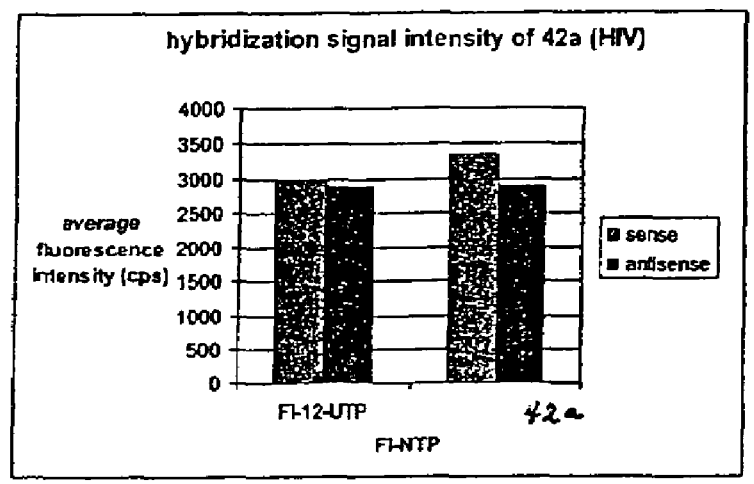
FIG. 19 shows HIV array data for analog 42*a* (T7 labeling of RNA target).
Figure 19:
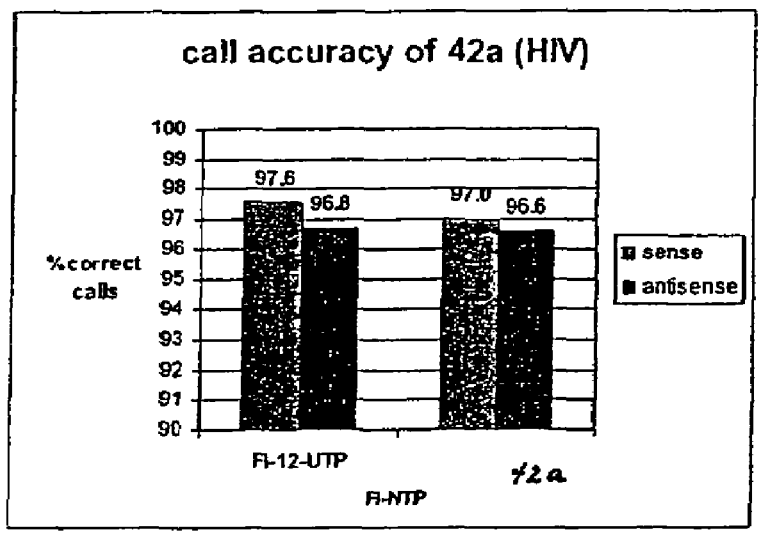
Figure 20:
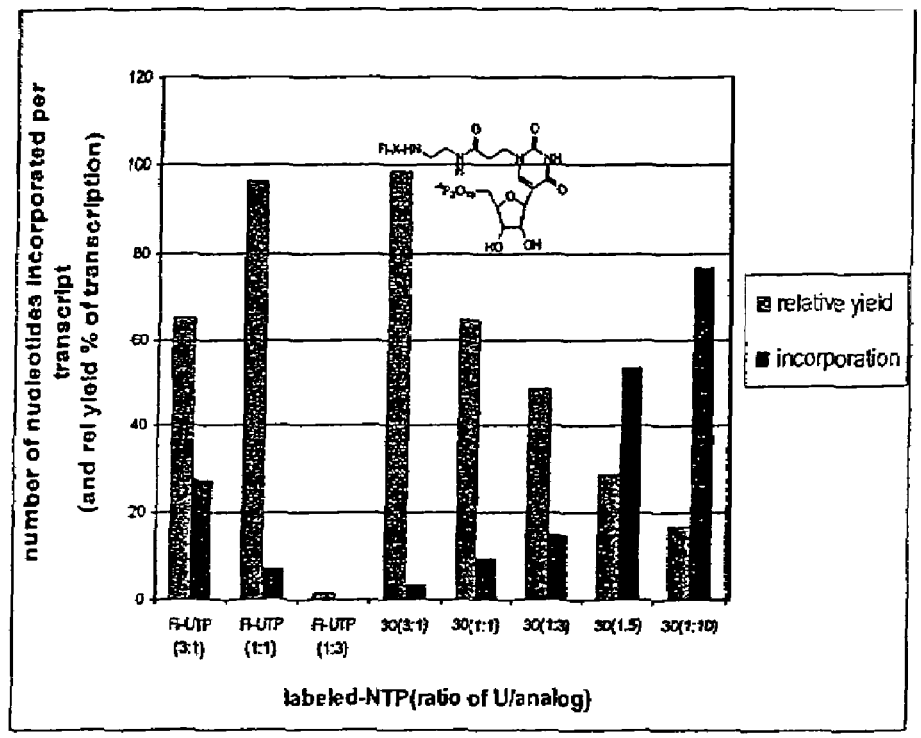
FIG. 20 shows HPLC incorporation efficiency of C-nucleotide 42*a* (T7 RNA pol, 1 kb transcript).

Synthesis of N-(fluorescein-5-carboxamido)ethyl-3-deoxy-allonamide-6-O-triphosphate (FIG. 17)

Ni-(di-O-acetylfluorescein-5-carboxamido)ethyl-3-deoxy-4-O-acetyl-6-O-dimethoxytrityl allonamide 43 (U.S. patent application Ser. No. 08/574,461) was detritylated with 80% acetic acid, and the crude product was purified on a small silica gel column to obtain N1-(di-O-acetylfluorescein-5-carboxamido)ethyl-3-deoxy-4-O-acetyl allonamide 44. The allonamide was phosphorylated using POCl$_3$ followed by reaction with pyrophosphate (Bogachev, Russ. J. Bioorg. Chem. 1996, 22: 559-604). The crude product was treated with NH$_4$OH to remove the acetyl protecting groups, then purified using a preparative Source QTM AX-HPLC column. Pure fractions (analysed by analytical ion-exchange HPLC) were pooled and evaporated to near-dryness. The triphosphate salt 45$a$ was precipitated with MeOH-acetone and dried under high vacuum to obtain a product which was 98% pure by ion-exchange HPLC and 31p NMR.

Example 16

Synthesis of N-(6-fluorescein-5-carboxamido)hexanoyl)-morpholino uridine triphosphate (Scheme 5).

Morpholino-uracil tosylate salt 1 (30 mg) was co-evaporated with pyridine (3×3 ml) and dissolved in 2 ml of pyridine and cooled to 0° C. Trifluoroacetic anhydride (30 uL) was added and stirred for 1 hour. The reaction was followed by HPLC until complete. The pyridine was removed and the residue was dissolved in 1 ml of water and filtered. The product was purified by HPLC on a Waters C-18 bondapak cartridge (Buffer: A=50 mM TEM pH 7.0; B=acetonitrile) using a gradient of 0-25% B in 30 minutes (retention time=22 min.). The product was desalted on a Sep-Pak cartridge and freeze-dried to give 151 mg of 2. Phosphorylation of 2 using the POCl$_3$ method gave 3. The removal of the trifluoroacetyl group with conc. NH$_4$OH at 50° C. for 30 min to 4, followed by conjugation to 5-carboxyfluoroscein-aminocaproic acid N-hydroxysucciimide (Fl-X-NHS) under standard conditions gave the amide 4.

TABLE 5

Incorporation of triphosphate compounds by TdT.

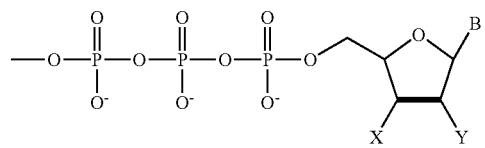

| | TdT Labeling Efficiencies | | % Labeled | |
|---|---|---|---|---|
| X (3') | Y (2') | B (1'b) | 40U | 160U |
| OH | H | Uracil | 100.0 | 100.0 |
| NH2 | H | thymine | 100 | 100 |
| NHCO(CH2)5NH—(CO—FL) | H | thymine | 1.3 | 2.2 |
| OH | NH2 | Uracil | 65 | 95 |
| OH | NHCO(CH2)5NH—(CO—FL) | Uracil | 3.0 | 6.6 |
| OH | O(CH2)6NH—(CO—FL) | Uracil | 2.5 | 7.0 |
| OH | O(CH2)6NHCO—(CH2)5—NHCO-Biotin | Uracil | 15.0 | 17.0 |
| OH | NH(CH2)5CH3 | Uracil | 4.5 | 5.0 |
| OH | H | NHCO(CH2)5NH—(CO—FL) | 45.0 | 55.0 |

The mass spectral and NMR data for compounds 1-5 were consistent with the proposed structures.

Scheme 5

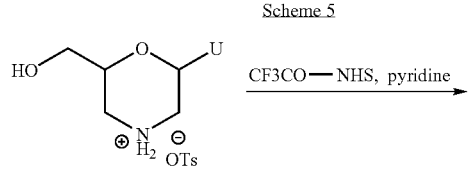

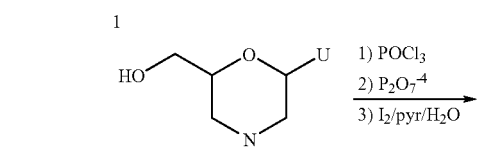

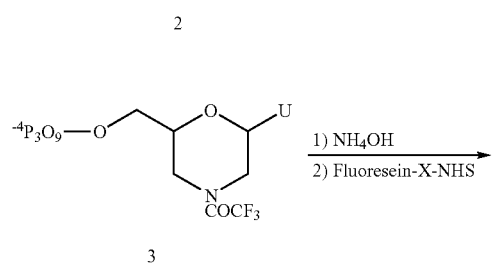

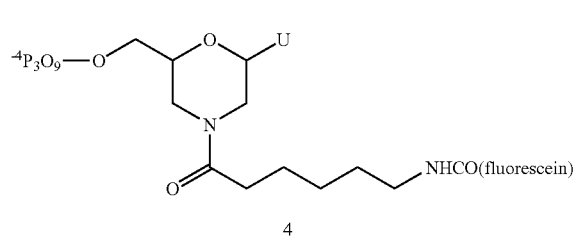

Example 17

Labeled N-(2-hydroxyethoxy)ethyl 2-O-triphosphates (Scheme 6)

Scheme 6

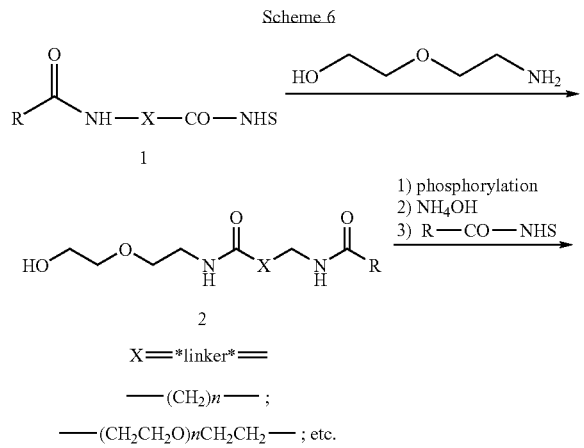

X ═ *linker* ═

—(CH$_2$)$n$—;

—(CH$_2$CH$_2$O)$n$CH$_2$CH$_2$—; etc.

-continued

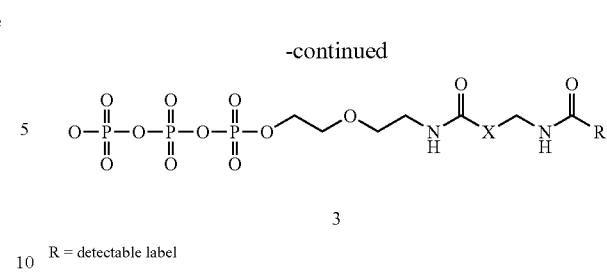

R = detectable label

Example 18

Labeled 2-(2-hydroxyethyl)acetamide 2-O-triphosphates (Scheme 7)

Scheme 7

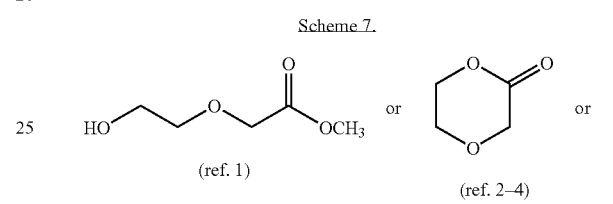

(ref. 1)   (ref. 2–4)

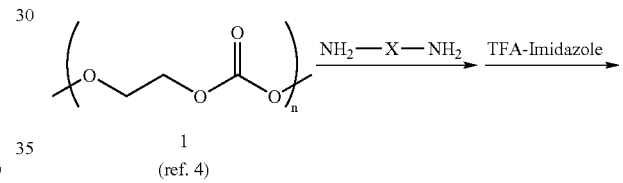

(ref. 4)

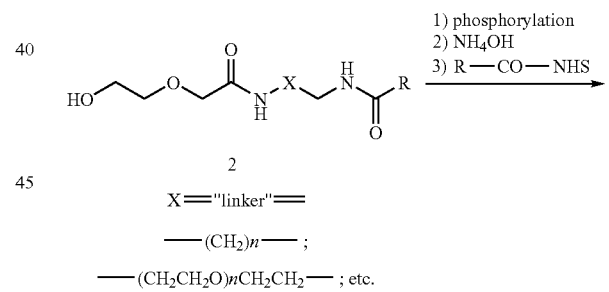

X ═ "linker" ═

—(CH$_2$)$n$—;

—(CH$_2$CH$_2$O)$n$CH$_2$CH$_2$—; etc.

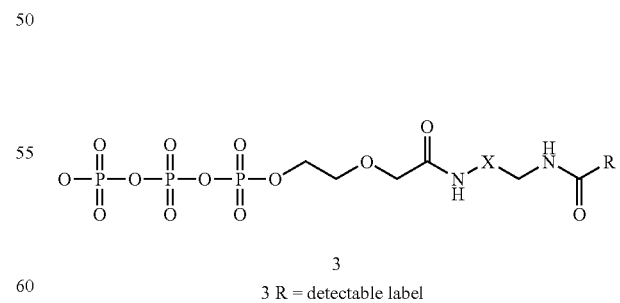

3 R = detectable label

1) Kitano M; Ohashi N (1997) EP 787728 A1
2) Shahi SP, et al. (1999) J. Org. Chem. 64: 4509-11.
3) Nishimura T, et al. (1999) J. Org. Chem. 64: 6750-55.
4) Nishida H, eat al. (2000) J. Polym. Sci. 38: 1560-67.

Each of these references is herein incorporated by reference.

Example 19
Synthesis of N-alkyl 2'-amino-2'-deoxyuridine triphosphate (Scheme 8)
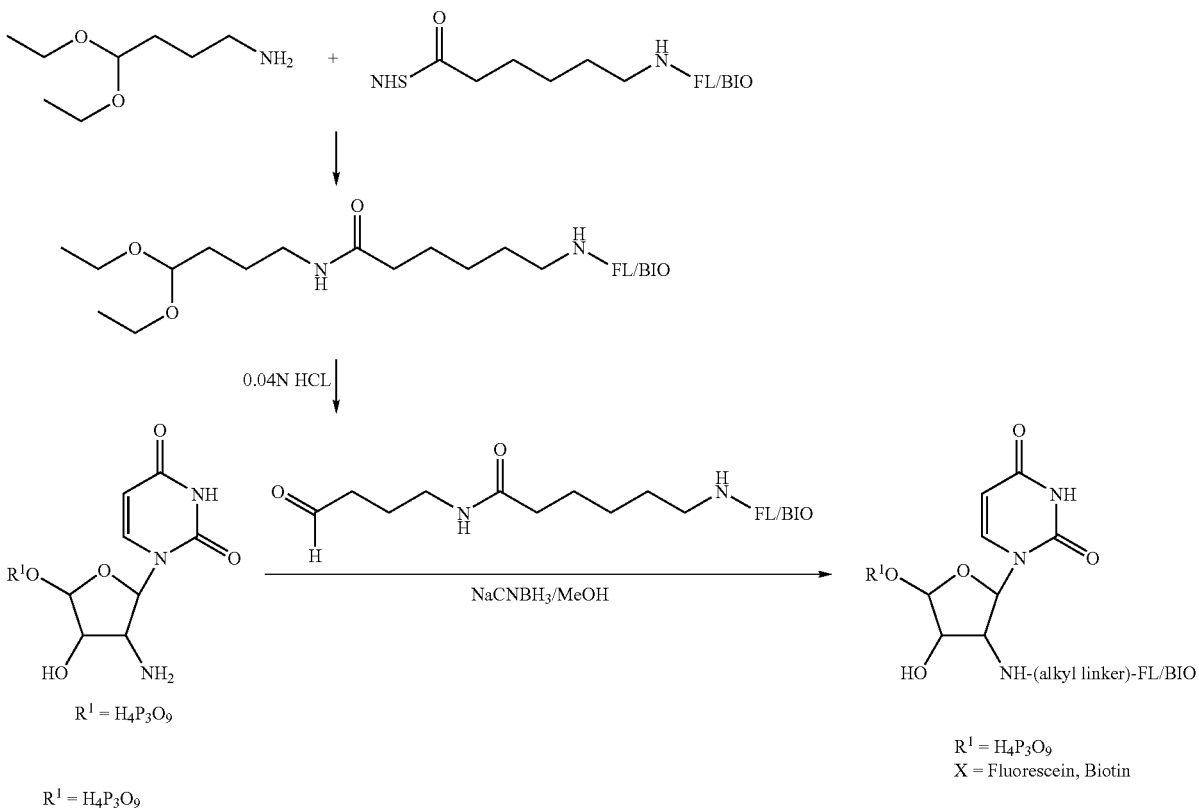
Example 20
Synthesis of 2'-O(6-(Fluorescein-5-carboxamido)hexyl)uridine 5'-O-triphosphate (Scheme 9)
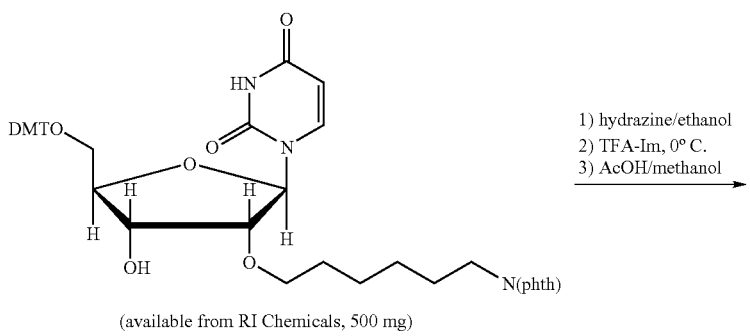

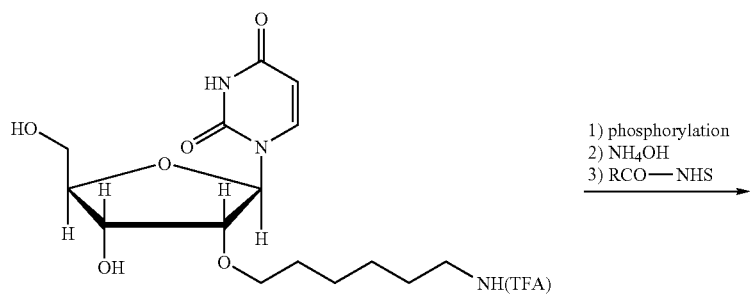
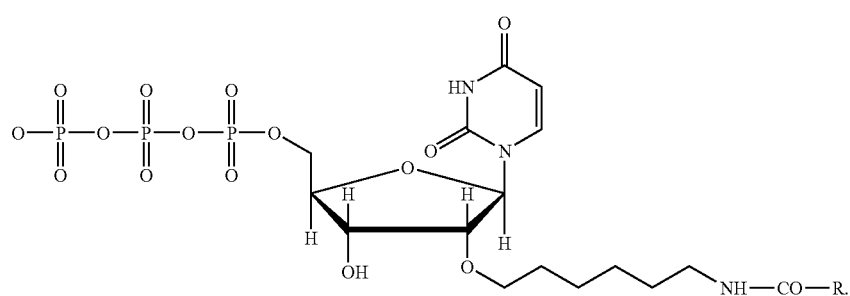
Example 21
Synthesis of 2'-S(N-(6-(Fluorescein-5-carboxamido)hexyl)aminoethyldithiouridine 5'-O-triphosphate (Scheme 8)
Scheme 10.
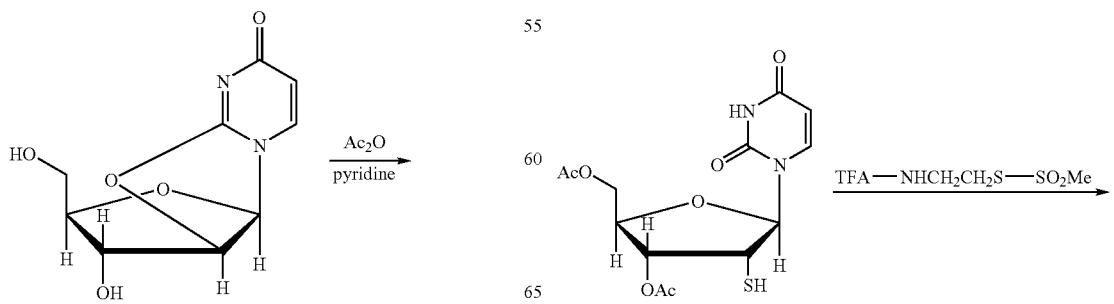

Example 30
Synthesis of Biotin-ΨisoCTP, propenamide-linked
(RLR-3b) (Scheme 30)
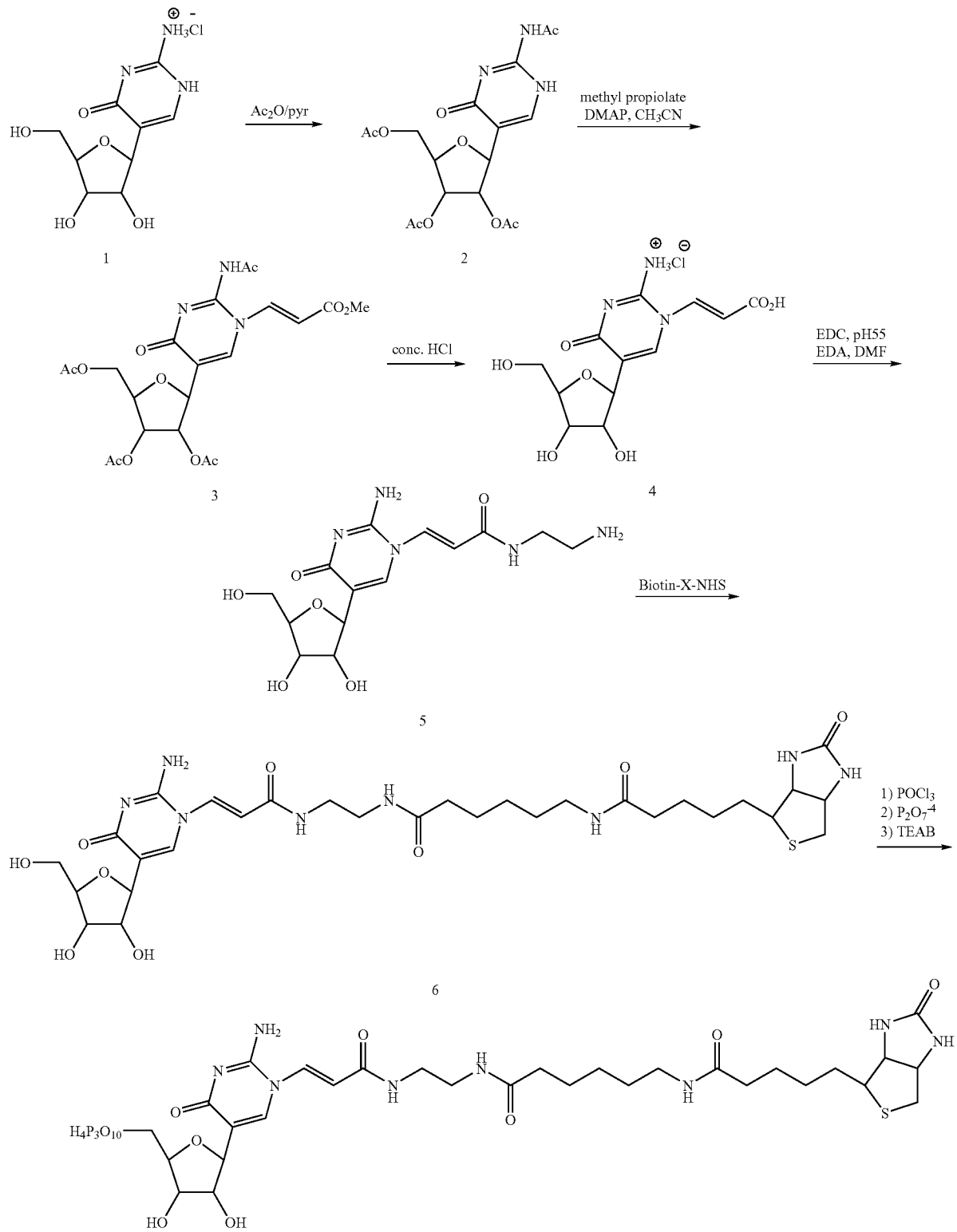

Peracetylated Pseudoisocytidine 2

Pseudoisocytidine (1) (2.5 g, 9 mmoles) was dissolved in 40 ml dry pyridine. Acetic anhydride (8.5 ml, 90 mmoles) was added and the mixture was stirred under argon for at least 4 hours at room temperature. The reaction can be monitored by HPLC (C18 column, buffer A: 0.1M TEAA, pH 7.5; buffer B: acetonitrile; gradient: 5-95% B over 20 minutes). The pyridine was removed under vacuum and the residual oil was dissolved in 500 ml of ethyl acetate. More ethyl acetate may be added to get a clear solution since the product has limited solubility in ethyl acetate. The organic phase was washed three times with brine and dried over anhydrous $Na_2SO_4$, filtered and the solvent removed. The white solid was recrystallized from ethyl acetate/hexane yielding 3.2 g (85%) of 2.

Propenoic Acid Methyl Ester 3

Compound 2 (2.0 g, 4.86 mmoles) and dimethylaminopyridine (1.2 g, 9.73 mmoles) were co-evaporated with 50 ml dry acetonitrile two times and then re-dissolved in 45 ml dry acetonitrile under argon. Methyl propiolate (0.82 g, 0.86 ml, 9.73 mmoles) was added and the solution was stirred at room temperature for 24 hours. The reaction turned from a colorless to amber colored solution. The reaction was followed by HPLC until no more product was produced. The solvent was removed by rotary-evaporation and the residue was dissolved in 400 ml of ethyl acetate and 200 ml of brine. The aqueous layer was back extracted with two 200 ml-portions of ethyl acetate. The combined organic layer was dried over anhydrous $Na_2SO_4$, filtered and the solvent removed. The residue was purified by flash column chromatography on silica gel (200 ml wet gel) using ethyl acetate as the eluent affording 850 mg (35%) of 3 as a white foam.

Propenoic Acid 4

Compound 3 (0.85 g, 1.7 mmoles) was dissolved in chloroform (5 ml) and aqueous concentrated hydrochloric acid (conc., 10 ml) was added. The rosy red solution turned a lemon yellow instantly. The reaction was stirred at room temperature for an additional 48 hours or until the reaction was complete as determined by RP-HPLC (C18 column, buffer A: 0.1M TEAA, pH 7.5; B, acetonitrile; gradient: 0% B for 9 minutes, 0 to 90% B over 10 minutes). The solvent and water were removed by rotary-evaporation. The product was purified by precipitation from methanol/acetonitrile and dried under vacuum to afford 500 mg (94%) of 4.

Aminopropenamide 5

Compound 4 (500 mg, 1.6 mmoles) and a buffered solution of ethylenediamine in water (8 ml of 2.0 M ethylenediamine in MES buffer, pH 5.5, containing 16 mmoles of EDA) were mixed and then 1-ethyl-3-(3-dimethylaminopropyl)carbodiimide (2 g, 16 mmoles) was added to the reaction with vigorous stirring. After 1 hour the reaction was analyzed by LC/MS and determined to be complete. The compound was purified by preparative HPLC: PRP-1, 30×250 mm column; flow rate 25 ml/min; buffers: A, 0.1M TEAA, pH 7.5, B, acetonitrile; gradient: 0% B for 9 minutes, 0 to 90% B over 10 minutes. Salts were removed with a retention time of about 4 min. and the compound eluted from 6 to 7.5 minutes. The collected fractions were pooled and the solvent removed under vacuum. The residue which contained triethylammonium acetate was co-evaporated with water several times and finally the product was precipitated from methanol/acetonitrile to afford 290 mg (51%) of 5.

Biotin-propenamide 6

Compound 5 (280 mg, 0.79 mmoles) was dissolved in dry DMF (5 ml) followed by the addition of triethylamine (160 mg, 220 µl, 1.58 mmoles). The pH of the solution was adjusted to 7.5 with the addition of more triethylamine, if necessary. Biotin-X-NHS ester (358 mg, 0.79 mmoles,) was then added to the mixture with stirring. After 1.5 hours the solvent volume was reduced under vacuum to about 1 ml. Caution: do no vacuum to dryness because this compound tends to aggregate and it will be difficult to redissolve. The compound was purified by preparative HPLC: PRP-1, 30×250 mm column; flow rate 25 ml/min; buffers: A, 0.1M TEAA, pH 7.5, B, acetonitrile; gradient: 0% B for 8 minutes, then 0 to 95% B over 20 minutes. Fractions were collected across the peak from 16-17 min and the solution of pooled fractions was quantitated for the presence of product spectrophotometrically ($\lambda_{289}$, assuming $\epsilon$=8000). The solvent was removed under vacuum and the residue was co-evaporated with water (30 ml) three times and methanol (50 ml) two times. The product was precipitated from methanol/acetonitrile yielding 379 mg (69%) of 6.

Triphosphate

Compound 6 (110 mg, 0.1585 mmoles) was dried over $P_2O_5$ under vacuum for two days and then dissolved in trimethyl phosphate (dried over molecular sieves, 20 ml) with gentle heating to about 60° C. Once the material dissolved, the solution was cooled to ambient temperature and a trap-pack (ABI Trap-pak, P#GEN 084034) was added and the mixture was allowed to gently stir overnight. The trap-pack was removed and to the solution at 0° C. under argon was added $POCl_3$ (73 mg, 45 µl, 0.48 mmoles). The reaction was monitored by AX-HPLC for the conversion to the monophosphate, and after 4 hours, an additional 2 equivalents of $POCl_3$ were added and the reaction was allowed to stir for 2 more hours (or until 90% conversion was achieved).

While monitoring the reaction, a solution of dry tetra(tri-n-butylammonium)pyrophosphate (2.35 mmoles) in 5 ml of dry DMF was prepared as follows: n-butylammonium pyrophosphate (Aldrich, P-8533, 1.1 g, 2.35 mmoles) was dissolved in 5 ml dry DMF. To the solution was added tri-n-butylamine (218 mg, 280 µl, 1.2 mmoles). The solvent was removed under vacuum and the residue was co-evaporated three times with 5 ml of dry DMF. To the ammonium salt in 5 ml of dry DMF was added additional tri-n-butylamine (1.12 ml, 2.35 mmoles)]. Then the reaction was added drop wise to the pyrophosphate solution with vigorous stirring. After 5 minutes, triethylammonium bicarbonate (1.0 M, pH 7.5, 20 ml) was added to quench the reaction and the mixture was then analyzed by HPLC (70% triphosphate). The solution was then diluted 100 times with water and loaded directly on to a DEAE ion-exchange column and purified using standard procedures.

Example 31
Synthesis of Biotin-ΨUTP, propenamide-linked (RLR-2B)
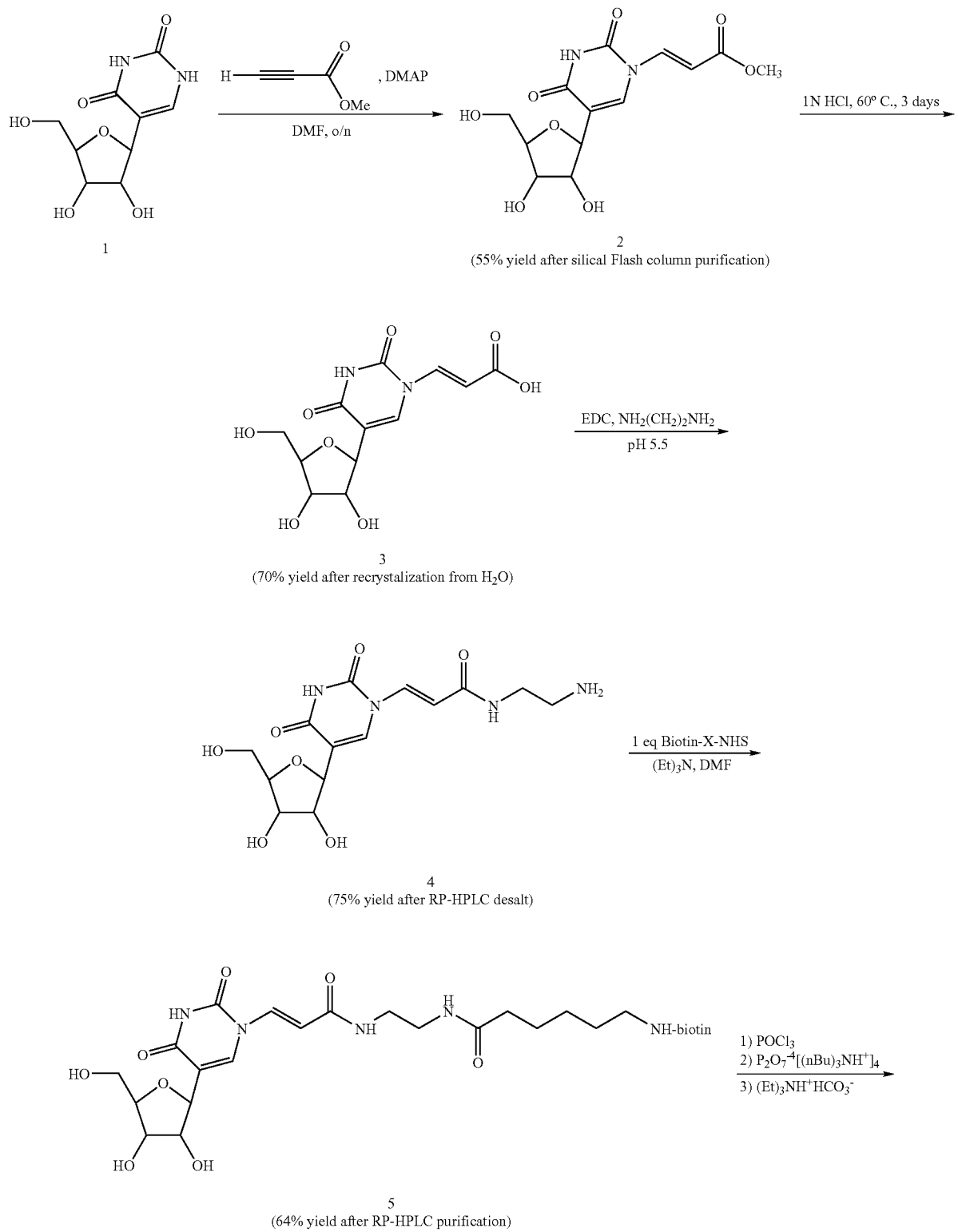

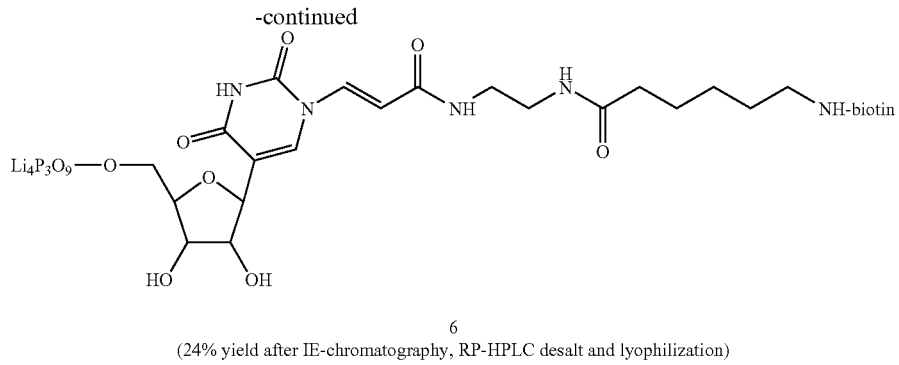

6
(24% yield after IE-chromatography, RP-HPLC desalt and lyophilization)

Propenoic Acid Methyl Ester 2

Compound 1 (2.5 g, 10.2 mmoles) and dimethylaminopyridine (1.25 g, 10.2 mmoles) were dissolved in 125 ml dry DMF under argon. Methyl propiolate (0.943 g, 1.0 ml, 11.2 mmoles) was added and the solution was stirred at room temperature for 24 hours. The reaction turned from a colorless to amber colored solution. The reaction was followed by HPLC until no more product was produced. The solvent was removed by roto-evaporation and the residue was dissolved in 10 ml methanol-acetonitrile (1:1 volume). It was purified by preparative PRP-1, 30×250 mm column using water as buffer A and acetonitrile as buffer B with a flow rate 25 ml/min. Eluting from 5 to 95% B in 15 minutes. Collect the fraction from 9 to 10 minute. Remove solvent to afford 1.1 g (33%) as a white solid.

Propenoic Acid 3

Compound 2 (1.1 g, 3.35 mmoles) was dissolved in 80 ml 1.0 N HCl and heated to 60° C. for 88 hours when LC-MS indicated the starting material is completed converted. The reaction mixture was evaporated to an oily residual by rotary-evaporation and redissolve in minimum amount of methanol. Add the methanol solution slowly to acetonitrile (at least 200 ml) to precipitate the free acid. Collect the solid and dried under vacuum to afford 1.0 g (94%) of white solid.

Aminopropenamide 4

Compound 3 (1.0 g, 3.18 mmoles) and a buffered solution of ethylenediamine in water (16 ml of 2.0 M ethylenediamine in 0.1 M MES buffer, pH 5.5, containing 32 mmoles of EDA) were mixed and then 1-ethyl-3-(3-dimethylaminopropyl)carbodiimide (4 g, 32 mmoles) was added to the reaction with vigorous stirring. After 1 hour the reaction was analyzed by LC/MS and determined to be complete. Note: desalt a sample for LC-MS. The compound was purified by preparative HPLC: PRP-1, 30×250 mm column; flow rate 25 ml/min; buffers: A, 0.1M TEAA, pH 7.5, B, acetonitrile; gradient: 0% B for 9 minutes, 0 to 90% B over 10 minutes. Salts were removed with a retention time of about 4 min. and the compound eluted from 6 to 7.5 minutes. The fractions were pooled and the solvent removed under vacuum. The residue which contained triethylammonium acetate was co-evaporated with water several times and finally the product was precipitated from methanol/acetonitrile to afford 700 mg (62%) of 4.

Biotin-propenamide 5

Compound 4 (102 mg, 0.286 mmoles) was co-evaporated with dry DMF twice (5 ml each) and then dissolved in dry DMF (1.5 ml) followed by the addition of triethylamine (29 mg, 40 µl, 0.286 mmoles). The pH of the solution was adjusted to 7.5 with the addition of more triethylamine, if necessary. Biotin-X-NHS ester (0.286 mmoles, 130 mg) was then added to the mixture with stirring. After 1.0 hour, the reaction was monitored by HPLC for completion. The solvent volume was reduced under vacuum to about 1 ml. Caution: do not vacuum to dryness because this compound tends to aggregate and it will be difficult to redissolve. The residual was redissolved in 5 ml water and 1 ml methanol.

The compound was purified by preparative HPLC: PRP-1, 30×250 mm column; flow rate 25 ml/min; buffers: A, 0.1M TEAA, pH 7.5, B, acetonitrile; gradient: 0% B for 11 minutes, then 0 to 95% B over 16 minutes. Fractions were collected across the peak from 19-21 min. The solvent was removed under vacuum and the residue was co-evaporated with water (30 ml) three times and methanol (50 ml) two times. The product was recrystallized from acetonitrile yielding 130 mg (67%) of 5.

Triphosphate 6

Compound 5 (130 mg, 0.187 mmoles) was dried over $P_2O_5$ under vacuum for 24 hours and then dissolved in trimethyl phosphate (dried over molecular sieves, 20 ml) with gentle heating to about 60° C. Once the material dissolved the solution was cooled to ambient temperature and a trap-pack (ABI Trap-pak, P#GEN 084034) was added and allowed to gently stir overnight. The solution turned into a little cloudy when chilled on ice. The trap-pack was removed and to the solution at 0° C. under argon was added $POCl_3$ (115 mg, 70 µl, 0.748 mmoles). The reaction was monitored by AX-HPLC for the conversion to the monophosphate, and after 4 hours, an additional one equivalent of $POCl_3$ were added and the reaction was allowed to stir for 2 more hours (90% conversion). While monitoring the reaction, a solution of dry tetra(tri-N-butylammonium)pyrophosphate (0.187×5×3.3=3.1 mmoles) in 6 ml dry DMF was prepared. Then the reaction was added drop wise to the pyrophosphate solution with vigorous stirring. After 5 minutes, triethylammonium bicarbonate (1.0 M, pH 7.5, 23 ml) was added to quench the reaction. The mixture was stirred on ice for 30 minutes and placed in a fridge overnight. The mixture was then analyzed by HPLC (70% triphosphate) and purified using standard TriLink procedures on DEAE.

The final reaction mixture may be diluted with mili Q water by a factor of 100, and then loaded on DEAE column. It is not recommended to rotovap off TEAB because the compound may be unstable under basic condition.

To prepare tetra(tri-N-butylammonium)pyrophosphate, TBA-PPi (Aldrich, P-8533, 1.5 TBA per PPi, 1.4 g, 3.1 mmoles) was dissolved in 5 ml dry DMF.

Add TBA 287 mg, 364 µl, 1.55 mmoles). Co-evaporate with 5 ml dry DMF at least three times. Redissolve in 5 ml anhydrous DMF. Add TBA (1.46 ml, 3.1 mmoles). Handle the materials in a glove box filled with Ar.

Example 32

Synthesis of Biotin-virtual NTP (schemes 32)

The Allonic methyl ester 1 (2.5 g,) was treated with 20 ml ethylenediamine (as solvent) at 25° C. for 24 hrs. The EDA was removed by rotary evaporation and the residue was co-evaporated several times with water until all of the EDA was removed (as measured by TLC on silica in 10% MeOH/DCM using ninhydrin stain) affording allonamide, quantitatively. The extent of reaction was analyzed by RP-HPLC and then was characterized by HNMR/MS. The purity was good with very little contaminating EDA present so that the allonamide was taken on to the next step without further purification. To the allonamide in DMF were added 1.1 equivalents of Biotin-X-NHS (commercially available from Clonetech) followed by 2 equivalents of triethylamine. The solution was stirred overnight at room temperature and analyzed by HPLC for extent of reaction. The solvent was then removed by evaporation and the residue was purified by column chromatography on silica eluting with a linear, stepwise gradient of 1-10% MeOH/DCM to afford 50% of 2 (NMR/MS see attachment). The trityl group of 2 was removed by treatment with 20 ml of a solution of 10% TFA/MeOH. The reaction was monitored by TLC, 10% MeOH/DCM and visualized using an acidic solution of dimethylaminocinnamanaldehyde/EtO. The reaction was diluted with DCM and the product was extracted into water. The water was removed by rotary evaporation and the residue was purified by precipitation by slow addition of a methanol solution of the biotinylated product to ethyl acetate to form 196 mg (71%) of pure biotinylated nucleoside. The yellow sticky foam was co-evaporated with dry pyridine 3-times to remove water and used directly in the phosphorylation reaction (scheme 32a).

At this point, the nucleoside was phosphorylated to 3 using standard conditions for the preparation of dexyribonucleotide triphosphates[2].

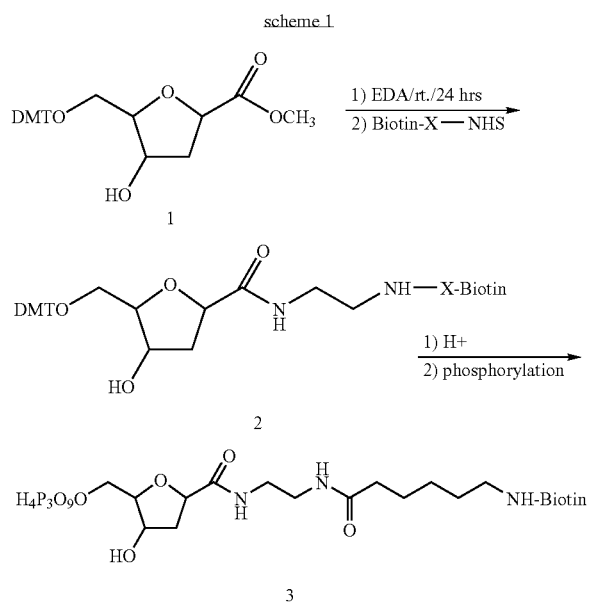

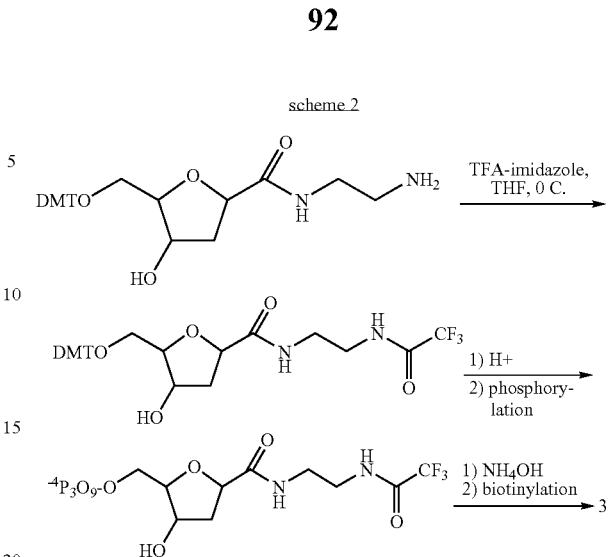

Example 33

Figure 21:
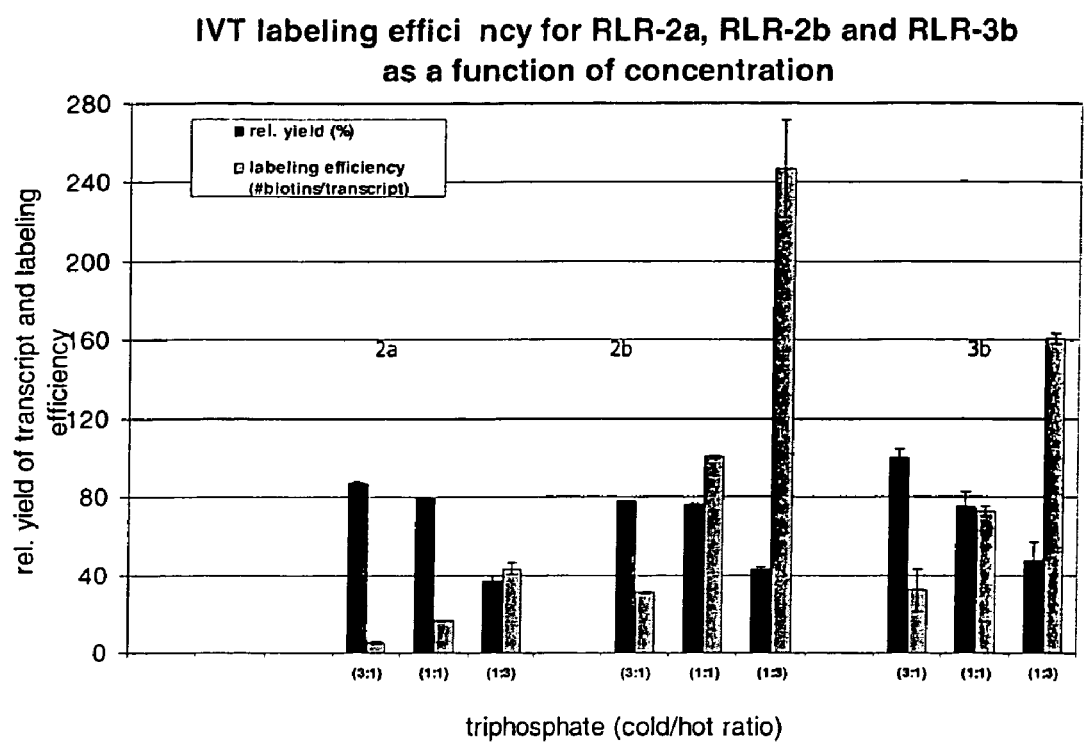
FIG. 21 shows IVT incorporation of saturated versus vinyl linkers attached to nucleic acid labeling compounds.

IVT incorporation was determined spectrophotometrically using 260 nm absorbance for the quantitation of RNA and a HABA-based colorimetric assay for quantitation of biotin for RLR-3b (Biotin-ΨisoCTP, vinyl-linked), RLR-2b (Biotin-ΨUTP, vinyl-linked) and RLR-2a (Biotin-ΨUTP, ethane (or saturated)-link). The vinyl linked analogs (2b and 3b) were both incorporated more efficiently than the saturated ethane analog (2a) at all mixtures of cold to hot nucleotides as shown in FIG. 21. Purified and fragmented RNA was quantitated by UV absorbance at 260 nm, and the amount of biotin incorporated was determined using a spectrophotometric-based assay for biotin (see, e.g., Swaisgood, H. E. et al 1996 *Applied Biochemistry and Biotechnology*,56, 1.)

All patents, patent applications, and literature cited in the specification are hereby incorporated by reference in their entirety. In the case of any inconsistencies, the present disclosure, including any definitions therein will prevail.

The invention has been described with reference to various specific and preferred embodiments and techniques. However, it should be understood that many variations and modifications may be made while remaining within the spirit and scope of the invention.

The invention claimed is:

1. A nucleic acid labeling compound of the following structure:

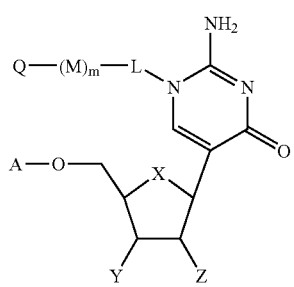

wherein
A is H, monophosphate, diphosphate, triphosphate, a-thiotriphosphate, phosphoramidite, or H-phosphonate;

X is O;

Y is H, N$_3$, F, OR$_9$, SR$_9$ or NHR$_9$, wherein R$_9$ is H, alkyl or aryl;

Z is H, N$_3$, F or OR$_{10}$, wherein R$_{10}$ is H, alkyl or aryl;

L is a linker group selected from the group consisting of —CH=CH—R$_{11}$, or C≡C—R$_{11}$ wherein R$_{11}$ comprises a moiety selected from the group consisting of alkyl, functionalized alkyl, alkenyl alkyl, alkynyl alkyl, amido alkyl, amino alkyl, alkoxy, amino, aryl, and thio;

Q is selected from the group consisting of a radiolabel, a magnetic particle, colloidal gold, fluorescein, texas red, rhodamine, green fluorescent protein, luminol, lophine, acridine salts, luciferin, vanadium spin labels, copper spin labels, iron spin labels, manganese spin labels, nitroxide free radicals, quinoline dyes, triarylmethane dyes, acridine dyes, colored glass beads, polystyrene beads, polypropylene beads, latex beads, biotin, horseradish peroxidase, alkaline phosphatase, 1-aminonaphthalene, 2-aminonaphthalene, p,p'-diaminostilbenes, pyrenes, quaternary phenanthridine salts, 9-aminoacridines, p,p'-diaminobenzophenone imines, anthracenes, oxacarbocyanines. marocyanine, 3-amino aminoequilenin, perylene, bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salycilate, strophanthidin, porphyrins, triarylmethanes, flavin, xanthene dyes, rhodamine dyes, cyanine dyes, 4,4-difluoro-4-bora-3a,4a-diaza-s-indacene dyes, phycobiliprotein, dansyl chloride, 3,6-dihydroxy-9-phenylxanthhydrol, rhodamineisothyocyanate, N-phenyl-1-amino-8-sulfonatonaphthalene, N-phenyl-2-amino-6-sulfonatonaphthalene, 4-acetamido-4-isothiocyanatostilbene-2,2'-disulfonic acid, pyrene-3-sulfonic acid, 2-toluidinonaphthalene-6-sulphonate, N-phenyl,N-methyl-2-aminonaphthalene-6-sulphonate, ethidium bromide, stebrine, auromine-0,2-(9'-anthroyl)palmitate, dansyl phosphatidylethanolamin, N,N'-dioctadecyloxacarbocyanine, N,N'-dihexyl oxacarbocyanine, merocyanine, 4-(3'-pyrenyl)butyrate, d-3-aminodesoxy-eguilenin, 12-(9'-anthroyl)stearate, 2-methylanthracene, 9-vinylanthracene, 2,2'-(vinylene-p-phenylene) bisbenzoxazole, p-bis [2-(4-methyl-5-phenyl oxazolyl)]benzene, 6-dimethylamino-1,2-benzophenzin, retinol, bis (3'-aminopyridinium)-1,10-decandiyl diiodide, sulphonaphthylhydrazone of hellibrienin, chlorotetracycline, N-(7-dimethyl amino-4-methyl-2-oxo-3-chromenyl)maleimide,N-[p-(2-benzimidazolyl)phenyl]maleimide,N-(4-fluoranthyl)maleimide, bis(homovanillic acid), resazarin, 4-chloro-7-nitro-2,1,3-benzooxadizole, merocyanine 540, resorufin, rose bengal, and 2,4-diphenyl-3(2H)-furanone; and M is a connecting group selected from the group consisting of amino alkyl, —CO(CH$_2$)$_5$NH—, —CO—, —CO(O)—, —CO(NH)—, —CO(CH$_2$)$_5$NHCO(CH$_2$)$_5$NH—, —NH(CH$_2$CH$_2$O)$_K$NH—, —NH(CH$_2$CH$_2$O)$_k$CH$_2$CH$_2$NH—, and —CO(CH$_2$)$_5$-, wherein k is an integer from 1 to 5 and wherein m is an integer ranging from 0 to 3.

2. A nucleic acid labeling compound according to claim 1 wherein A is selected from the group consisting of H, α-thiotriphosphate and H$_4$O$_9$P$_3$—; Y is H or OH; Z is H or OR$_{10}$, wherein R$_{10}$ is H, alkyl or aryl.

3. A nucleic acid labeling compound according to claim 2 wherein Q is selected from the group consisting of colloidal gold, fluorescein, texas red, rhodamine, green fluorescent protein, 1-aminonaphthalene, 2-aminonaphthalene, p,p'-diaminostilbenes, pyrenes, quaternary phenanthridine salts, 9-aminoacridines, p,p'-diaminobenzophenone imines, anthracenes,oxacarbocyanines, marocyanine, 3-amino aminoequilenin, perylene,bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salycilate, strophanthidin, porphyrins, triarylmethanes, flavin, xanthene dyes, rhodamine dyes, cyanine dyes, 4,4-difluoro-4-bora-3a,4a-diaza-s-indacene dyes, phycobil iprotein, dansyl chloride, 3,6-dihydroxy-9-phenylxanthhydrol, rhodamineisothyocyanate, N-phenyl-1-amino-8-sulfonatonaphthalene, N-phenyl-2-amino-6-sulfonatonaphthalene, 4-acetamido-4-isothiocyanatostilbene-2,2'-disulfonic acid, pyrene-3-sulfonic acid, 2-toluidinonaphthalene-6-sulphonate, N-phenyl, N-methyl-2-aminonaphthalene-6-sulphonate, ethidium bromide, stebrine, auromine-0,2-(9'-anthroyl) palmitate, dansyl phosphatidylethanolamin, N,N'-dioctadecyloxacarbocycanine, N,N'-dihexyl oxacarbocyanine, merocyanine, 4-(3'-pyrenyl)butyrate, d-3-aminodesoxy-equilenin, 12-(9'-anthroyl)stearate, 2-methylanthracene, 9-vinylanthracene, 2,2'-(vinylene-p-phenylene) bisbenzoxazole, p-bis [2-(4-methyl-5-phenyl oxazolyl)]benzene, 6-dimethylamino-1,2-benzophenzin, retinol, bis (3'-aminopyridinium)-1,10-decandiyl diiodide, sulphonaphthylhydrazone of hellibrienin, chlorotetracycline, N-(7-dimethyl amino-4-methyl-2-oxo-3-chromenyl)maleimide ,N-[p-(2-benzimidazolyl)phenyl]maleimide, N-(4-fluoranthyl)maleimide, bis(homovanillic acid), resazarin, 4-chloro-7-nitro-2, 1,3-benzooxadizole, merocyanine 540, resorufin, rose bengal, and 2,4-diphenyl-3(2H)-furanone, and biotin.

4. A nucleic acid labeling compound according to claim 3 wherein Q is a biotin.

5. A nucleic acid labeling compound according to claim 3 having a first M and a second M, wherein said first M is —NH(CH$_2$)$_n$NH—, wherein n is an integer from 2 to 10, and said second M is —CO(CH$_2$)pNH—, wherein p is an integer from 2 to 10 and m is 2.

6. A nucleic acid labeling compound according to claim 5 wherein said first M is —NH(CH$_2$)$_2$NH— and said second M is —CO(CH$_2$)$_5$NH—.

7. A nucleic acid labeling compound according to claim 1 wherein A is a triphosphate group having appropriate counterions and Y is OH and Z is OH.

8. A nucleic acid labeling compound according to claim 7 wherein said appropriate counterions are selected from the group consisting of H$^+$, Na$^+$, Li$^+$, K$^+$, (CH$_3$CH$_2$)$_3$NH$^+$ and NH$_4^+$.

9. A method of synthesizing a labeled nucleic acid comprising attaching a nucleic acid labeling compound according to claim 1 to a nucleic acid.

10. A method of detecting a nucleic acid comprising incubating a nucleic acid derivative with a complementary probe, wherein said nucleic acid derivative is prepared by coupling a nucleic acid labeling compound according to claim 1 with a nucleic acid.

11. A method according to claim 10, wherein the probe is attached to a solid support.

12. A method according to claim 11, wherein said solid support is glass.

13. A nucleic acid labeling compound having the formula:

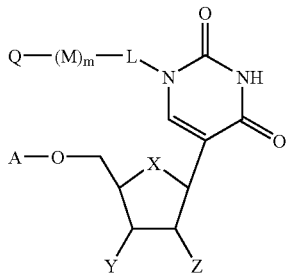

wherein
A is H, monophosphate, diphosnhate, triphosphate, α-thiotriphosphate, phosphoramidite, or H-phosphonate;
X is O;
Y is H, $N_3$, F, $OR_9$, $SR_9$ or $NH_9$, wherein $R_9$ is H, alkyl or aryl;
Z is H, $N_3$, F or $OR_{10}$, wherein $R_{10}$ is H, alkyl or aryl;
L comprises a vinyl group (—CH═CH—) wherein said vinyl group is attached directly to the N atom of the base;
Q is selected from the group consisting of a radiolabel, a magnetic particle, colloidal gold, fluorescein, texas red, rhodamine, green fluorescent protein, luminol, lophine, acridine salts, luciferin, vanadium spin labels, copper spin labels, iron spin labels, manganese spin labels, nitroxide free radicals, quinoline dyes, triarylmethane dyes, acridine dyes, colored glass beads, polystyrene beads, polypropylene beads, latex beads, biotin, horseradish peroxidase, alkaline phosphatase, 1-aminonaphthalene, 2-aminonaphthalene, p,p'-diaminostilbenes, pyrenes, quatemary phenanthridine salts, 9-aminoacridines, p,p'-diaminobenzophenone imines, anthracenes,oxacarbocyanines, marocyanine, 3-amino aminoeuuilenin, perylene,bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salycilate, strophanthidin, porphyrins, triarylmethanes, flavin, xanthene dyes, rhodamine dyes, cyanine dyes, 4,4-difluoro-4-bora-3a,4a-diaza-s-indacene dyes, phycobiliprotein, dansyl chloride, 3,6-dihydroxy-9-phenylxanthhydrol, rhodamineisothyocyanate, N-phenyl-1-amino-8-sulfonatonaphthalene, N-phenyl-2-amino-6-sulfonatonaphthalene, 4-acetamido-4-isothiocyanatostilbene-2,2'-disulfonic acid, pyrene-3-sulfonic acid, 2-toluidinonaphthalene-6-sulphonate, N-phenyl,N-methyl-2-aminonaphthalene-6-sulphonate, ethidium bromide, stebrine, aurornine-0,2-(9'-anthroyl)palmitate, dansyl phosphatidylethanolamin, N,N'-dioctadecyloxacarbocyanine, N,N'-dihexyl oxacarbocyanine, merocyanine, 4-(3'-pyrenyl)butyrate, d-3-aminodesoxy-equilenin, 12-(9'-anthroyl)stearate, 2-methylanthracene, 9-vinylanthracene, 2,2'-(vinylene-p-phenylene) bisbenzoxazole, p-bis [2-(4-methyl-5-phenyl oxazolyl)]benzene, 6-dimethylamino-1,2-benzophenzin, retinol, bis (3'-aminopyridinium)-1,10-decandiyl diiodide, sulphonaphthylhydrazone of hellibrienin, chlorotetracycline, N-(7-dimethyl amino-4-methyl-2-oxo-3-chromenyl)maleimide,N-[p-(2-benzimidazolyl)pheny]maleimide,N-(4-fluoranthyl)maleimide, bis(homovanillic acid), resazarin, 4-chloro-7-nitro-2,1,3-benzooxadizole, merocyanine 540, resorufin, rose bengal, and 2,4-diphenyl-3(2H)-furanone, and M is a connecting group selected from the group consisting of amino alkyl, —$CO(CH_2)_5NH$—, —CO—, —CO(O)—, —CO(NH)—, —$CO(CH_2)_5NHCO(CH_2)_5NH$—, —$NH(CH_2CH_2O)_kNH$—, —$NH(CH_2CH_2O)_kCH_2CH_2NH$— and —$CO(CH_2)_5$—, wherein k is an integer from 1 to 5, wherein m is an integer ranging from 0 to 3.

14. A nucleic acid labeling compound according to claim 1 wherein L is —CH═CH—$R_{11}$, wherein $R_{11}$ comprises a moiety selected from the group consisting of alkyl, functionalized alkyl, alkenyl alkyl, alkynyl alkyl, amido alkyl, amino alkyl, alkoxy, amino, aryl, and thio.

15. A nucleic acid labeling compound according to claim 14 where $R_{11}$ is $C(O)R_{12}$, where $R_{12}$ comprises a moiety selected from the group consisting of a bond, alkyl, functionalized alkyl, alkenyl alkyl, alkynyl alkyl, amido alkyl, amino alkyl, alkoxy, amino, aryl, and thio.

16. A nucleic acid labeling according to claim 13 wherein A is selected from the group consisting of H, α-thiotriphosphate, and $H_4O_9P_3$—; Y is H or OH; Z is H or $OR_{10}$, wherein $R_{10}$ is H, alkyl or aryl.

17. A nucleic acid labeling compound according to claim 13 wherein Q is selected from the group consisting of colloidal gold, fluorescein, texas red, rhodamine, green fluorescent protein, 1-aminonaphthalene, 2-aminonaphthalene, p,p'-diaminostilbenes, pyrenes, quatemary phenanthridine salts, 9-aminoacridines, p,p'-diaminobenzophenone imines, anthracenes, oxacarbocyanines, marocyanine, 3-amino aminoequilenin, perylene,bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salycilate, strophanthidin, porphyrins, triarylmethanes, flavin, xanthene dyes, rhodamine dyes, cyanine dyes, 4,4-difluoro-4-bora-3a, 4a-diaza-s-indacene dyes, phycobil iprotein, dansyl chloride, 3,6-dihydroxy-9-phenylxanthhydrol, rhodamineisothyocyanate, N-phenyl-1-amino-8-sulfonatonaphthalene, N-phenyl-2-amino-6-sulfonatonaphthalene, 4-acetamido-4-isothiocyanatostilbene-2,2'-disulfonic acid, pyrene-3-sulfonic acid, 2-toluidinonaphthalene-6-sulphonate, N-phenyl, N-methyl-2-aminonaphthalene-6-sulphonate, ethidium bromide, stebrine, auromine-0,2-(9'-anthroyl)palmitate, dansyl phosphatidylethanolamin, N,N'-dioctadecyloxacarbocyanine, N,N'-dihexyl oxacarbocyanine, merocyanine, 4-(3'-pyrenyl)butyrate, d-3-aminodesoxy-equilenin, 12-(9'-anthroyl)stearate, 2-methylanthracene, 9-vinylanthracene, 2,2'-(vinylene-p-phenylene) bisbenzoxazole, p-bis [2-(4-methyl-5-phenyl oxazolyl)]benzene, 6-dimethylamino-1,2-benzophenzin, retinol, bis (3'-aminopyridinium)-1,10-decandiyl diiodide, sulphonaphthylhydrazone of hellibrienin, chlorotetracycline, N-(7-dimethyl amino-4-methyl-2-oxo-3-chromenyl)maleimide, N-[p-(2-benzimidazolyl)phenyl]maleimide, N-(4-fluoranthyl)maleimide, bis(homovanillic acid), resazarin, 4-chloro-7-nitro-2, 1,3-benzooxadizole, merocyanine 540, resorufin, rose bengal, and 2,4-diphenyl-3(2H)-furanone, and biotin.

18. A nucleic acid labeling compound according to claim 15, wherein $R_{12}$ is a bond, having a first M and a second M, wherein said first M is —$NH(CH_2)_nNH$—, wherein n is an integer from 2 to 10, and second M is —$CO(CH_2)pNH$—, wherein p is an integer from 2 to 10 and m is 2.

19. A nucleic acid labeling compound according to claim 18 wherein said first M is —NH(CH$_2$)$_2$NH— and said second M is —CO(CH$_2$)$_5$NH— and m is 2, having the structure:

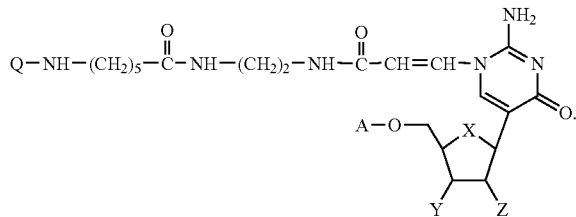

20. A nucleic acid labeling compound according to claim 13 wherein A is a triphosphate group having appropriate counterions.

21. A nucleic acid labeling compound according to claim 20 wherein said appropriate counterion is selected from the group consisting of H$^+$, Na$^+$, Li$^+$, K$^+$, (CH$_3$)$_3$NH$^+$ and NH$_4^+$.

22. A nucleic acid labeling compound according to claim 13 wherein L is —CH═CH—R$_{11}$, where R$_{11}$ comprises a moiety selected from the group consisting of alkyl, functionalized alkyl, alkenyl alkyl, alkynyl alkyl, amido alkyl, amino alkyl, alkoxy, amino, aryl, and thio.

23. A nucleic acid labeling compound according to claim 13 where R$_{11}$ is C(O)R$_{12}$, where R$_{12}$ comprises a moiety selected from the group consisting of a bond, alkyl, functionalized alkyl, alkenyl alkyl, alkynyl alkyl, amido alkyl, amino alkyl, alkoxy, amino, aryl, and thio.

24. A nucleic acid labeling compound according to claim 13 wherein A is selected from the group consisting of H, α-thiotriphosphate, and
   H$_4$O$_9$P$_3$;
   Y is H or OH; Z is H or OR$_{10}$, wherein R$_{10}$ is H, alkyl or aryl.

25. A nucleic acid labeling compound according to claim 13 wherein Q is selected from the group consisting of colloidal gold, fluorescein, texas red, rhodamine, green fluorescent protein, 1-aminonaphthalene, 2-aminonaphthalene, p,p'-diaminostilbenes, pyrenes, quatemary phenanthridine salts, 9-aminoacridines, p,p'-diaminobenzophenone imines, anthracenes, oxacarbocyanines, marocyanine, 3-amino aminoequilenin, perylene,bisbenzoxazole, bis-p-oxazolyl benzene, 1,2-benzophenazin, retinol, bis-3-amino-pridinium salts, hellebrigenin, tetracycline, sterophenol, benzimidazolyl phenylamine, 2-oxo-3-chromen, indole, xanthen, 7-hydroxycoumarin, phenoxazine, salycilate, strophanthidin, porphyrins, triarylmethanes, flavin, xanthene dyes, rhodamine dyes, cyanine dyes, 4,4-difluoro-4-bora-3a,4a-diaza-s-indacene dyes, phycobiliprotein, dansyl chloride, 3,6-dihydroxy-9-phenylxanthhydrol, rhodamineisothyocyanate, N-phenyl-1-amino-8-sulfonatonaphthalene, N-phenyl-2-amino-6-sulfonatonaphthalene, 4-acetamido-4-isothiocyanatostilbene-2,2'-disulfonic acid, pyrene-3-sulfonic acid, 2-toluidinonaphthalene-6-sulphonate, N-phenyl, N-methyl-2-aminonaphthalene-6-sulphonate, ethidium bromide, stebrine, auromine-0,2-(9'-anthroyl) palmitate, dansyl phosphatidylethanolamin, N,N'-dioctadecyloxacarbocyanine, N,N'-dihexyl oxacarbocyanine, merocyanine, 4-(3'-pyrenyl)butyrate, d-3-aminodesoxyequilenin, 12-(9'-anthroyl)stearate, 2-methylanthracene, 9-vinylanthracene, 2,2'-(vinylene-p-phenylene) bisbenzoxazole, p-bis [2-(4-methyl-5-phenyl oxazolyl)]benzene, 6-dimethylamino-1,2-benzophenzin, retinol, bis (3'-aminopyridinium)-1,10-decandiyl diiodide, sulphonaphthylhydrazone of hellibrienin, chlorotetracycline, N-(7-dimethyl amino-4-methyl-2-oxo-3-chromenyl)maleimide, N-[p-(2-benzimidazolyl)phenyl]maleimide, N-(4-fluoranthyl)maleimide, bis(homovanillic acid), resazarin, 4-chloro-7-nitro-2,1,3-benzooxadizole, merocyanine 540, resorufin, rose bengal, and 2,4-diphenyl-3(2H)-furanone, and biotin.

26. A nucleic acid labeling compound according to claim 23, wherein R$_{12}$ is a bond, having a first M and a second M wherein said first M is —NH(CH$_2$)$_n$NH—, wherein n is an integer from 2 to 10, and said second M is —CO(CH$_2$)$_p$NH—, wherein p is an integer from 2 to 10 and m is 2.

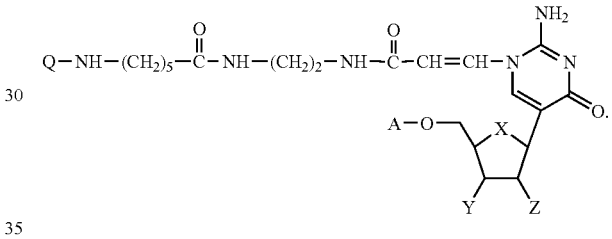

27. A nucleic acid labeling compound according to claim 24 wherein A is a triphosphate group having an appropriate counterion.

28. A nucleic acid labeling compound according to claim 24 wherein said appropriate counterion is selected from the group consisting of H$^+$, Na$^+$, Li$^+$, K$^+$, (CH$_3$)$_3$NH$^+$ and NH$_4^+$.

29. A nucleic acid derivative produced by coupling a nucleic acid labeling compound according to claim 24 with a nucleic acid.

30. A hybridization product comprising the nucleic acid derivative according to claim 29 bound to a complementary probe.

31. The hybridization product according to claim 30, wherein the complementary probe is attached to a solid support.

32. The hybridization product according to claim 31 wherein said solid support is glass.

* * * * *